(12) United States Patent
Rush et al.

(10) Patent No.: US 12,157,791 B2
(45) Date of Patent: *Dec. 3, 2024

(54) COMPOSITIONS AND METHODS OF MAKING POLYMERIZED NUCLEIC ACIDS

(71) Applicant: The Regents of the University of California, Oakland, CA (US)

(72) Inventors: Anthony M. Rush, San Diego, CA (US); Nathan Gianneschi, San Diego, CA (US); Carrie James, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 440 days.

This patent is subject to a terminal disclaimer.

(21) Appl. No.: 17/172,793

(22) Filed: Feb. 10, 2021

(65) Prior Publication Data

US 2021/0301078 A1    Sep. 30, 2021

Related U.S. Application Data

(63) Continuation of application No. 15/329,526, filed as application No. PCT/US2015/042482 on Jul. 28, 2015, now Pat. No. 11,072,681.

(60) Provisional application No. 62/029,833, filed on Jul. 28, 2014.

(51) Int. Cl.
*C08G 61/02* (2006.01)
*C07H 21/00* (2006.01)
*C07K 14/00* (2006.01)

(52) U.S. Cl.
CPC ............. *C08G 61/02* (2013.01); *C07H 21/00* (2013.01); *C07K 14/003* (2013.01); *C08G 2261/128* (2013.01); *C08G 2261/143* (2013.01); *C08G 2261/3324* (2013.01); *C08G 2261/418* (2013.01)

(58) Field of Classification Search
CPC ....................................................... C08G 61/02
See application file for complete search history.

(56) References Cited

U.S. PATENT DOCUMENTS

| | | | |
|---|---|---|---|
| 4,861,760 | A | 8/1989 | Mazuel et al. |
| 4,911,920 | A | 3/1990 | Jani et al. |
| 5,034,506 | A | 7/1991 | Summerton et al. |
| 5,212,162 | A | 5/1993 | Missel et al. |
| 5,235,033 | A | 8/1993 | Summerton et al. |
| 5,403,841 | A | 4/1995 | Lang et al. |
| 5,830,658 | A | 11/1998 | Gryaznov |
| 6,306,993 | B1 | 10/2001 | Rothbard et al. |
| 9,040,626 | B2 | 5/2015 | Chien et al. |

(Continued)

FOREIGN PATENT DOCUMENTS

| | | |
|---|---|---|
| WO | WO 2016/018917 | 2/2016 |
| WO | WO 2016/023036 | 2/2016 |

OTHER PUBLICATIONS

Ilker, Tuning the Hemolytic and Antibacterial Activities of Amphiphilic Polynorbornene Derivatives, J. Am. Chem. Soc. 2004, 126, 15870-15875) (Year: 2004).*

(Continued)

*Primary Examiner* — Paul W Dickinson

(74) *Attorney, Agent, or Firm* — Leydig, Voit & Mayer, Ltd.

(57) ABSTRACT

Provided herein are compositions and methods of making high density nucleic acid polymers.

30 Claims, 29 Drawing Sheets

Specification includes a Sequence Listing.

(56) References Cited

U.S. PATENT DOCUMENTS

| | | | |
|---|---|---|---|
| 10,046,057 | B2 | 8/2018 | Tatro et al. |
| 2003/0113740 | A1 | 6/2003 | Mirkin et al. |
| 2011/0251363 | A1 | 10/2011 | Sampson et al. |
| 2012/0149843 | A1 | 6/2012 | Chien et al. |
| 2014/0105896 | A1 | 4/2014 | Cload et al. |
| 2017/0327633 | A1 | 11/2017 | Rush et al. |
| 2018/0042843 | A1 | 2/2018 | Blum et al. |
| 2020/0113934 | A1 | 4/2020 | Gianneschi et al. |

OTHER PUBLICATIONS

Johnson, Drug-Loaded, Bivalent-Bottle-Brush Polymers by Graft-through ROMP, Macromolecules, 2010, 43, 10326-10335 (Year: 2010).*
U.S. Appl. No. 15/502,166, filed Feb. 6, 2017.
U.S. Appl. No. 17/160,588, filed Jan. 28, 2021.
U.S. Appl. No. 15/329,526, filed Jan. 26, 2017.
Aldaye et al. (2008) "Assembling Materials with DNA as the Guide," Science 321(5897): 1795-1799.
Alemdaroglu et al. (2007) "DNA meets synthetic polymers—highly versatile hybrid materials," Org. Biomol. Chem. 5(9): 1311-1320.
Al-Muhammed et al. (1996) "In-vivo studies on dexamethasone sodium phosphate liposomes," J. Microencapsul. 13(3): 293-305.
Averick et al. (publicly available Apr. 2013) "Protein-polymer hybrids: Conducting ARGET ATRP from a genetically encoded cleavable ATRP initiator," Eur. Polym. J. (Oct. 2013) 49(10): 2919-2924.
Averick et al. (publicly available Jan. 2014) "Solid-Phase Incorporation of an ATRP Initiator for Polymer-DNA Biohybrids," Angew. Chem. Int. Ed. (Mar. 2014), 126(10): 2777-2782.
Bae et al. (2011) "Dendron-mediated self-assembly of highly PEGylated block copolymers: a modular nanocarrier platform," Chem. Commun. 47(37): 10302-10304.
Barish et al. (2009) "An information-bearing seed for nucleating algorithmic self-assembly," Proc. Natl. Acad. Sci. U.S.A. 106(15): 6054-6059.
Becker et al. (2003) "Peptide-polymer bioconjugates: hybrid block copolymers generated via living radical polymerizations from resin-supported peptides," Chem. Commun. 2: 180-181.
Becker et al. (2005) "Functionalized Micellar Assemblies Prepared via Block Copolymers Synthesized by Living Free Radical Polymerization upon Peptide-Loaded Resins," Biomacromolecules 6(1): 220-228.
Berge et al. (1977) "Pharmaceutical Salts," Journal of Pharmaceutical Science 66(1): 1-19.
Biagini et al. (2007) "Investigation into the ROMP copolymerization of peptide-and PEG-functionalized norbornene derivatives," J. Polym. Sci., Part A: Polym. Chem. 45(15): 3178-3190.
Blum et al. (2019) "Peptide Brush Polymers for Efficient Delivery of a Gene Editing Protein to Stem Cells," Angew. Chem. Int. Ed. 58: 15646-15649.
Blum et al. (Oct. 2014) "Peptides Displayed as High Density Brush Polymers Resist Proteolysis and Retain Bioactivity," J. Am. Chem. Soc. 136: 15422-15437.
Bolli et al. (1994) "α-Bicyclo-DNA: Synthesis, Characterization, and Pairing Properties of α-DNA-Analogues with Restricted Conformational Flexibility in the Sugar-Phosphate Backbone," Chapter 7 in Carbohydrate Modifications in Antisense Research, Sanghvi and Cook, eds. pp. 100-117.
Breaker (1997) "In Vitro Selection of Catalytic Polynucleotides," Chem. Rev. 97(2): 371-390.
Breaker et al. (1995) "Self-Incorporation of coenzymes by ribozymes," J. Mol. Evol. 40: 551-558.
Broyer et al. (2008) "Designed Amino Acid ATRP Initiators for the Synthesis of Biohybrid Materials," J. Am. Chem. Soc. 130(3): 1041-1047.
Bulte et al. (2004) "Iron oxide MR contrast agents for molecular and cellular imaging," NMR Biomed. 17(7): 484-499.

Busseron et al. (May 2013) "Supramolecular self-assemblies as functional nanomaterials," Nanoscale 5: 7098-7140.
Caliceti et al. (2003) "Pharmacokinetic and biodistribution properties of poly(ethylene glycol)—protein conjugates," Adv. Drug Delivery Rev. 55(10): 1261-1277.
Cardarelli (2011) "Quantitative Analysis of Tat Peptide Binding to Import Carriers Reveals Unconventional Nuclear Transport Properties," The Journal of Biological Chemistry 286(14): 12292-12299.
Chien et al. (2010) "Programmable Shape-Shifting Micelles," Angew. Chem., Int. Ed. 49(30): 5076-5080.
Chonn et al. (1995) "Recent advances in liposomal drug-delivery systems," Curr. Opin. Biotechnol. 6:698-708.
Conrad et al. (2009) "Tunable, Temperature-Responsive Polynorbornenes with Side Chains Based on an Elastin Peptide Sequence," Angew. Chem. Int. Edit. 48(44): 8328-8330.
Cutler et al. (2012) "Spherical Nucleic Acids," J. Am. Chem. Soc. 134(3): 1376-1391.
Darden et al. (1993) "Particle mesh Ewald: An N·log(N) method for Ewald sums in large systems," J. Chem. Phys. 98(12): 10089-10092.
Davies et al. (2001) "Synthesis of nucleic-acid base containing norbornene derivatives as monomers for ring-opening-metathesis-polymerization," J. Chem. Soc., Perkin Trans. 1 24: 3365-3381.
Davis (2002) "Non-viral gene delivery systems," Curr. Opin. Biotechnol. 13(2): 128-131.
De et al. (2008) "Temperature-Regulated Activity of Responsive Polymer-Protein Conjugates Prepared by Grafting-from via RAFT Polymerization," J. Am. Chem. Soc. 130(34): 11288-11289.
Deng et al. (2005) "DNA as Nanoscale Building Blocks," J. Nanosci. Nanotechnol. 5(12): 1954-1963.
Dietz et al. (2009) "Folding DNA into Twisted and Curved Nanoscale Shapes," Science 325(5941): 725-730.
Dubertret et al. (2001) "Single-mismatch detection using gold-quenched fluorescent oligonucleotides," Nat. Biotechnol. 19: 365-370.
Eyles et al. (1997) "Oral Delivery and Fate of Poly(lactic acid) Microsphere-encapsulated Interferon in Rats," J. Pharm. Pharmacol. 49: 669-674.
Farokhzad et al. (2004) "Nanoparticle-Aptamer Bioconjugates: A New Approach for Targeting Prostate Cancer Cells," Cancer Res. 64(21): 7668-7672.
Fraley et al. (2006) "Cationic Oligonucleotide-Peptide Conjugates with Aggregating Properties Enter Efficiently into Cells while Maintaining Hybridization Properties and Enzymatic Recognition," J. Am. Chem. Soc. 128(33): 10763-10771.
Gao et al. (1995) "Controlled Release of a Contraceptive Steroid from Biodegradable and Injectable Gel Formulations: In Vitro Evaluation," Pharm. Res. 12(6): 857-863.
Gaylord et al. (2002) "DNA detection using water-soluble conjugated polymers and peptide nucleic acid probes," Proc. Natl. Acad. Sci. U.S.A. 99(17):10954-10957.
Gibbs et al. (2005) "Polymer-DNA Hybrids as Electrochemical Probes for the Detection of DNA," J. Am. Chem. Soc. 127(4): 1170-1178.
Gibson et al. (1997) "Thymine functionalised polymers via living ring-opening metathesis polymerisation," Chem. Commun. 12: 1095-1096.
Gu et al. (2009) "Dynamic patterning programmed by DNA tiles captured on a DNA origami substrate," Nat. Nanotechnol. 4: 245-248.
Gu et al. (2010) "A proximity-based programmable DNA nanoscale assembly line," Nature 465: 202-205.
Hahn et al. (Apr. 2013) "Polymerization of a peptide-based enzyme substrate," Chem Commun (Camb) 49(28): 2873-2875 (8 pp.).
He et al. (2009) "Synthesis of Surface-Anchored DNA-Polymer Bioconjugates Using Reversible Addition-Fragmentation Chain Transfer Polymerization," Biomacromolecules 10(7): 1804-1809.
Henikoff et al. (1992) "Amino acid substitution matrices from protein blocks," Proc. Nat'l Acad. Sci. USA 89(22):10915-10919.
Herdewijn et al. (1994) "Hexopyranosyl-Like Oligonucleotides," Chapter 6 in Carbohydrate Modifications in Antisense Research, Sanghvi and Cook, eds. pp. 80-99.

(56) References Cited

OTHER PUBLICATIONS

Heredia et al. (2005) "In Situ Preparation of Protein-'Smart' Polymer Conjugates with Retention of Bioactivity," J. Am. Chem. Soc. 127(48): 16955-16960.
Hermann et al. (2000) "Adaptive Recognition by Nucleic Acid Aptamers," Science 287(5454): 820-825.
Huh et al. (2005) "In Vivo Magnetic Resonance Detection of Cancer by Using Multifunctional Magnetic Nanocrystals," J. Am. Chem. Soc. 127(35): 12387-12391.
Humphrey et al. (1996) "VMD: Visual Molecular Dynamics," J. Malec. Graphics 14: 33-38.
James et al. (Jul. 2014) "Poly(oligonucleotides)," Journal of the American Chemical Society 136: 11216-11219.
Jeong et al. (2001) "Novel Polymer-DNA Hybrid Polymeric Micelles Composed of Hydrophobic Poly(D,L-lactic-co-glycolic Acid) and Hydrophilic Oligonucleotides," Bioconjugate Chem. 12(6): 917-923.
Joyce (1994) "In vitro evolution of nucleic acids," Curr. Opin. Struct. Biol. 4(3): 331-336.
Jun et al. (2005) "Nanoscale Size Effect of Magnetic Nanocrystals and Their Utilization for Cancer Diagnosis via Magnetic Resonance Imaging," J. Am. Chem. Soc. 127(16): 5732-5733.
Kammeyer et al. (May 2013) "Polymerization of protecting-group-free peptides via ROMP," Polymer Chemistry 4(14): 3929-3933.
Kershner et al. (2009) "Placement and orientation of individual DNA shapes on lithographically patterned surfaces," Nat. Nanotechnol. 4: 557-561.
Kolpashchikov et al. (2005) "Boolean Control of Aptamer Binding States," J. Am. Chem. Soc. 127(32): 11348-11351.
Koppelhus et al. (2003) "Cellular delivery of peptide nucleic acid (PNA)," Adv. Drug Delivery Rev. 55(2): 267-280.
Ku et al. (2011) "Controlling and Switching the Morphology of Micellar Nanoparticles with Enzymes," J. Am. Chem. Soc. 133: 8392-8395.
Kwak et al. (2010) "Nucleic Acid/Organic Polymer Hybrid Materials: Synthesis, Superstructures, and Applications," Angew. Chem., Int. Ed. 49(46): 8574-8587.
Lee et al. (2009) "Polymeric ADAM Protein Mimics Interrogate Mammalian Sperm-Egg Binding," ChemBioChem 10(5): 929-937.
Lei et al. (1995) "Structure-Function Analysis of Human Glucose-6-phosphatase, the Enzyme Deficient in Glycogen Storage Disease Type 1a," J. Biol. Chem. 270(20): 11882-11886.
Leicher et al. (1998) "Coexpression of the KCNA3B Gene Product with Kv1.5 Leads to a Novel A-type Potassium Channel," J. Biol. Chem. 273(52):35095-35101.
Lele et al. (2005) "Synthesis of Uniform Protein-Polymer Conjugates," Biomacromolecules 6(6): 3380-3387.
Lesignoli et al. (2001) "Recognition and strand displacement of DNA oligonucleotides by peptide nucleic acids (PNAs): High-performance ion-exchange chromatographic analysis," J. Chromatogr. A 922(1-2) 177-185.
Liou et al. (1993) "Regulation of the NF-ηB/rel transcription factor and IηB inhibitor system," Curr. Opin. Cell Biol. 5(3): 477-487.
Lipschutz et al. (1999) "High density synthetic oligonucleotide arrays," Nat. Genet. 21: 20-24.
Liu et al. (1979) "New procedures for preparation and isolation of conjugates of proteins and a synthetic copolymer of D-amino acids and immunochemical characterization of such conjugates," Biochemistry 18(4): 690-697.
Livant et al. (2000) "The PHSRN sequence induces extracellular matrix invasion and accelerates wound healing in obese diabetic mice," J. Clin. Invest. 105(11):1537-1545.
Lockhart et al. (1996) "Expression monitoring by hybridization to high-density oligonucleotide arrays," Nat. Biotechnol. 14: 1675-1680.
Lohrmann et al. (1984) "New solid supports for DNA synthesis," DNA 3: 122-122.
Love et al. (2003) "Synthesis, Structure, and Activity of Enhanced Initiators for Olefin Metathesis," J. Am. Chem. Soc. 125(33): 10103-10109.
Lu et al. (2009) "One-Pot Synthesis of Brush-Like Polymers via Integrated Ring-Opening Metathesis Polymerization and Polymerization of Amino Acid N-Carboxyanhydrides," JACS 131(38): 13582-13583.
Lutz et al. (2005) "Preparation by controlled radical polymerization and self-assembly via base-recognition of synthetic polymers bearing complementary nucleobases," J. Polym. Sci., Part A: Polym. Chem. 43(20): 4805-4818.
Lytton-Jean et al. (2009) "Highly Cooperative Behavior of Peptide Nucleic Acid-Linked DNA-Modified Gold-Nanoparticle and Comb-Polymer Aggregates," Adv. Mater. 21(6): 706-709.
Mai et al. (2012) "Self-assembly of block copolymers," Chem. Soc. Rev. 41(18): 5969-5985.
Mammen et al. (1998) "Polyvalent Interactions in Biological Systems: Implications for Design and Use of Multivalent Ligands and Inhibitors," Angew. Chem., Int. Ed. 37(20): 2754-2794.
Matson et al. (2010) "Monotelechelic Poly(oxa)norbornenes by Ring-Opening Metathesis Polymerization using Direct End-Capping and Cross Metathesis," Macromolecules 43(1): 213-221.
Maynard et al. (2000) "Synthesis of Norbornenyl Polymers with Bioactive Oligopeptides by Ring-Opening Metathesis Polymerization, " Macromolecules 33(17):6239-6248.
McHale et al. (2012) "Nucleobase Containing Synthetic Polymers: Advancing Biomimicry via Controlled Synthesis and Self-Assembly," Macromolecules 45(19): 7665-7675.
Mihov et al. (2005) "Polyphenylene Dendrimers as Scaffolds for Shape-Persistent Multiple Peptide Conjugates," Bioconjugate Chem. 16(2): 283-293.
Mirkin et al. (1996) "A DNA-based method for rationally assembling nanoparticles into macroscopic materials," Nature 382: 607-609.
Monnard et al. (2003) "Eutectic Phase Polymerization of Activated Ribonucleotide Mixtures Yields Quasi-Equimolar Incorporation of Purine and Pyrimidine Nucleobases," J. Am. Chem. Soc. 125(45): 13734-13740.
Needleman et al. (1970) "A general method applicable to the search for similarities in the amino acid sequence of two proteins," J. Mol. Biol. 48: 443-453.
Nielsen et al. (1991) "Sequence-selective recognition of DNA by strand displacement with a thymine-substituted polyamide," Science 254(5037): 1497-1500, (Machine Generated Copy).
Nomura et al. (1996) "Preparation of 'Sugar-Coated' Homopolymers and Multiblock ROMP Copolymers," Macromolecules 29(2): 540-545.
Orum et al. (1993) "Single base pair mutation analysis by PNA directed PCR clamping," Nucleic Acids Res. 21(23): 5332-5336.
Ostro et al. (1989) "Use of liposomes as injectable-drug delivery systems," Am. J. Hosp. Pharm. 46: 1576-1587.
Park et al. (2008) "DNA-programmable nanoparticle crystallization," Nature 451: 553-556.
Patil et al. (2005) "DNA-based therapeutics and DNA delivery systems: A comprehensive review," AAPS J. 7(1): E61-E77.
Pearson et al. (1988) "Improved tools for biological sequence comparison," Proc. Nat'l. Acad. Sci. USA 85(8):2444-2448.
Phillips et al. (2005) "Scalable molecular dynamics with NAMD," Journal of Computational Chemistry 26(16): 1781-1802.
Pianowski et al. (2008) "Nucleic acid encoding to program self-assembly in chemical biology," Chem. Soc. Rev. 37(7): 1330-1336.
Pohl et al. (1999) "Scope of Multivalent Ligand Function: Lactose-Bearing Neoglycopolymers By Ring-Opening Metathesis Polymerization," Synthesis 1999(SI): 1515-1519.
Pooga et al. (1998) "Cell penetrating PNA constructs regulate galanin receptor levels and modify pain transmission in vivo," Nat. Biotechnol. 16: 857-861.
Rankin et al. (2007) "The controlled homogeneous organic solution polymerization of new hydrophilic cationic exo-7-oxanorbornenes via ROMP with RuCl2(PCy3)2CHPh in a novel 2,2,2-trifluoroethanol/methylenechloride solvent mixture," J. Polym. Sci. A Polym. Chem. 45(11): 2113-2128.
Rao (1995) "Recent developments of collagen-based materials for medical applications and drug delivery systems," J. Biomater Sci. Polym. Ed. 7(7): 623-645.

(56) References Cited

OTHER PUBLICATIONS

Reissmann et al. (2000) "The LHRH antagonist Cetrorelix: a review," Human Reproduction Update 6(4): 322-331.
Rosi et al. (2006) "Oligonucleotide-Modified Gold Nanoparticles for Intracellular Gene Regulation," Science 312(5776): 1027-1030.
ROTHEMUND (2006) "Folding DNA to create nanoscale shapes and patterns," Nature 440: 297-302.
Rush et al. (May 2014) "Intracellular mRNA Regulation with Self-Assembled Locked Nucleic Acid Polymer Nanoparticles," J. Am. Chem. Soc. 136: 7615-7618.
Saiki (1985) "Enzymatic amplification of beta-globin genomic sequences and restriction site analysis for diagnosis of sickle cell anemia," Science 230(4732): 1350-1354, (Machine Generated Copy).
Sanford et al. (2001) "A Versatile Precursor for the Synthesis of New Ruthenium Olefin Metathesis Catalysts," Organometallics 20(25): 5314-5318.
Search Report and Written Opinion, dated Feb. 16, 2016, corresponding to International Application No. PCT/US2015/042482, 15 pp.
Search Report and Written Opinion, dated Nov. 27, 2015, corresponding to International Application No. PCT/US2015/044515, 8 pp.
SEEMAN (2010) "Structural DNA Nanotechnology: Growing Along with Nano Letters," Nano Lett. 10(6): 1971-1978.
Smith et al. (1981) "Comparison of Biosequences," Adv. Appl. Math. 2:482-489.
Spijker et al. (2007) "Atom Transfer Radical Polymerization of Adenine, Thymine, Cytosine, and Guanine Nucleobase Monomers," Macromolecules 40(1): 12-18.
Storhoff et al. (1999) "Programmed Materials Synthesis with DNA," Chem. Rev. 99(7): 1849-1862.
Sumerlin (2012) "Proteins as Initiators of Controlled Radical Polymerization: Grafting-from via ATRP and RAFT," ACS Macro Lett. 1: 141-145.
Sutthasupa et al. (2010) "Recent advances in ring-opening metathesis polymerization, and application to synthesis of functional materials," Polymer Journal 42: 905-915.
Thompson et al. (publicly available Dec. 2013) "Labelling Polymers and Micellar Nanoparticles via Initiation, Propagation and Termination with ROMP," Polym Chem, Mar. 2014 5(6):1954-1964.
Thundimadathil (Dec. 2012) "Cancer Treatment Using Peptides: Current Therapies and Future Prospects," Journal of Amino Acids 2012(967347): 1-13.
Tijssen (1993) "Overview of principles of hybridization and the strategy of nucleic acid probe assays," in Techniques in Biochemistry and Molecular Biology—Hybridization with Nucleic Probes, 19-78.
Toti et al. (2010) "Interfacial Activity Assisted Surface Functionalization: A Novel Approach To Incorporate Maleimide Functional Groups and cRGD Peptide on Polymeric Nanoparticles for Targeted Drug Delivery," Mol Pharm. 7(4): 1108-1117.
Tyagi et al. (1996) "Molecular Beacons: Probes that Fluoresce upon Hybridization," Nat. Biotechnol. 14: 303-308.
Tymoczko ed. (2010) Biochemistry: A Short Course, 2nd ed., W.H. Freeman and Company: 13-15.
US Office Action, dated Jan. 30, 2020, in U.S. Appl. No. 15/502,166, 19 pp.
US Office Action, dated Jun. 12, 2020, in U.S. Appl. No. 15/502,166, 23 pp.
US Office Action, dated Jun. 19, 2019, in U.S. Appl. No. 15/502,166, 7 pp.
US Office Action, dated Sep. 14, 2020, in U.S. Appl. No. 15/502,166, 18 pp.
Vanommeslaeghe et al. (2010) "CHARMM general force field: A force field for drug-like molecules compatible with the CHARMM all-atom additive biological force fields," J. Comput. Chem. 31(4): 671-690.
Vanommeslaeghe et al. (2012) "Automation of the CHARMM General Force Field (CGenFF) I: Bond Perception and Atom Typing," J. Chem. Inf. Model. 52(12): 3144-3154.
Vanommeslaeghe et al. (2012) "Automation of the CHARMM General Force Field (CGenFF) II: Assignment of Bonded Parameters and Partial Atomic Charges," J. Chem. Inf Model. 52(12): 3155-3168.
Vukovic et al. (2011) "Structure and Dynamics of Highly PEGylated Sterically Stabilized Micelles in Aqueous Media," J. Am. Chem. Soc. 133(34): 13481-13488.
Vukovic et al. (Nov. 2013) "Solubilization of Therapeutic Agents in Micellar Nanomedicines," Langmuir 29(51): 15747-15754.
Wilson et al. (1991) "Restriction and Modification Systems," Annu. Rev. Genet. 25: 585-627.
Zilong et al. (publicly available Jun. 2013) "A Controlled-Release Nanocarrier with Extracellular pH Value Driven Tumor Targeting and Translocation for Drug Delivery," Angew. Chem., Int. Ed. (Jul. 2013), 52(29): 7487-7491.

* cited by examiner

FIG. 3A
FIG. 3B
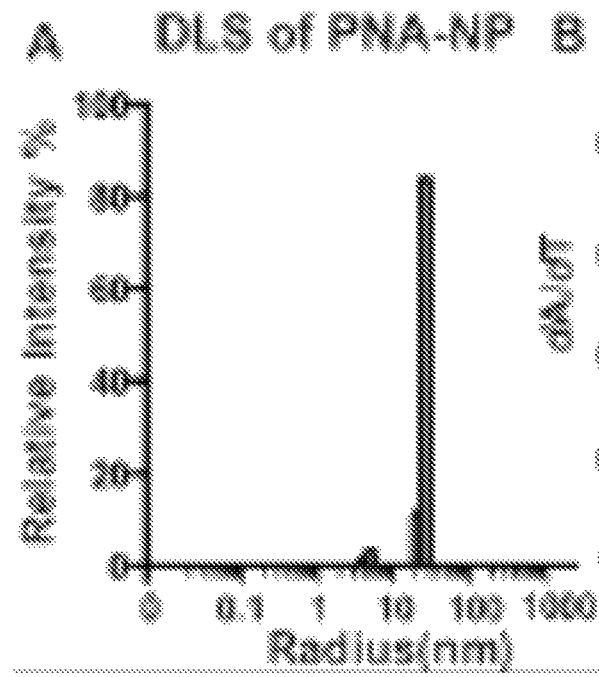
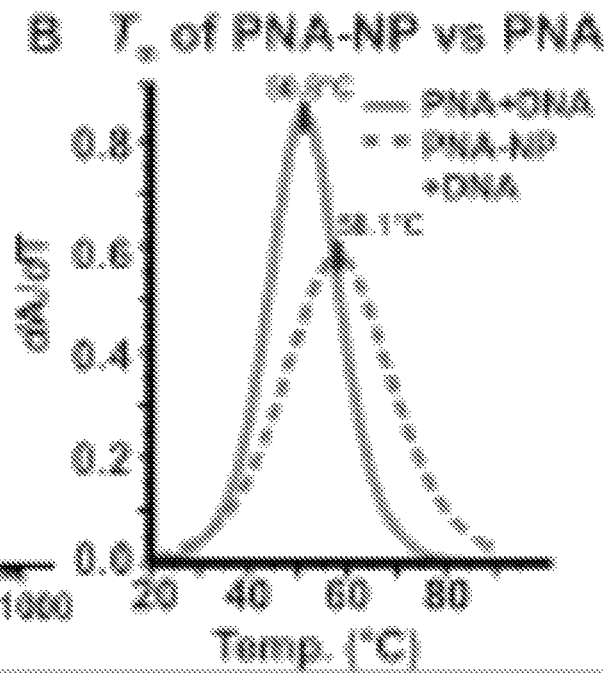
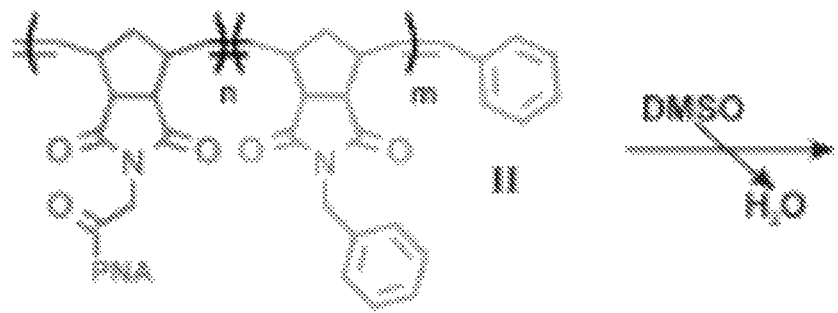

FIG. 4A
FIG. 4B
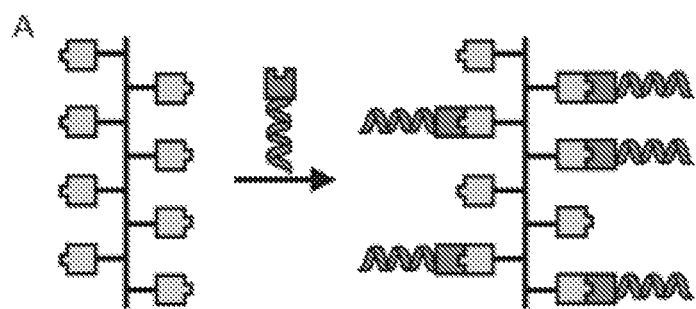
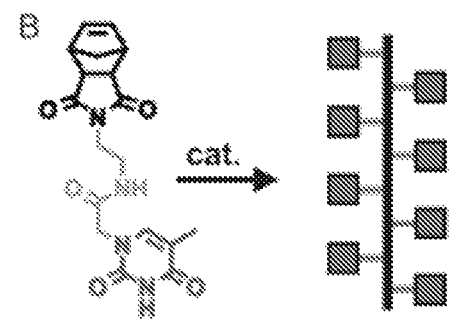

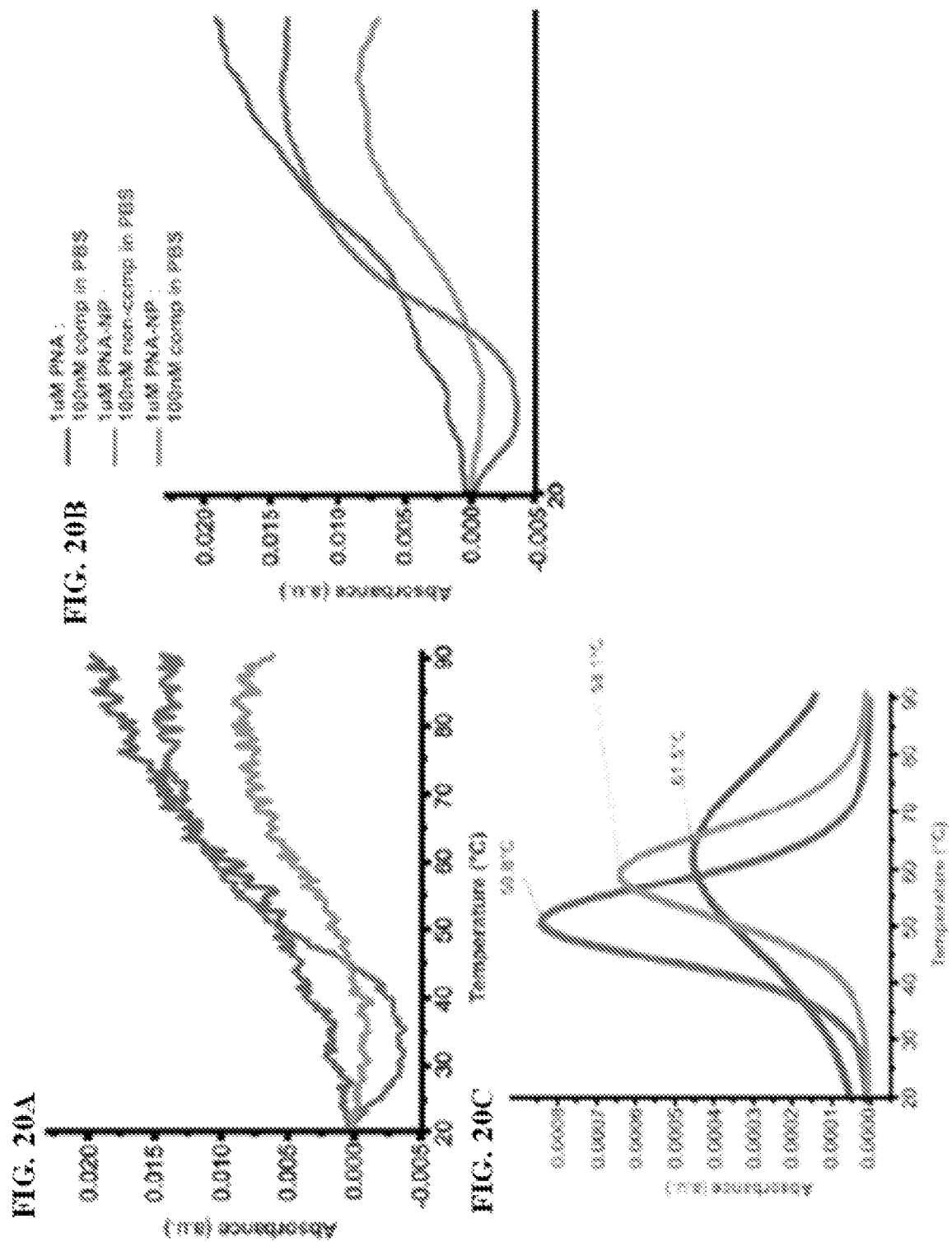

Partial Charges on Adenine Base in PNA

| Atom Label | Atom Name | Partial Atomic Charge |
|---|---|---|
| C1 | CR64 | 0.499754 |
| C2 | CRC0 | 0.432754 |
| C3 | CRC0 | 0.280754 |
| C4 | CR64 | 0.456754 |
| C5 | CR53 | 0.345754 |
| N1 | NR62 | -0.741245 |
| N2 | NR62 | -0.748245 |
| N3 | NR50 | -0.709245 |
| N4 | NR51 | -0.072245 |
| N5 | N2S3 | -0.769245 |
| H1 | HR62 | 0.126754 |
| H2 | HGP4 | 0.378754 |
| H3 | HGP4 | 0.378754 |
| H4 | HR52 | 0.140193 |

Guanine:

Partial Charges of Guanine Base in PNA

| Atom Label | Atom Name | Partial Atomic Charge |
|---|---|---|
| C1 | CR64 | 0.750754 |
| C2 | CRC0 | 0.269754 |
| C3 | CRC0 | 0.004754 |
| C4 | CR63 | 0.538754 |
| C5 | CR53 | 0.258754 |
| N1 | NR61 | -0.341245 |
| N2 | NR62 | -0.735245 |
| N3 | NR50 | -0.599245 |
| N4 | NR51 | -0.038245 |
| N5 | N2S3 | -0.677245 |
| O1 | O2D4 | -0.508245 |
| H1 | HGP1 | 0.262754 |
| H2 | HGP4 | 0.336754 |
| H3 | HGP4 | 0.336754 |
| H4 | HR52 | 0.140438 |

Thymine:

Partial Charges for Thymine Base in PNA

| Atom Label | Atom Name | Partial Atomic Charge |
|---|---|---|
| C1 | CR63 | 0.515142 |
| C2 | CR63 | 0.516142 |
| C3 | CR62 | -0.127856 |
| C4 | CR62 | 0.181142 |
| C5 | C331 | -0.153856 |
| N1 | NR61 | -0.350856 |
| N2 | NR61 | -0.443856 |
| O1 | O2D4 | -0.392856 |
| O2 | O2D4 | -0.432856 |
| H1 | HR62 | 0.181142 |
| H2 | HR62 | 0.187142 |
| H3 | HGA3 | 0.107142 |
| H4 | HGA3 | 0.107142 |
| H5 | HGA3 | 0.107142 |

Cytosine:

Partial Charges of Cytosine Base in PNA

| Atom Label | Atom Name | Partial Atomic Charge |
|---|---|---|
| C1 | CR63 | 0.499754 |
| C2 | CR64 | 0.647754 |
| C3 | CR62 | -0.084298 |
| C4 | CR62 | 0.049754 |
| N1 | NR61 | -0.163245 |
| N2 | NR62 | -0.660245 |
| N3 | N2S3 | -0.748245 |
| O1 | O2D4 | -0.480245 |
| H1 | HR62 | 0.169754 |
| H2 | HR62 | 0.069754 |
| H3 | HGP4 | 0.349754 |
| H4 | HGP4 | 0.349754 |

Peptide Chain Unit:

Partial Charges for a Unit of the Peptide Chain in PNA

| Atom Label | Atom Name | Partial Atomic Charge |
|---|---|---|
| C1 | C321 | -0.052245 |
| C2 | C321 | 0.040754 |
| C3 | C321 | 0.019754 |
| C4 | C201 | 0.530754 |
| C5 | C201 | 0.415754 |
| C6 | C321 | -0.037245 |
| N1 | N2S1 | -0.442245 |
| N2 | N2S0 | -0.415245 |
| O1 | O2D1 | -0.510245 |
| O2 | O2D1 | -0.533245 |
| H1 | HGP1 | 0.265422 |
| H2 | HGA2 | 0.089754 |
| H3 | HGA2 | 0.089754 |
| H4 | HGA2 | 0.089754 |
| H5 | HGA2 | 0.089754 |
| H6 | HGA2 | 0.089754 |
| H7 | HGA2 | 0.089754 |
| H8 | HGA2 | 0.089754 |
| H9 | HGA2 | 0.089754 |

Hydrophobic Unit:

Partial Charges for a Unit of the Hydrophobic Chain

| Atom Label | Atom Name | Partial Atomic Charge |
|---|---|---|
| C1 | CG2D | -0.124833 |
| C2 | CG3C | -0.112833 |
| C3 | CG3C | -0.174833 |
| C4 | CG3C | -0.193833 |
| C5 | CG2D | -0.124833 |
| C6 | CG3R | 0.068166 |
| C7 | CG3R | 0.085166 |
| C8 | CG2R | 0.327666 |
| C9 | CG2R | 0.327666 |
| C10 | CG32 | -0.014833 |
| C11 | CG2R | -0.015833 |
| C12 | CG2R | -0.113833 |
| C13 | CG2R | -0.105833 |
| C14 | CG2R | -0.110833 |
| C15 | CG2R | -0.105833 |
| C16 | CG2R | -0.113833 |
| N1 | NG2R | -0.126833 |
| O1 | OG2D | -0.508333 |
| O2 | OG2D | -0.508333 |
| H1 | HGA4 | 0.154166 |
| H2 | HGA1 | 0.094166 |
| H3 | HGA2 | 0.094166 |
| H4 | HGA2 | 0.094166 |
| H5 | HGA2 | 0.094166 |
| H6 | HGA5 | 0.169507 |
| H7 | HGA1 | 0.094166 |
| H8 | HGA1 | 0.094166 |
| H9 | HGA2 | 0.094166 |
| H10 | HGA2 | 0.094166 |
| H11 | HGR6 | 0.113966 |
| H12 | HGR6 | 0.113966 |
| H13 | HGR6 | 0.113966 |
| H14 | HGR6 | 0.113966 |
| H15 | HGR6 | 0.113966 |

COMPOSITIONS AND METHODS OF MAKING POLYMERIZED NUCLEIC ACIDS

CROSS-REFERENCES TO RELATED APPLICATIONS

This application is a continuation application of U.S. patent application Ser. No. 15/329,526, filed Jan. 26, 2017, which is a U.S. National Stage Application filed under 35 U.S.C. § 371 of International Patent Application No. PCT/US2015/042482, filed Jul. 28, 2015; which claims the benefit of and priority to U.S. Provisional Patent Application, 62/029,833, filed Jul. 28, 2014. The disclosures of each of the prior applications is incorporated herein by reference in their entireties.

STATEMENT AS TO RIGHTS TO INVENTIONS MADE UNDER FEDERALLY SPONSORED RESEARCH AND DEVELOPMENT

This invention was made with government support under grant number W91INF- 14-1-0169 awarded by the Department of Defense. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file "338718 ST25", created on May 13, 2021, 607 bytes, containing SEQ ID No. 1, is hereby incorporated by reference.

BACKGROUND IDC-B1

Structures containing nucleic acids decorating surfaces, particles and polymers can be made. There is evidence that the density of nucleic acids in such arrays imparts special, highly unusual and unique properties on the nucleic acids. Unfortunately, in the case of polymeric chemistry, high densities have not been achieved because all techniques rely on post-polymerization modification (conjugation) of relatively high molecular weight polymers to relatively high molecular weight nucleic acids. There is a need for methods for generating a nucleic acid polymer wherein every single position of the polymer backbone is a nucleic acid as a monomer. The present invention provides this need and provides related advantages as well.

BRIEF SUMMARY

The present invention is based, in part, on the discovery of a novel composition of a polymer, e.g., brush polymer, wherein every position of the polymer backbone contains a nucleic acid as a monomer. The composition serves as an informationally encoded synthetic system with an ultra high density of nucleic acids. Also provided herein are methods for synthesizing the poly(oligonucleotide).

This is the first example of a nucleic acid-based polymer material with a high density of nucleic acids such that each position contains a nucleic acid. Such a material can be used as a nucleic acid delivery vehicle, a sensor, a probe, or functional nucleic acid-based material for other applications, such as for medicine and advanced materials. Potential applications include the facile preparation of materials for affinity purification of DNA, gene and nucleic acid delivery to cells, and in the development of materials capable of programming self-assembly.

The nucleic acid-based polymer material possesses novel properties including nanomaterial formation and DNA-binding.

The poly(oligonucleotide) material described herein is entirely different from post-polymerization modified polymeric materials and/or nanoparticle-DNA conjugates and/or DNA-surface conjugates of any other kind (e.g. graft-onto polymerization). Other examples of nucleic acid-based material involves first preparing a template, and then modifying that template. This, due to thermodynamics and kinetics, results in a less than optimized density of nucleic acid, and it is the density of the array that gives unique properties including high binding affinities and nuclease resistance (a general resistance to degradation that plagues almost every type of formulation of nucleic acid). Protecting from degradation and packaging nucleic acids such that they retain biological function is a key requirement in medicines related to nucleic acid based technologies. The discovery of nucleic acid-based polymers by the inventors has solved these and other problems.

In one aspect, provided herein is a synthetic nucleic acid polymer composition including a plurality of nucleic acid monomers and a polymer backbone, wherein each position of the backbone contains a nucleic acid monomer. Each nucleic acid monomer can include a natural or an unnatural nucleic acid. In some instances, the nucleic acid is RNA, DNA, PNA, LNA or any combination thereof. Each nucleic acid monomer can include at least 5 nucleic acids or more. Each nucleic acid monomer can include at least 10 nucleic acids or more. The nucleic acid composition can have a degree of polymerization of at least 5 or more. The compositions can be in the form of a brush polymer. In some embodiments, the composition can be in the form of a micelle. Alternatively, the compositions can be in the form of a nanoparticle.

In a second aspect, provided herein is a method for or generating a synthetic nucleic acid polymer composition comprising a plurality of nucleic acid monomers and a polymer backbone, wherein each position of the backbone contains a nucleic acid monomer, the method comprising graft-through polymerizing a plurality of nucleic acid monomers. The step of polymerizing can include using a ROMP initiator. In some embodiments, the composition has a degree of polymerization of at least 5 or more.

In an aspect is provided a graft polymer including a linear backbone covalently bound to a plurality of oligonucleotide branches. The graft polymer is assembled by graft-through polymerization of a plurality of oligonucleotide monomers including a polymerizable monomer covalently bound to an oligonucleotide. The oligonucleotide thereby forms each of the plurality of oligonucleotide branches.

In an aspect is provided a block graft copolymer including a linear backbone covalently bound to a plurality of oligonucleotide branches and a plurality of non-oligonucleotide side chains, wherein: the plurality of oligonucleotide branches form a first block portion of the graft copolymer and the non-oligonucleotide side chains form a second block portion of the graft copolymer; the graft copolymer is assembled by graft-through polymerization of a plurality of oligonucleotide monomers and a plurality of non-oligonucleotide monomers, wherein each of the plurality of oligonucleotide monomers includes a polymerizable monomer covalently bound to an oligonucleotide, the oligonucleotide thereby forming each of the plurality of oligonucleotide branches; and each of the plurality of non-oligonucleotide monomers includes the polymerizable monomer covalently bound to a non-oligonucleotide moiety, the non-oligonucleotide moiety thereby forming each of the plurality of non-oligonucleotide side chains.

In an aspect is provided an amphiphilic block graft copolymer including a linear backbone covalently bound to a plurality of oligonucleotide branches and a plurality of hydrophobic side chains, wherein: the plurality of oligonucleotide branches form a hydrophilic block portion of the amphiphilic graft copolymer and the hydrophobic side chains form a hydrophobic block portion of the amphiphilic graft copolymer; the graft copolymer is assembled by graft-through polymerization of a plurality of oligonucleotide monomers and a plurality of hydrophobic monomers, wherein each of the plurality of oligonucleotide monomers includes a polymerizable monomer covalently bound to an oligonucleotide, the oligonucleotide thereby forming each of the plurality of oligonucleotide branches; and each of the plurality of hydrophobic monomers includes the polymerizable monomer covalently bound to a hydrophobic moiety, the hydrophobic moiety thereby forming each of the plurality of hydrophobic side chains.

In an aspect is provided a micelle including an amphiphilic block graft copolymer described herein, including in an aspect, embodiment, example, figures, table, scheme, or claim as provided herein.

In an aspect is provided a nanoparticle including an amphiphilic block graft copolymer described herein, including in an aspect, embodiment, example, figure, table, scheme, or claim as provided herein.

In an aspect is provided a method of making a graft polymer, the method including: (i) reacting a plurality of oligonucleotide monomers with a polymerization catalyst or initiator, wherein each of the plurality of oligonucleotide monomers includes a polymerizable monomer covalently bound to an oligonucleotide; and (ii) terminating the reacting with a chain terminator or transfer agent.

In an aspect is provided a method of making an amphiphilic block graft copolymer, the method including: (i) reacting a plurality of oligonucleotide monomers with a polymerization catalyst thereby forming a hydrophilic block portion, wherein each of the plurality of oligonucleotide monomers includes a polymerizable monomer covalently bound to an oligonucleotide; (ii) reacting the hydrophilic block portion with a plurality of hydrophobic monomers and the polymerization catalyst thereby forming the amphiphilic block graft copolymer, wherein each of the plurality of hydrophobic monomers includes the polymerizable monomer covalently bound to a hydrophobic moiety.

In an aspect is provided a method of making an amphiphilic block graft copolymer, the method including: (i) reacting a plurality of hydrophobic monomers with a polymerization catalyst thereby forming a hydrophobic block portion, wherein each of the plurality of hydrophobic monomers includes a polymerizable monomer covalently bound to a hydrophobic moiety; (ii) reacting the hydrophobic block portion with a plurality of oligonucleotide monomers and the polymerization catalyst thereby forming the amphiphilic block graft copolymer, wherein each of the plurality of oligonucleotide monomers includes the polymerizable monomer covalently bound to an oligonucleotide.

Other objects, features, and advantages of the present invention will be apparent to one of skill in the art from the following detailed description and figures.

BRIEF DESCRIPTION OF THE DRAWINGS

FIG. 1A: PNA-norbornyl monomer (PNA-Nb) polymerized using ROMP initiator (IMesH$_2$)(C$_5$H$_5$N)$_2$(Cl)$_2$Ru=CHPh ("Ru") to form poly-PNA homopolymer, I, and poly-PNA block copolymer, II. FIG. 1B: Representative percent conversion for I determined by the disappearance of the olefin signal associated with PNA-Nb in lHNMR. FIG. 1C: Representative SEC-MALS for II. $M_n$=28,270 indicating a degree of polymerization of 5 for the PNA block.

FIGS. 3A-3E show that poly-PNA amphiphile II was dialyzed from DMSO into H$_2$O to generate nanoparticles. FIG. 3A: DLS data indicating a hydrodynamic radius of 25 nm. FIG. 3B: $T_m$ of PNA-NP with a complementary DNA sequence was found to be 58. 1° C. FIG. 3C: Negative-stained TEM of PNA-NP provided evidence of spherical 20 nm diameter nanoparticles. Sequence legend: GCTCAGTAAA (SEQ ID NO: 1). Atomistic models of (FIG. 3D) II and (FIG. 3E) PNA-NP. II is shown in a conformation present within PNA-NP.

FIGS. 4A-4B provide Scheme 1 which shows known methods for the incorporation of multiple nucleic acids of nucleobases into polymers. FIG. 4A shows Post-polymerization modification of a polymer with a nucleic acid.[51-53] FIG. 4B: Polymerization of a pyrimidine base as a modified monomer.[44-50]

FIGS. 15A-14B. SEC-MALS of (FIG. 15A) homophenyl block as well as (FIG. 15B) SEC-MALS of VIII.

FIGS. 20A-20C. Raw Tm data for PNA-NP and complementary DNA, as well as non-complementary DNA sequence.

FIGS. 2 1A-2 IB. Raw Tm data for PNA-NP without complementary DNA and complementary DNA without PNA in PBS.

DETAILED DESCRIPTION OF THE INVENTION

Figure 1A:
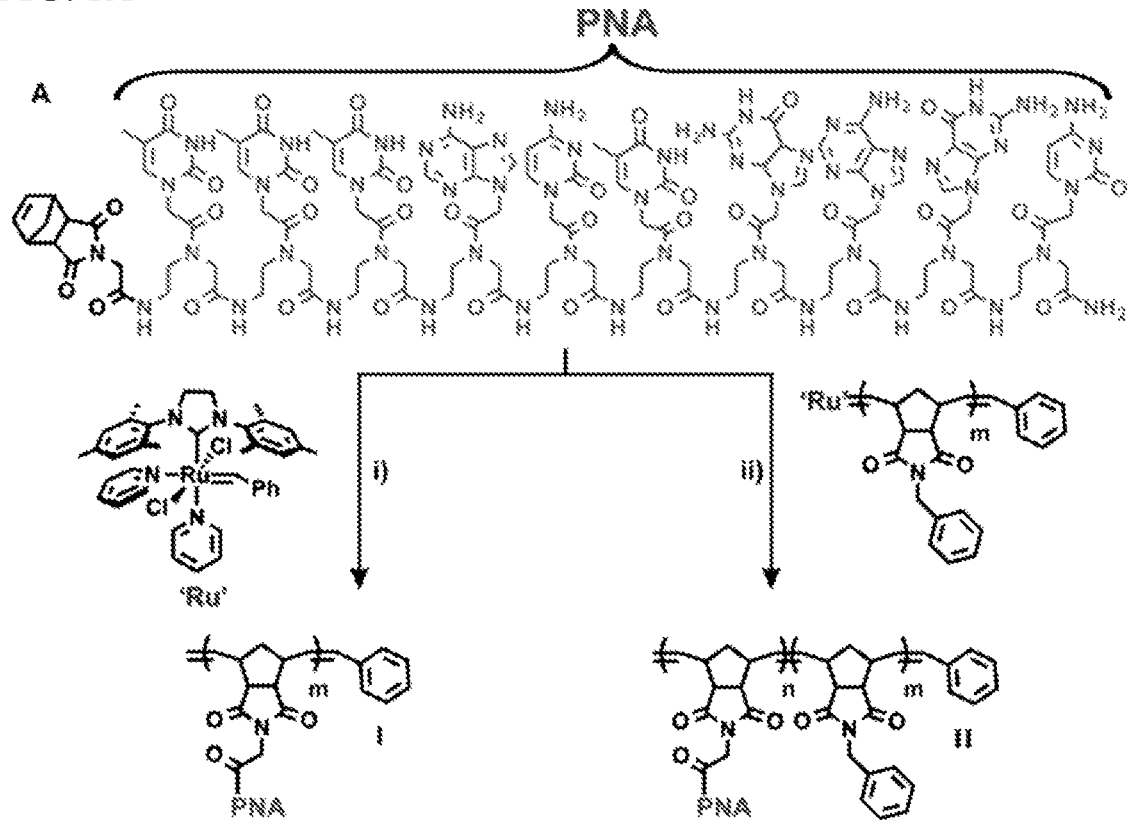
FIGS. 1A-1C show synthesis and characterization of a poly(oligonucleotide).

In embodiments, the inventors have, inter alia, avoided shortcomings associated with post-polymerization modification reactions (e.g. graft-onto polymerization) and have developed nucleic acid brush polymers and amphiphilic brush copolymers by direct polymerization via graft-through polymerization of a nucleic acid. Provided herein is the first example of a polymer-nucleic acid bioconjugate generated via direct polymerization of an oligonucleotide monomer. In addition, these materials show cooperative hybridization to complementary DNA oligonucleotides.

In embodiments, the methods described herein provide an efficient synthetic strategy for the incorporation of nucleic acids into particle and polymer-based materials, with potential applications including the facile preparation of materials for affinity purification of DNA, gene and nucleic acid delivery to cells, and in the development of materials capable of programmed self-assembly. In embodiments, the covalent incorporation (direct polymerization or graft-through) of peptide nucleic acids into polymer-based nanomaterials could facilitate cellular internalization of nucleic acid sequences that could then be capable of regulating mRNA levels in live human cells, while maintaining the enzymatic resistance of non-naturally occurring PNAs. In embodiments, this could occur through gene interference and/or genetically guided or enhanced theranostics.

I. Definitions

The term "nucleic acid polymer" or "poly(oligonucleotide)" refers to a true polymer of oligonucleotides that contains a polymer backbone with a nucleic acid as a monomer at every position of the backbone (i.e., an oligonucleotide (e.g., PNA) connected at one end of the oligonucleotide to the polymer monomer moiety). In embodiments, a "poly(oligonucleotide)" is a polymer of norbornyl monomer-oligonucleotides (e.g., 2-1000-mers) forming a brush polymer where each branch is an oligonucleotide (e.g., 2-1000-mer). The term includes any polymerized nucleic acid containing material generated through direct polymerization of monomers including a nucleic acid.

The term "nucleic acid" includes at least two nucleotides (e.g., natural and/or synthetic). The nucleotide can include RNA, DNA, PNA, LNA, and other modified natural or unnatural formulations of a nucleotide. The term "nucleotide" as used herein refers to a single nucleotide, and the terms "nucleic acid," "polynucleotide," and "oligonucleotide" refer to the plural thereof.

The term "nucleobase" is used in accordance with its meaning in molecular biology and genetics and refers to a nitrogen-containing biological compound (nitrogenous base) that may be linked to a polymer backbone (e.g. an amide backbone as in peptide nucleic acids or a sugar within nucleosides as in DNA and RNA. The nitrogenous bases are well-known in the art and include, for example the naturally occurring cytosine, guanine, adenine, thymine, uracil as well as natural and non-natural derivatives thereof. In embodiments, to the nitrogenous base is cytosine, guanine, adenine, thymine, or uracil. In embodiments, the nitrogenous base is hypoxanthine, xanthine, 7-methylguanine, 5,6-dihydrouracil, 5-methylcytosine, and/or 5-hydroxymethylcytosine. In embodiments, the nucleobase is attached to a detectable moiety. In embodiments, the nucleobase includes an isomer of a naturally occurring nitrogenous base such as isoguanine or isocytosine. In embodiments, nucleobases are linked through a nucleic acid backbone such as a DNA or RNA backbone or peptide nucleic acid backbone. Internucleotide linkages may include one or more of phosphodiester, phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, amide and/or O-methylphosphoroamidite linkages.

The term "nucleic acid monomer" refers to a monomelic unit (e.g., single unpolymerized precursor to a polymer or single repeated unit within a polymer (where each repeated unit is identical within the length of the polymer but may vary in sidechains (e.g., branches) connected to the repeated unity) containing more than one nucleotide joined by one or more bonds.

The term "degree of polymerization" refers to the number of monomelic units in a polymer molecule.

The abbreviations used herein have their conventional meaning within the chemical and biological arts. The chemical structures and formulae set forth herein are constructed according to the standard rules of chemical valency known in the chemical arts.

The term "graft-through polymerization" is used in accordance with its plain meaning in the art of polymer chemistry and refers to a macromonomer method of graft polymer (e.g., polymer or copolymer) synthesis. The method forms the graft polymer (also referred to in the polymer chemistry arts as the macromolecule) by polymerizing macromonomer molecules having one polymerizable monomer end-group which enables it to act as a monomer molecule, contributing a single monomeric unit to a chain of the final macromolecule (graft polymer). Unlike graft polymers assembled by graft-to (also commonly referred to as "graft-onto") polymerization, graft polymers assembled by graft-through polymerization do not include unreacted functional groups (or chemical vestiges thereof) within the linear backbone used to graft side chain polymers to the linear backbone. Graft-through polymerization includes methods of polymerization for synthesizing a polymer with monomer side chains (e.g., nucleic acids) using a known polymerization strategy amenable to the functional groups involved, including protected and unprotected forms. Graft-through polymerization may include synthesizing a polymer with monomer side chains (e.g., nucleic acid monomers) wherein the monomer side chains are not further derivatized or modified after synthesis of the polymer. Thus, graft polymers assembled by graft-through polymerization include high density polymers having smaller distances between side chains relative to graft polymers assembled by graft-to polymerization. In embodiments, the graft polymer is a brush polymer. In embodiments, the graft polymer synthesis is a brush polymer synthesis. In embodiments, the graft-through polymerization employs atom transfer radical polymerization (ATRP), ring-opening metathesis polymerization (ROMP), anionic and cationic polymerizations, free radical living polymerization, radiation-induced polymerization, ring-opening olefin metathesis polymerization, polycondensation reactions, or iniferter-induced polymerization.

The term "brush polymer" is used in accordance with its meaning in the art of polymer chemistry and refers to a layer of polymers (e.g., sidechains, oligonucleotides) attached with one end to a common support (e.g., polymer, linear polymer, surface) The brush polymer may be characterized by the high density of grafted chains (e.g. oligonucleotides, sidechains). The limited space may lead to a strong extension of the chains and unique properties of the system.

The term "polymerizable monomer" is used in accordance with its meaning in the art of polymer chemistry and refers to a compound that may covalently bind chemically to other monomer molecules to form a polymer. An example of a polymerizable monomer is a ROMP polymerizable monomer, which is a polymerizable monomer capable of binding chemically to other ROMP polymerizable monomers through a ROMP chemical reaction to form a polymer. It will be understood that a polymerizable monomer may be chemically modified in the polymerization reaction to differ from the free polymerizable monomer when forming the polymerizable monomer moiety. In embodiments, the ROMP polymerizable monomer includes an olefin. In embodiments, the ROMP polymerizable monomer includes a cyclic olefin. In embodiments, the ROMP polymerizable monomer includes a cyclic olefin with ring strain (e.g., norbornene or cyclopentene or derivatives thereof). In embodiments, the ROMP polymerizable monomer includes an oligonucleotide. In embodiments, the ROMP polymerizable monomer includes a hydrophobic moiety. In embodiments, the ROMP polymerizable monomer includes substituted or unsubstituted norbornenyl (a monovalent substituted or unsubstituted norbornene).

In embodiments, the ROMP polymerizable monomer is

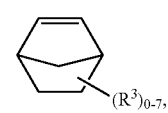
(IA)

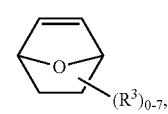
(IB)

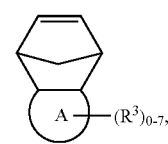
(IC)

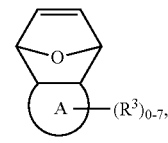
(ID)

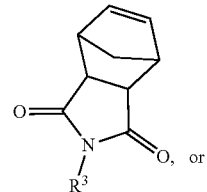
(IE)

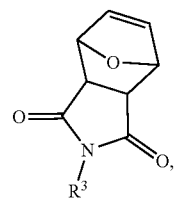
(IF)

wherein Ring A is substituted or unsubstituted cycloalkyl, substituted or unsubstituted heterocycloalkyl, substituted or unsubstituted aryl, or substituted or unsubstituted heteroaryl; $R^3$ is independently an oligonucleotide, hydrogen, halogen, oxo, —C(halo)3, —CH(halo)2, $CH_2$(halo), —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently an oligonucleotide. In embodiments, at least one $R^3$ is independently an oligonucleotide. In embodiments, $R^3$ is independently a halogen, oxo, —C(halo)$_3$, —CH(halo)$_2$, —$CH_2$(halo), —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, at least one $R^3$ is independently an oligonucleotide. In embodiments, $R^3$ is independently a hydrogen, halogen, oxo, —C(halo)$_3$, —CH(halo)$_2$, —$CH_2$(halo), —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the ROMP polymerizable monomer is

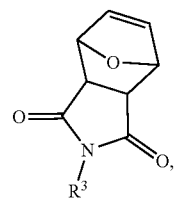
(IIIA)

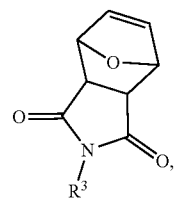
(IIIB)

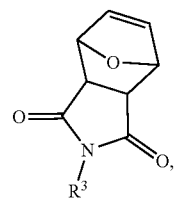
(IIIC)

-continued

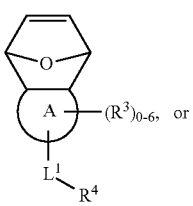
(IIID)

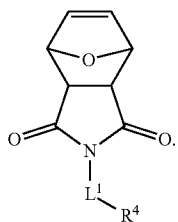
(IIIE)

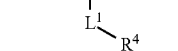
or

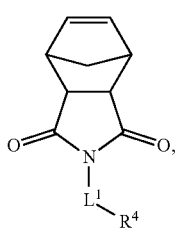
(IIIF)

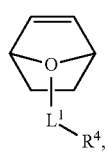

In formula (IIA-IIF), Ring A, $L^1$, $R^3$ and $R^4$ are as defined herein. In embodiments of formula (IIA)-(IIF), $R^3$ is not an oligonucleotide. In embodiments, the ROMP polymerizable monomer is (IIIA)

(IIIB)

(IIIC)

(IIID)

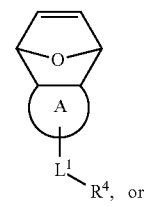
(IIIE)

(IIIF)

In formula (IIIA)-(IIIF), Ring A, $L^1$ and $R^4$ is as defined herein.

$L^1$ is independently a bond, —O—, —NFL, —COO—, —S—, —SO$_2$—, —SO$_3$—, —SO$_4$—, —SO$_2$NH—, —NHC(O)—, —C(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^1$ is independently a bond, —C(O)O—, —C(O)NH—, —C(O)NHCH$_2$CH$_2$NH—, —CH$_2$—, —CH$_2$CH$_2$O—, —CH$_2$CH$_2$—, —CH$_2$NHC(O)—, —CH$_2$CH$_2$NHC(O)—, —CH$_2$CH$_2$NH—, —CH$_2$O—, —CH$_2$CH$_2$N(CH$_3$)$_2$CH$_2$—, —CH$_2$C(O)—, or —CH$_2$CH$_2$C(O)—. In embodiments, $L^1$ is independently —C(O)O—, —C(O)NH—, —C(O)NHCH$_2$CH$_2$NH—, —CH$_2$—, —CH$_2$CH$_2$O—, —CH$_2$CH$_2$—, —CH$_2$NHC(O)—, —CH$_2$CH$_2$NHC(O)—, —CH$_2$CH$_2$NH—, —CH$_2$O—, —CH$_2$CH$_2$N(CH$_3$)$_2$CH$_2$—, —CH$_2$C(O)—, or —CH$_2$CH$_2$C(O)—.

$R^4$ is independently an oligonucleotide as described herein.

In embodiments, a polymerizable monomer is selected from:

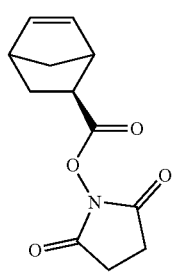
1

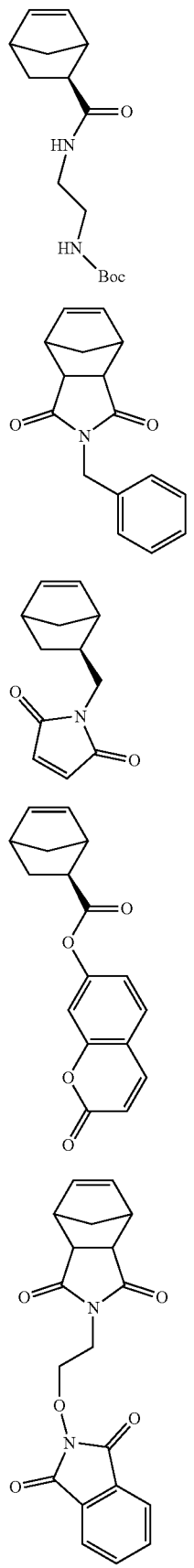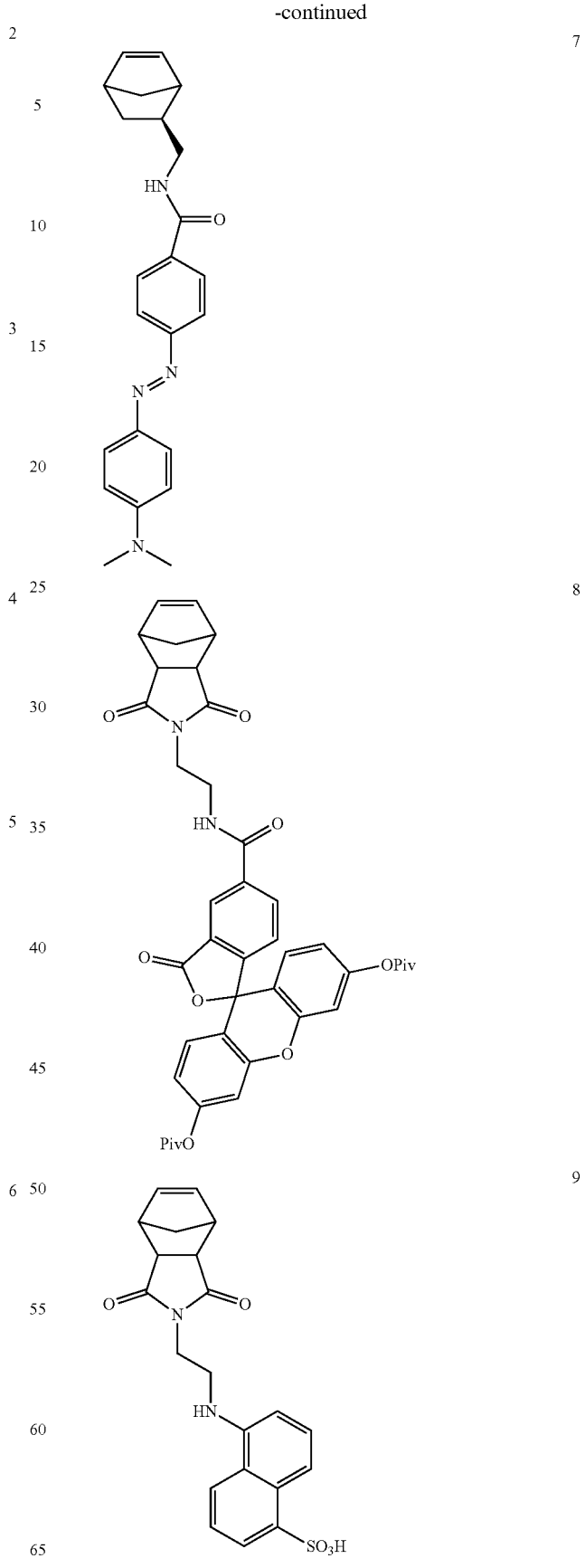

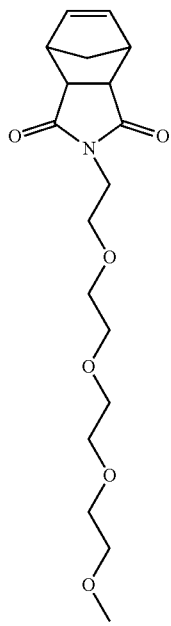

10

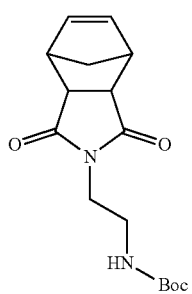

11

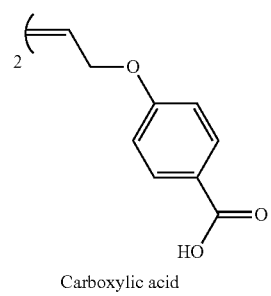

Carboxylic acid

35

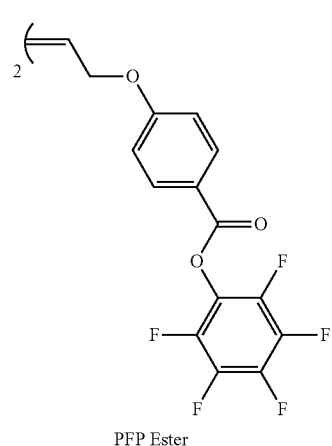

PFP Ester

36

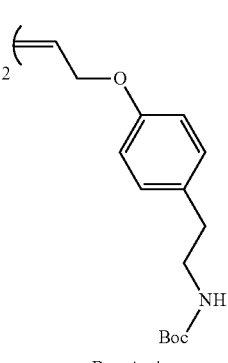

Boc-Amine

37

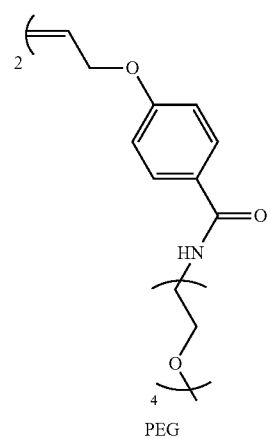

PEG

38

A "terminal polymer moiety" as used herein, refers to a chemical moiety that results from termination of a polymerization reaction (e.g., by addition of a chain terminator or transfer agent that may be modified to form the terminal polymer moiety in the termination reaction). Terminal polymer moieties may include a solid support, nanoparticle or appropriate termination moiety (e.g. substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl). In embodiments, a terminal polymer moiety includes a functional moiety, for example a detectable moiety. In embodiments, a terminal polymer moiety is the polymerization product of an ethyl vinyl ether. In embodiments, a terminal polymer polymer moiety is the polymerization product of an alkene containing substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, a terminal polymer moiety is the polymerization product of an alkene containing compound (e.g., also including a function group, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or detectable moiety). In embodiments, a terminal polymer moiety is selected from:

-continued

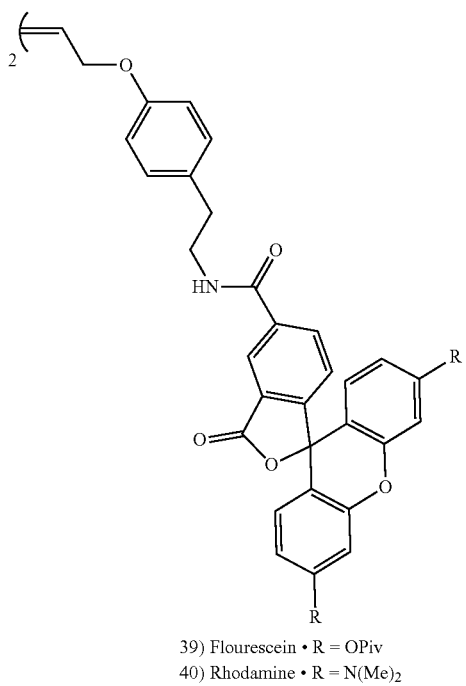

39) Flourescein • R = OPiv
40) Rhodamine • R = N(Me)₂

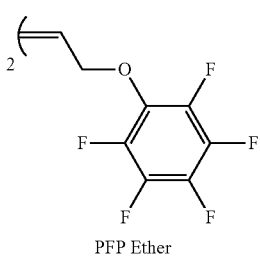

DABCYL

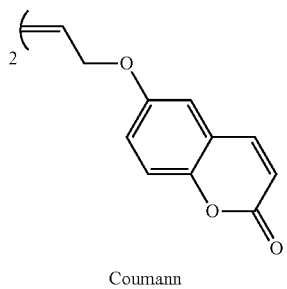

PFP Ether

-continued

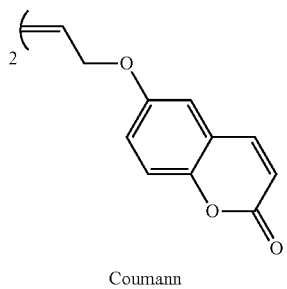

Coumarin

The term "ring-opening metathesis polymerization" or "ROMP" is used in accordance with its meaning in polymer chemistry and refers to a chain-growth polymerization (e.g., olefin metathesis chain-growth polymerization). In embodiments, the reaction is driven by relief of ring strain in cyclic olefins (e.g., norbornene or cyclopentene). In embodiments, the ROMP uses a ruthenium catalyst. In embodiments, the ROMP uses a Grubbs' catalyst. In embodiments, the ROMP uses a Mo catalyst. In embodiments, the ROMP uses [Mo(=CHBut)(Nar)(OR)2]. In embodiments, the ROMP uses a transition metal catalyst. In embodiments, the ROMP uses a transition metal carbine complex catalyst. In embodiments, the ROMP uses Benzylidene-bis(tricyclohexylphosphine)-dichlororuthenium. In embodiments, the ROMP uses [1,3-bis-(2,4,6-trimethylphenyl)-2-imidazolidinylidene]dichloro(phenylmethylene)(tricyclohexylphosphine)ruthenium. In embodiments, the ROMP uses Dichloro(o-isopropoxyphenylmethylene)(tricyclohexylphosphine)ruthenium(II). In embodiments, the ROMP uses [1,3-Bis-(2,4,6-trimethylphenyl)-2-imidazolidinylidene]dichloro(o-isopropoxyphenylmethylene)ruthenium. In embodiments, the ROMP uses a third generation Grubbs' catalyst. In embodiments, the ROMP uses (IMesH₂)(C₅H₅N)₂(Cl)₂Ru=CHPh.

Where substituent groups are specified by their conventional chemical formulae, written from left to right, they equally encompass the chemically identical substituents that would result from writing the structure from right to left, e.g., —CH₂O— is equivalent to —OCH₂—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., Ci-Cio means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH₂CH₂CH₂CH₂—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH2—CH2—O—CH3, —CH2—CH2—NH—CH3, —CH2—CH$_2$—N(CH$_3$)—CH3, —CH$_2$—S—CH$_2$—CH$_3$, —CH$_2$—CH $_2$, —S(O)—CH $_3$, —CH$_2$—CH$_2$—S(O) $_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH $_2$—CH$_3$, and —CN. Up to two or three heteroatoms may be consecutive, such as, for example, —CH$_2$—NH—OCH$_3$ and —CH $_2$—O—Si(CH $_3$)$_3$—.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O) $_2$—. As described above, heteroalkyl groups, as used herein, include those groups that are attached to the remainder of the molecule through a heteroatom, such as —C(O)R', —C(O)NR', —NR'R", —OR', —SR', and/or —SO $_2$R. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic non-aromatic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(Ci-C4) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently (e.g., biphenyl). A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C1-C4 alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR,
=N—OR, —NR'R", —SR, -halogen, —SiR'R'R''', —OC(O)R, —C(O)R', —CO$_2$R, —CONR'R", —OC(O)NR'R", —NR"C(O)R, —NR'—C(O)NR"R''', —NR"C(O)$_2$R, —NR—C(NR'R"R''')=NR'''', —NR—C(NR'R")=NR''', —S(O)R', —S(O)$_2$R, —S(O)$_2$NR'R", —NRSO$_2$R, —NRTWR", —ONRR'R", —NR'C=(O)NR"NR'''R'''', —CN, —NO$_2$, in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR, -halogen, —SiR'R"R''', —OC(O)R', —C(O)R', —CO$_2$R, —CONR'R", —OC(O)NR'R", —NR"C(O)R, —NR'—C(O)NR"R''', —NR"C(O)$_2$R, —NR—C(NR'R"R''')=NR'''', —NR—C(NR'R")=NR''', —S(O)R, —S(O)$_2$R, —S(O)$_2$NRR", —NRSO$_2$R, —NR'NR"R''', —ONRR", —NRC=(O)NR"NR'''R'''', —CN, —NO$_2$, —R', —N$_3$, —CH(Ph)$_2$, fluoro(Ci-C$_4$)alkoxy, and fluoro(Ci-C$_4$)alkyl, in a number ranging from zero to the total number of open valences on the aromatic ring system; and where R, R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR)$_q$—U—, wherein T and U are independently —NR—, —O—, —CRR—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_S$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R, R", and R" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C1-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C3-C8 cycloalkyl, each substituted or unsubstituted heterocycloalkyl is a substituted or unsubstituted 3 to 8 membered heterocycloalkyl, each substituted or unsubstituted aryl is a substituted or unsubstituted C6-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted C3-C7 cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C1-C2$_0$ alkyl, each substituted or unsubstituted heteroalkyl is a substituted or unsubstituted 2 to 20 membered heteroalkyl, each substituted or unsubstituted cycloalkyl is a substituted or unsubstituted C3-C8 cycloalkyl, each substituted or unsubstituted heterocycloalkyl is a substituted or unsubstituted 3 to 8 membered heterocycloalkyl, each substituted or unsubstituted aryl is a substituted or unsubstituted C6-C10 aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C1-C20 alkylene, each substituted or unsubstituted heteroalkylene is a substituted or unsubstituted 2 to 20 membered heteroalkylene, each substituted or unsubstituted cycloalkylene is a substituted or unsubstituted C3-C8 cycloalkylene, each substituted or unsubstituted heterocycloalkylene is a substituted or unsubstituted 3 to 8 membered heterocycloalkylene, each substituted or unsubstituted arylene is a substituted or unsubstituted C6-C10 arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted C3-C7 cycloalkyl, each substituted or unsubstituted heterocycloalkyl is a substituted or unsubstituted 3 to 7 membered heterocycloalkyl, each substituted or unsubstituted aryl is a substituted or unsubstituted C6-C10 aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted C3-C7 cycloalkylene, each substituted or unsubstituted heterocycloalkylene is a substituted or unsubstituted 3 to 7 membered heterocycloalkylene, each substituted or unsubstituted arylene is a substituted or unsubstituted C6-C10 arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et ah, *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol " ⌇ " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_i$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatry exams, and/or a psychiatric evaluation.

An "effective amount" is an amount sufficient to accomplish a stated purpose (e.g. achieve the effect for which it is administered, treat a disease, reduce enzyme activity, increase enzyme activity, reduce transcriptional activity, increase transcriptional activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein (e.g. transcription factor) relative to the absence of the antagonist. An "activity increasing amount," as used herein, refers to an amount of agonist (activator) required to increase the activity of an enzyme or protein (e.g. transcription factor) relative to the absence of the agonist. A "function disrupting amount," as used herein, refers to the amount of antagonist (inhibitor) required to disrupt the function of an enzyme or protein (e.g. transcription factor) relative to the absence of the antagonist. A "function increasing amount," as used herein, refers to the amount of agonist (activator) required to increase the function of an enzyme or protein (e.g. transcription factor) relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "associated" or "associated with" in the context of a substance or substance activity or function associated with a disease means that the disease is caused by (in whole or in part), or a symptom of the disease is caused by (in whole or in part) the substance or substance activity or function.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g.

agonist) interaction means positively affecting (e.g. increasing) the activity or function of the protein The term "modulator" refers to a composition that increases or decreases the level of a target molecule or the function of a target molecule.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a mammal. In some embodiments, a patient is a mouse. In some embodiments, a patient is an experimental animal. In some embodiments, a patient is a rat. In some embodiments, a patient is a test animal.

"Disease" or "condition" refer to a state of being or health status of a patient or subject capable of being treated with a compound, pharmaceutical composition, or method provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In embodiments, administration includes direct administration to a tumor. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent or chemotherapeutic). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by trans dermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments, the nucleic acids herein contain phosphodiester bonds. In other embodiments, nucleic acid analogs are included that may have alternate backbones (e.g. phosphodiester derivatives), including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, peptide nucleic acid linkages, or O-methylphosphoroamidite linkages (see Eckstein, Oligonucleotides and Analogues: A Practical Approach, Oxford University Press), and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (UNA)), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et ah, J. Biol. Chem. 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An amino acid residue in a protein "corresponds" to a given residue when it occupies the same essential structural position within the protein as the given residue.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Current Protocols in Molecular Biology (Ausubel et al., eds. 1995 supplement)).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology-Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in IX SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

A "label" or a "detectable moiety" is a composition detectable by spectroscopic, photochemical, biochemical, immunochemical, chemical, magnetic resonance imaging, or other physical means. For example, useful detectable moieties include $^{32}P$, fluorescent dyes, electronic dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystallme SPIO, monochrystallme SPIO aggregates, monochrystallme iron oxide nanoparticles, monochrystallme iron oxide, other nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable moieties also include any of the above compositions encapsulated in nanoparticles, particles, aggregates, coated with additional compositions, derivatized for binding to a targeting agent (e.g. compound described herein). Any method known in the art for conjugating an oligonucleotide or protein to the label may be employed, e.g., using methods described in Hermanson, *Bioconjugate Techniques* 1996, Academic Press, Inc., San Diego.

MRI can be used to non-invasively acquire tissue images with high resolution. Paramagnetic agents or USPIO nanoparticles or aggregates thereof enhance signal attenuation on $T_2$-weighted magnetic resonance images, and conjugation of such nanoparticles to binding ligands permits the detection of specific molecules at the cellular level. For example, MRI with nanoparticle detection agents can detect small foci of cancer. See e.g., Y. W. Jun et al., 2005, *J. Am. Chem. Soc.* 127:5732-5733; Y. M. Huh et al., 2005, *J. Am. Chem. Soc.* 127:12387-12391. Contrast-enhanced MRI is well-suited for the dynamic non-invasive imaging of macromolecules or of molecular events, but it requires ligands that specifically bind to the molecule of interest. J. W. Bulte et al., 2004, *NMR Biomed.* 17:484-499. Fluorescent dyes and fluorophores (e.g. fluorescein, fluorescein isothiocyanate, and fluorescein derivatives) can be used to non-invasively acquire tissue images with high resolution, with for example spectrophotometry, two-photon fluorescence, two-photon laser microscopy, or fluorescence microscopy (e.g. of tissue biopsies). MRI can be used to non-invasively acquire tissue images with high resolution, with for example paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, other nanoparticle contrast agents. MRI can be used to non-invasively acquire tissue images with high resolution, with for example Gadolinium, including liposomes or other delivery vehicles containing Gadolinium chelate ("Gd-chelate") molecules. Positron emission tomography (PET), PET/computed tomography (CT), single photon emission computed tomography (SPECT), and SPECT/CT can be used to non-invasively acquire tissue images with high resolution, with for example radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia. Ultrasound (ultrasonography) and contrast enhanced ultrasound (contrast enhanced ultrasonography) can be used to non-invasively acquire tissue images with high resolution, with for example biocolloids or microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.). X-ray imaging (radiography) or CT can be used to non-invasively acquire tissue images with high resolution, with for example iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, or gold nanoparticle aggregates. These detection methods and instruments and detectable moieties capable of being measured or detected by the corresponding method are non-limiting examples.

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der waal's bond(s)/interactions, hydrogen bond(s), polar bond(s), or combinations or mixtures thereof).

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

II. Compositions

The nucleic acid polymer described herein can be generated via graft-through polymerization, i.e., where the monomer is a "macromonomer" and is polymerized directly such that each position contains the side chain (e.g., nucleic acid) associated with the monomer. Such a polymer is entirely unique from analogues generated via post-polymerization conjugation reactions since not every position of the analogue is modified. Polymers generated via graft-through polymerization and polymers generated via post-polymerization modification are fundamentally different structures. For instances, nucleic acid polymers of the present invention possess a dense array of nucleic acids.

Graft-through polymerization can be performed by any method amenable to the functional groups present. For instance, any polymerization strategy can be used to generate a dense, brush polymer accessible only via graft-through polymerization of a monomer of nucleic acid.

In an aspect is provided a graft polymer including a linear backbone covalently bound to a plurality of oligonucleotide branches. The graft polymer is assembled by graft-through polymerization of a plurality of oligonucleotide monomers including a polymerizable monomer covalently bound to an oligonucleotide. The oligonucleotide thereby forming each of the plurality of oligonucleotide branches.

In embodiments, the graft-through polymerization employs ring-opening metathesis polymerization (ROMP). In embodiments, the graft-through polymerization includes ring-opening metathesis polymerization (ROMP). In embodiments, the graft-through polymerization employs radical polymerization, controlled radical polymerization, reversible addition-fragmentation chain transfer (RAFT) polymerization, atom transfer radical polymerization (ATRP), ring-opening metathesis polymerization (ROMP), anionic polymerization, cationic polymerization, free radical living polymerization, acyclic diene metathesis polymerization, radiation-induced polymerization, ring-opening olefin metathesis polymerization, polycondensation reactions, or iniferter-induced polymerization.

In embodiments, the oligonucleotide (e.g. $R^3$ or $R^4$) includes at least 2 different nucleobases. In embodiments, the oligonucleotide (e.g. $R^3$ or $R^4$) includes at least 3 different nucleobases. In embodiments, the oligonucleotide (e.g. $R^3$ or $R^4$) includes at least 4 different nucleobases. In embodiments, the oligonucleotide (e.g. $R^3$ or $R^4$) includes at least 5 different nucleobases. In embodiments, the oligonucleotide (e.g. $R^3$ or $R^4$) includes at least 6 different nucleobases. In embodiments, the oligonucleotide (e.g. $R^3$ or $R^4$) includes at least 7 different nucleobases. In embodiments, the oligonucleotide (e.g. $R^3$ or $R^4$) includes at least 3 nucleobases and at least 2 different nucleobases. In embodiments, the oligonucleotide (e.g. $R^3$ or $R^4$) includes at least 5 nucleobases and at least 3 different nucleobases. In embodiments, the oligonucleotide (e.g. $R^3$ or $R^4$) includes at least 10 nucleobases and at least 4 different nucleobases. In embodiments, the graft polymer includes at least 3 oligonucleotide (e.g. $R^3$ or $R^4$) branches. In embodiments, the graft polymer includes at least 5 oligonucleotide (e.g. $R^3$ or $R^4$) branches. In embodiments, the graft polymer includes at least 10 oligonucleotide (e.g. $R^3$ or $R^4$) branches. In embodiments, the oligonucleotide (e.g. $R^3$ or $R^4$) is between 2 and 1000 bases long. In embodiments, the oligonucleotide is between 2 and 900 bases long. In embodiments, the oligonucleotide is between 2 and 800 bases long. In embodiments, the oligonucleotide is between 2 and 700 bases long. In embodiments, the oligonucleotide is between 2 and 600 bases long. In embodiments, the oligonucleotide is between 2 and 500 bases long. In embodiments, the oligonucleotide is between 2 and 400 bases long. In embodiments, the oligonucleotide is between 2 and 300 bases long. In embodiments, the oligonucleotide is between 2 and 200 bases long. In embodiments, the oligonucleotide is between 2 and 100 bases long. In embodiments, the oligonucleotide is between 2 and 50 bases long. In embodiments, the oligonucleotide is between 2 and 49 bases long. In embodiments, the oligonucleotide is between 2 and 48 bases long. In embodiments, the oligonucleotide is between 2 and 47 bases long. In embodiments, the oligonucleotide is between 2 and 46 bases long. In embodiments, the oligonucleotide is between 2 and 45 bases long. In embodiments, the oligonucleotide is between 2 and 44 bases long. In embodiments, the oligonucleotide is between 2 and 43 bases long. In embodiments, the oligonucleotide is between 2 and 42 bases long. In embodiments, the oligonucleotide is between 2 and 41 bases long. In embodiments, the oligonucleotide is between 2 and 40 bases long. In embodiments, the oligonucleotide is between 2 and 39 bases long. In embodiments, the oligonucleotide is between 2 and 38 bases long. In embodiments, the oligonucleotide is between 2 and 37 bases long. In embodiments, the oligonucleotide is between 2 and 36 bases long. In embodiments, the oligonucleotide is between 2 and 35 bases long. In embodiments, the oligonucleotide is between 2 and 34 bases long. In embodiments, the oligonucleotide is between 2 and 33 bases long. In embodiments, the oligonucleotide is between 2 and 32 bases long. In embodiments, the oligonucleotide is between 2 and 31 bases long. In embodiments, the oligonucleotide is between 2 and 30 bases long. In embodiments, the oligonucleotide is between 2 and 29 bases long. In embodiments, the oligonucleotide is between 2 and 28 bases long. In embodiments, the oligonucleotide is between 2 and 27 bases long. In embodiments, the oligonucleotide is between 2 and 26 bases long. In embodiments, the oligonucleotide is between 2 and 25 bases long. In embodiments, the oligonucleotide is between 2 and 24 bases long. In embodiments, the oligonucleotide is between 2 and 23 bases long. In embodiments, the oligonucleotide is between 2 and 22 bases long. In embodiments, the oligonucleotide is between 2 and 21 bases long. In embodiments, the oligonucleotide is between 2 and 20 bases long. In embodiments, the oligonucleotide is between 2 and 19 bases long. In embodiments, the oligonucleotide is between 2 and 18 bases long. In embodiments, the oligonucleotide is between 2 and 17 bases long. In embodiments, the oligonucleotide is between 2 and 16 bases long. In embodiments, the oligonucleotide is between 2 and 15 bases long. In embodiments, the oligonucleotide is between 2 and 14 bases long. In embodiments, the oligonucleotide is between 2 and 13 bases long. In embodiments, the oligonucleotide is between 2 and 12 bases long. In embodiments, the oligonucleotide is between 2 and 11 bases long. In embodiments, the oligonucleotide is between 2 and 10 bases long. In embodiments, the oligonucleotide is between 2 and 9 bases long. In embodiments, the oligonucleotide is between 2 and 8 bases long. In embodiments, the oligonucleotide is between 2 and 7 bases long. In embodiments, the oligonucleotide is between 2 and 6 bases long. In embodiments, the oligonucleotide is between 2 and 5 bases long. In embodiments, the oligonucleotide is between 2 and 4 bases long. In embodiments, the oligonucleotide is between 2 and 3 bases long. In embodiments, the oligonucleotide is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 bases long.

In embodiments, the oligonucleotide (e.g. $R^3$ or $R^4$) includes nucleotides with alternate backbones from the naturally occurring phophosphodiester bond in DNA and RNA (e.g., phosphodiester derivatives). In embodiments, the oligonucleotide (e.g. $R^3$ or $R^4$) includes phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, peptide nucleic acid linkages, O-methylphosphoroamidite linkages, positive backbone linkages; non-ionic backbone linkages, modified sugars, and/or non-ribose backbones (e.g. phosphorodiamidate morpholino oligos or locked nucleic acids (LNA)). In embodiments, the oligonucleotide (e.g. $R^3$ or $R^4$) includes phosphodiester bonds such as the naturally occurring backbone linkages in DNA or RNA.

In embodiments, the oligonucleotide includes phosphoramidate linkages. In embodiments, the oligonucleotide includes phosphorodiamidate linkages. In embodiments, the oligonucleotide includes phosphorothioate (also known as phosphothioate) linkages. In embodiments, the oligonucleotide includes phosphorodithioate linkages. In embodiments, the oligonucleotide includes phosphonocarboxylic acid linkages. In embodiments, the oligonucleotide includes phosphonocarboxylate linkages. In embodiments, the oligonucleotide includes phosphonoacetic acid linkages. In embodiments, the oligonucleotide includes phosphonoformic acid linkages. In embodiments, the oligonucleotide includes methyl phosphonate linkages. In embodiments, the oligonucleotide includes boron phosphonate linkages. In embodiments, the oligonucleotide includes peptide nucleic acid linkages. In embodiments, the oligonucleotide includes O-methylphosphoroamidite linkages. In embodiments, the oligonucleotide includes positive backbone linkages. In embodiments, the oligonucleotide includes non-ionic backbone linkages. In embodiments, the oligonucleotide includes modified sugar linkages. In embodiments, the oligonucleotide includes non-ribose backbone linkages (e.g. phosphorodiamidate morpholino oligos or locked nucleic acids (LNA)).

In embodiments, the oligonucleotide (e.g. $R^3$ or $R^4$) includes a phosphoramidate linkage. In embodiments, the oligonucleotide includes a phosphorodiamidate linkage. In embodiments, the oligonucleotide includes a phosphorothioate (also known as phosphothioate) linkage. In embodiments, the oligonucleotide includes a phosphorodithioate linkage. In embodiments, the oligonucleotide includes a phosphonocarboxylic acid linkage. In embodiments, the oligonucleotide includes a phosphonocarboxylate linkage. In embodiments, the oligonucleotide includes a phosphonoacetic acid linkage. In embodiments, the oligonucleotide includes a phosphonoformic acid linkage. In embodiments, the oligonucleotide includes a methyl phosphonate linkage. In embodiments, the oligonucleotide includes a boron phosphonate linkage. In embodiments, the oligonucleotide includes a peptide nucleic acid linkage. In embodiments, the oligonucleotide includes an O-methylphosphoroamidite linkage. In embodiments, the oligonucleotide includes a positive backbone linkage. In embodiments, the oligonucleotide includes a non-ionic backbone linkage. In embodiments, the oligonucleotide includes a modified sugar linkage. In embodiments, the oligonucleotide includes a non-ribose backbone linkage (e.g. phosphorodiamidate morpholino oligos or locked nucleic acids (LNA)).

In embodiments, the graft polymer has the formula: $R^1$-[M(O)]$_n$—$R^2$. The symbol n is an integer from 2 to 1000. M is the polymerized product of the polymerizable monomer. O is the oligonucleotide. $R^1$ and $R^2$ are terminal polymer moieties.

In embodiments, n is an integer from 2 to 900. In embodiments, n is an integer from 2 to 800. In embodiments, n is an integer from 2 to 700. In embodiments, n is an integer from 2 to 600. In embodiments, n is an integer from 2 to 500. In embodiments, n is an integer from 2 to 400. In embodiments, n is an integer from 2 to 300. In embodiments, n is an integer from 2 to 200. In embodiments, n is an integer from 2 to 100. In embodiments, n is an integer from 2 to 50. In embodiments, n is an integer from 2 to 49. In embodiments, n is an integer from 2 to 48. In embodiments, n is an integer from 2 to 47. In embodiments, n is an integer from 2 to 46. In embodiments, n is an integer from 2 to 45. In embodiments, n is an integer from 2 to 44. In embodiments, n is an integer from 2 to 43. In embodiments, n is an integer from 2 to 42. In embodiments, n is an integer from 2 to 41. In embodiments, n is an integer from 2 to 40. In embodiments, n is an integer from 2 to 39. In embodiments, n is an integer from 2 to 38. In embodiments, n is an integer from 2 to 37. In embodiments, n is an integer from 2 to 36. In embodiments, n is an integer from 2 to 35. In embodiments, n is an integer from 2 to 34. In embodiments, n is an integer from 2 to 33. In embodiments, n is an integer from 2 to 32. In embodiments, n is an integer from 2 to 31. In embodiments, n is an integer from 2 to 30. In embodiments, n is an integer from 2 to 29. In embodiments, n is an integer from 2 to 28. In embodiments, n is an integer from 2 to 27. In embodiments, n is an integer from 2 to 26. In embodiments, n is an integer from 2 to 25. In embodiments, n is an integer from 2 to 24. In embodiments, n is an integer from 2 to 23. In embodiments, n is an integer from 2 to 22. In embodiments, n is an integer from 2 to 21. In embodiments, n is an integer from 2 to 20. In embodiments, n is an integer from 2 to 19. In embodiments, n is an integer from 2 to 18. In embodiments, n is an integer from 2 to 17. In embodiments, n is an integer from 2 to 16. In embodiments, n is an integer from 2 to 15. In embodiments, n is an integer from 2 to 14. In embodiments, n is an integer from 2 to 13. In embodiments, n is an integer from 2 to 12. In embodiments, n is an integer from 2 to 11. In embodiments, n is an integer from 2 to 10. In embodiments, n is an integer from 2 to 9. In embodiments, n is an integer from 2 to 8. In embodiments, n is an integer from 2 to 7. In embodiments, n is an integer from 2 to 6. In embodiments, n is an integer from 2 to 5. In embodiments, n is an integer from 2 to 4. In embodiments, n is an integer from 2 to 3. In embodiments, n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000.

In embodiments, $R^1$ includes a solid support. In embodiments, $R^1$ includes a nanoparticle. In embodiments, $R^1$ includes a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^1$ includes a functional moiety. In embodiments, $R^1$ includes a detectable moiety. In embodiments, $R^1$ includes a $^2P$, fluorescent dye, electron-dense reagent, enzyme (e.g., as commonly used in an ELISA), biotin, digoxigenin, paramagnetic molecule, paramagnetic nanoparticle, ultrasmall superparamagnetic iron oxide ("USPIO") nanoparticles, USPIO nanoparticle aggregate, superparamagnetic iron oxide ("SPIO") nanoparticle, SPIO nanoparticle aggregate, monochrystalline SPIO, monochrystalline SPIO aggregate, monochrystalline iron oxide nanoparticle, monochrystalline iron oxide, other nanoparticle contrast agent, liposome or other delivery vehicle containing Gadolinium chelate ("Gd-chelate") molecule, Gadolinium, radioisotope, radionuclide (e.g. carbon-11, nitrogen-13, oxygen-15, fluorine-18, rubidium-82), fluorodeoxyglucose (e.g. fluorine-18 labeled), any gamma ray emitting radionuclids, positron-emitting radionuclide, radiolabeled glucose, radiolabeled water, radiolabeled ammonia, biocolloids, microbubble (e.g. including microbubble shell including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agent (e.g. iohexol, ioversol, iopamidol, ioxilan, iopromide, diatrizoate, metrizoate, ioxaglate), barium sulfate, thorium dioxide, gold, gold nanoparticle, gold nanoparticle aggregate, fluorophore, two-photon fluorophore, or a hapten. In embodiments, $R^1$ includes a polymerization product of an ethyl vinyl ether. In embodiments, $R^1$ is the polymerization product of an alkene containing substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^1$ is the polymerization product of an alkene bonded to a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^1$ is the polymerization product of an alkene containing compound (e.g., also including a function group, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or detectable moiety). In embodiments, $R^1$ is selected from:

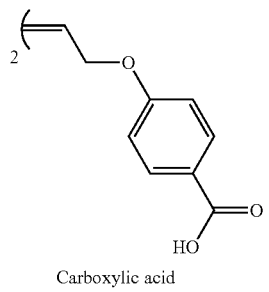

Carboxylic acid

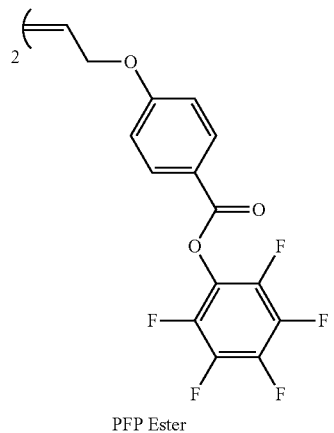

PFP Ester

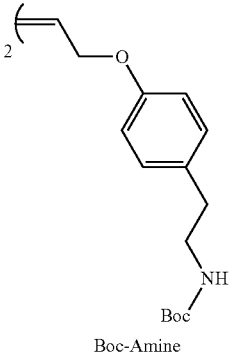

Boc-Amine

41
-continued
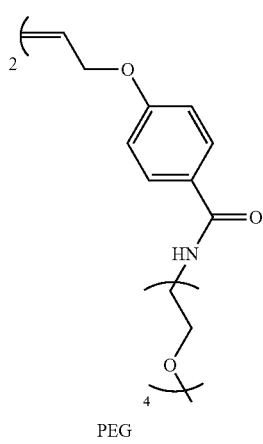
PEG
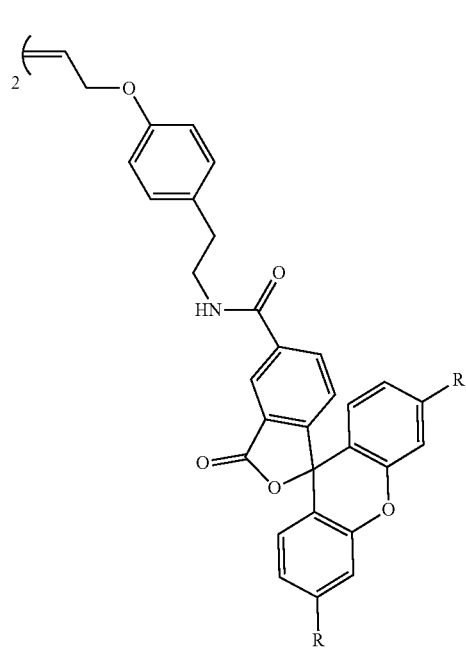
39) Flourescein • R = OPiv
40) Rhodamine • R = N(Me)₂
42
-continued
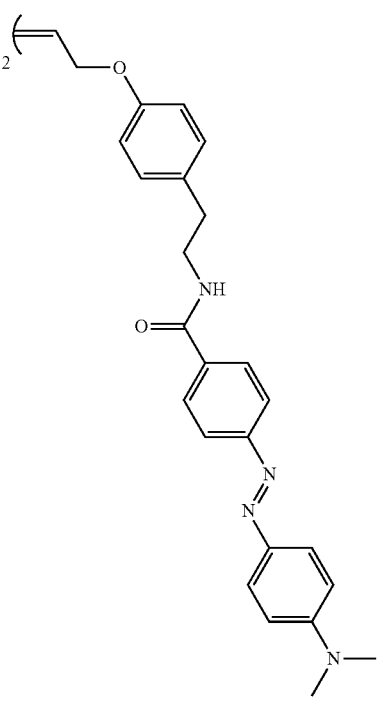
DABCYL
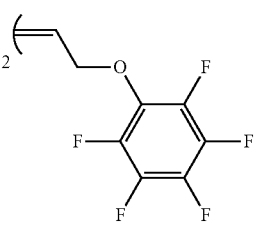
PFP Ether
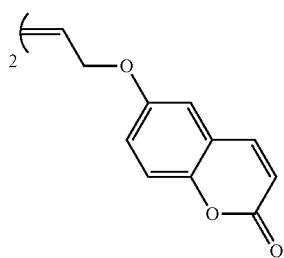
Coumarin
In embodiments, $R^2$ includes a solid support. In embodiments, $R^2$ includes a nanoparticle. In embodiments, $R^2$ includes a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^2$ includes a functional moiety. In embodiments, $R^2$ includes a detectable moiety. In embodiments, $R^2$ includes a $^{32}P$, fluorescent dye, electron-dense reagent, enzyme (e.g., as commonly used in an ELISA), biotin, digoxigenin, paramagnetic molecule, paramagnetic nanoparticle, ultrasmall superparamagnetic iron oxide ("USPIO") nanoparticles, USPIO nanoparticle aggregate, superparamagnetic iron oxide ("SPIO") nanoparticle, SPIO nanoparticle aggregate, monochrystalline SPIO, monochrystalline SPIO aggregate, monochrystalline iron oxide nanoparticle, monochrystalline iron oxide, other nanoparticle contrast agent, liposome or other delivery vehicle containing Gadolinium chelate ("Gd-chelate") molecule, Gadolinium, radioisotope, radionuclide (e.g. carbon-11, nitrogen-13, oxygen-15, fluorine-18, rubidium-82), fluorodeoxyglucose (e.g. fluorine-18 labeled), any gamma ray emitting radionuclids, positron-emitting radionuclide, radiolabeled glucose, radiolabeled water, radiolabeled ammonia, biocolloids, microbubble (e.g. including microbubble shell including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agent (e.g. iohexol, iodixanol, ioversol, iopamidol, ioxilan, iopromide, diatrizoate, metrizoate, ioxaglate), barium sulfate, thorium dioxide, gold, gold nanoparticle, gold nanoparticle aggregate, fluorophore, two-photon fluorophore, or a hapten. In embodiments, $R^2$ includes a polymerization product of an ethyl vinyl ether. In embodiments, $R^2$ is the polymerization product of an alkene containing substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^2$ is the polymerization product of an alkene bonded to a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^2$ is the polymerization product of an alkene containing compound (e.g., also including a function group, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or detectable moiety). In embodiments, $R^2$ is selected from:

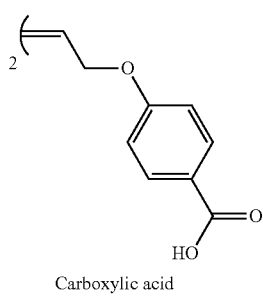

Carboxylic acid

35

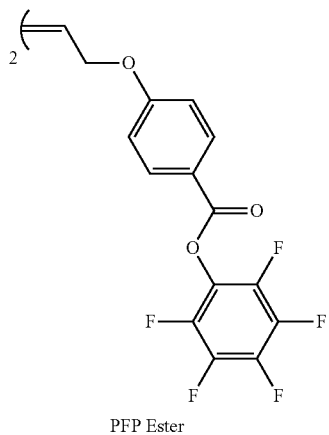

PFP Ester

36

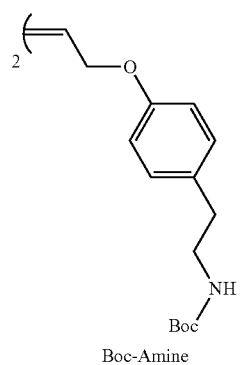

Boc-Amine

37

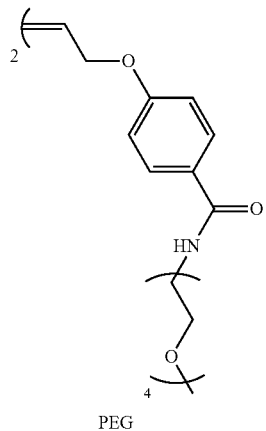

PEG

38

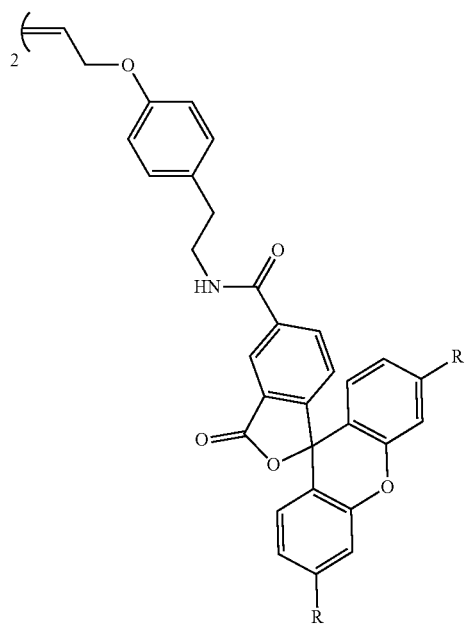

39) Flourescein • R = OPiv
40) Rhodamine • R = N(Me)₂

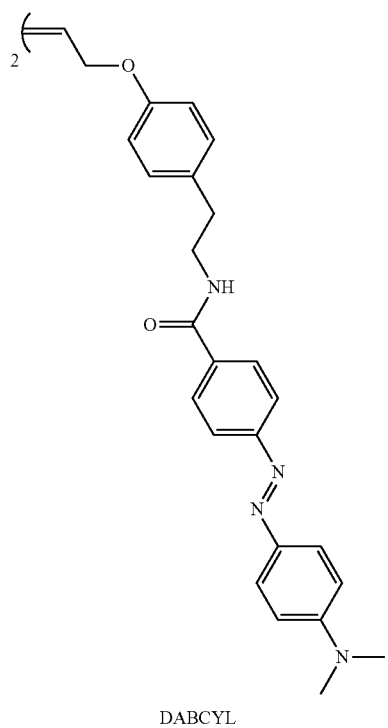

DABCYL

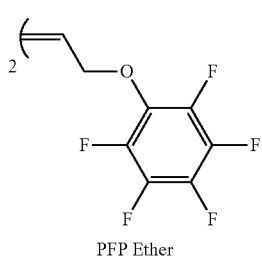

PFP Ether

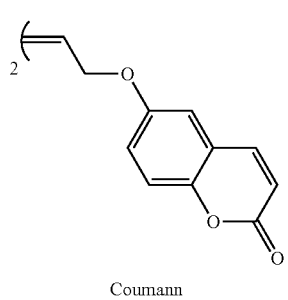

Coumarin

In embodiments, the linear backbone is a polynorbornyl chain. In embodiments, the linear backbone is a polynorbornyl derivative chain. In embodiments, the linear backbone is a poly-substituted norbornyl chain. In embodiments, the linear backbone is a substituted polynorbornene. In embodiments, the linear backbone is a polynorbornene. In embodiments, the linear backbone is a polynorbornene substituted with oligonucleotides at each norbornene monomer. In embodiments, the linear backbone is a polynorbornene substituted with an oligonucleotide, substituted or unsubstituted alkyl, substituted or unsubstituted heteroalkyl, substituted or unsubstituted cycloalkyl, substituted or unsubstituted heterocycloalkyl, substituted or unsubstituted aryl and/or substituted or unsubstituted heteroaryl. In embodiments, the linker backbone is polymerized from monomers of:

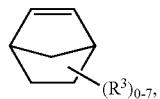 (IA)

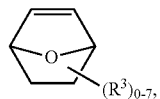 (IB)

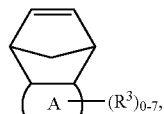 (IC)

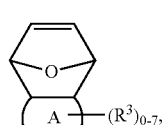 (ID)

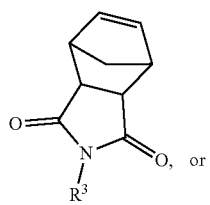 (IE)

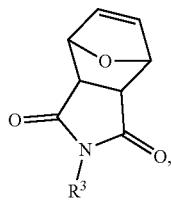
(IF)

wherein Ring A, n and $R^3$ are as set forth herein. In embodiments, the linker backbone is polymerized from monomers of:

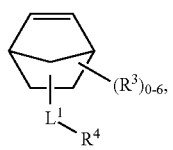
(IIIA)

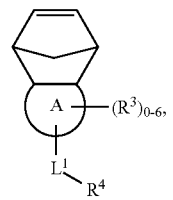
(IIIB)

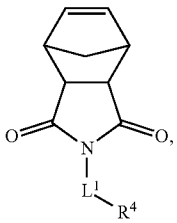
(IIIC)

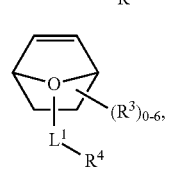
(IIID)

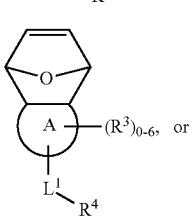
(IIIE)

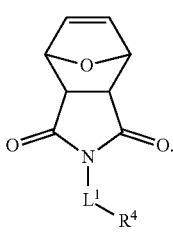
(IIIF)

In formula (IIA)-(IIF), Ring A, $R^3$, $R^4$, and $L^1$ are as set forth herein. In embodiments, the linker backbone is polymerized from monomers of:

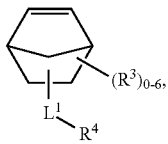
(IIIA)

(IIIB)

(IIIC)

(IIID)

(IIIE)

(IIIF)

In formula (IIIA)-(IIIF), Ring A, $L^1$ and $R^4$ is as defined herein. In embodiments, M(O) is

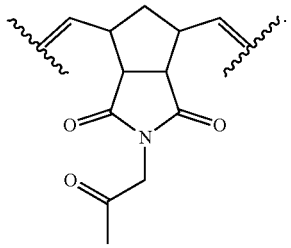
oligonucleotide (O)

In embodiments, M(O) is

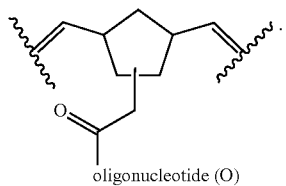

oligonucleotide (O)

In embodiments, M(O) is

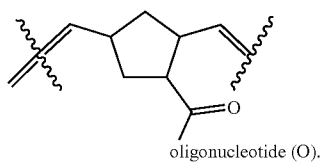

oligonucleotide (O).

In embodiments, M(O) is

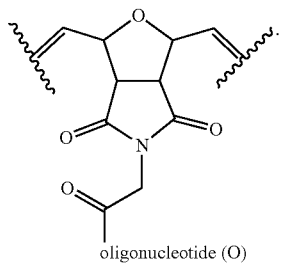

oligonucleotide (O)

In embodiments, M(O) is

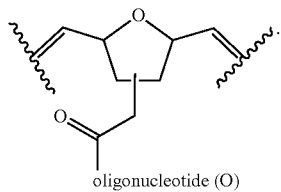

oligonucleotide (O)

In embodiments, M(O) is

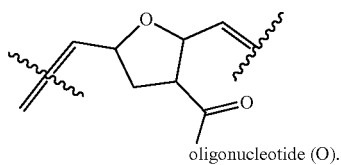

oligonucleotide (O).

in embodiments, each oligonucleotide (e.g. $R^3$ or $R^4$) in the graft polymer is optionally different. In embodiments, each oligonucleotide (e.g. $R^3$ or $R^4$) in the graft polymer is identical. In embodiments, the graft polymer includes blocks of oligonucleotide (e.g. $R^3$ or $R^4$) wherein the nucleotides in each block are identical and the oligonucleotide (e.g. $R^3$ or $R^4$) in different blocks are optionally different. In embodiments, the graft polymer includes blocks of oligonucleotide (e.g. $R^3$ or $R^4$) wherein the nucleotides in each block are identical and the oligonucleotide (e.g. $R^3$ or $R^4$) in different blocks are different.

In an aspect is provided a block graft copolymer including a linear backbone covalently bound to a plurality of oligonucleotide (e.g. $R^3$ or $R^4$) branches and a plurality of non-oligonucleotide side chains, wherein: the plurality of oligonucleotide branches form a first block portion of the graft copolymer and the non-oligonucleotide side chains form a second block portion of the graft copolymer; the graft copolymer is assembled by graft-through polymerization of a plurality of oligonucleotide monomers and a plurality of non-oligonucleotide monomers, wherein each of the plurality of oligonucleotide monomers includes a polymerizable monomer covalently bound to an oligonucleotide, the oligonucleotide thereby forming each of the plurality of oligonucleotide branches; and each of the plurality of non-oligonucleotide monomers includes the polymerizable monomer covalently bound to a non-oligonucleotide moiety, the non-oligonucleotide moiety thereby forming each of the plurality of non-oligonucleotide side chains.

A "non-oligonucleotide monomer" is a polymerizable monomer that does not include an oligonucleotide. A non-oligonucleotide monomer may be a polymerizable monomer covalently bound to a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, a non-oligonucleotide monomer is a hydrophobic monomer. In embodiments, each non-oligonucleotide monomer in the graft polymer is optionally different. In embodiments, each non-oligonucleotide monomer in the graft polymer is identical. In embodiments, the graft polymer includes blocks of non-oligonucleotide monomers wherein the non-oligonucleotide monomers in each block are identical and the non-oligonucleotide monomers in different blocks are optionally different. In embodiments, the graft polymer includes blocks of non-oligonucleotide monomers wherein the non-oligonucleotide monomers in each block are identical and the non-oligonucleotide monomers in different blocks are different. In embodiments, the non-oligonucleotide monomer is selected from:

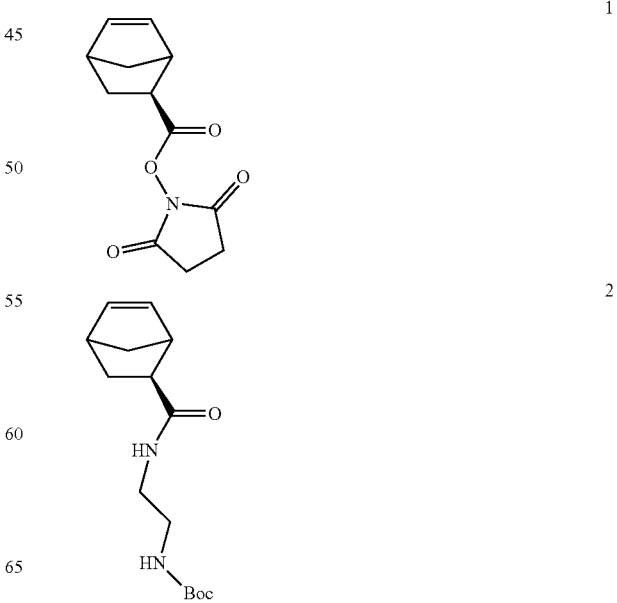

-continued
3
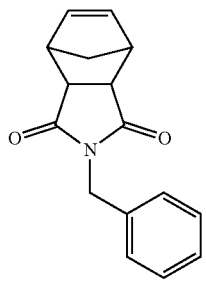
4
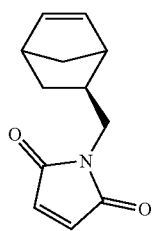
5
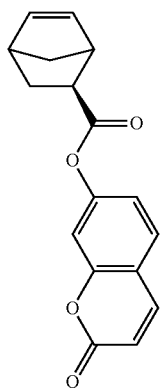
6
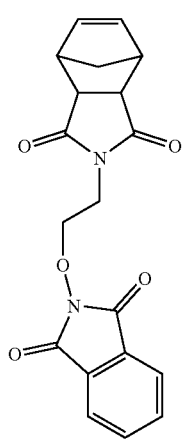
-continued
5
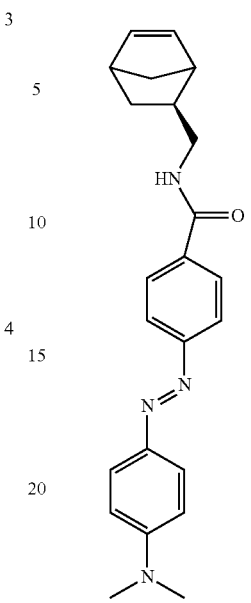
6
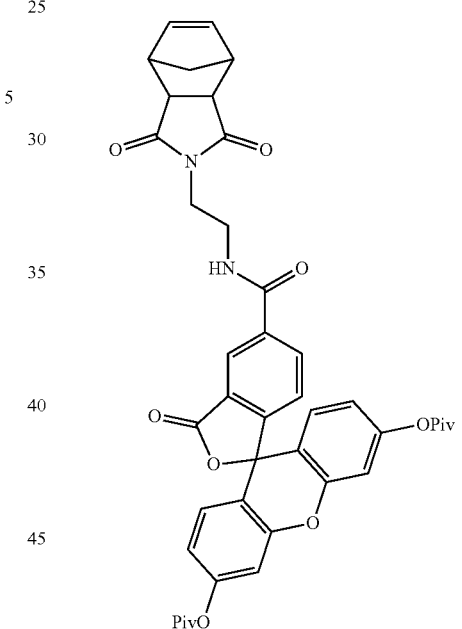
7
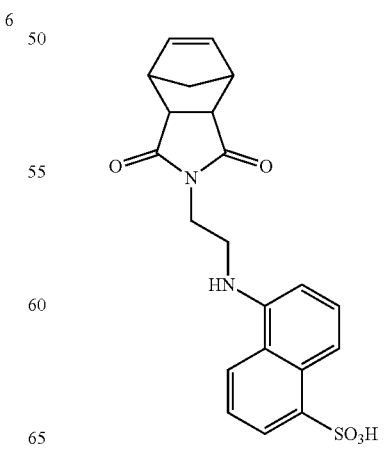

-continued

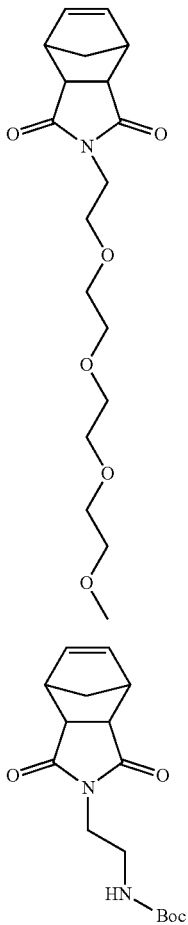

In embodiments, a non-oligonucleotide monomer is a hydrophobic monomer.

In an aspect is provided an amphiphilic block graft copolymer including a linear backbone covalently bound to a plurality of oligonucleotide (e.g. $R^3$ or $R^4$) branches and a plurality of hydrophobic side chains, wherein: the plurality of oligonucleotide branches form a hydrophilic block portion of the amphiphilic graft copolymer and the hydrophobic side chains form a hydrophobic block portion of the amphiphilic graft copolymer; the graft copolymer is assembled by graft-through polymerization of a plurality of oligonucleotide monomers and a plurality of hydrophobic monomers, wherein each of the plurality of oligonucleotide monomers includes a polymerizable monomer covalently bound to an oligonucleotide, the oligonucleotide thereby forming each of the plurality of oligonucleotide branches; and each of the plurality of hydrophobic monomers includes the polymerizable monomer covalently bound to a hydrophobic moiety, the hydrophobic moiety thereby forming each of the plurality of hydrophobic side chains.

The linear backbone, oligonucleotide (e.g. $R^3$ or $R^4$) branches, oligonucleotide monomers, graft-through polymerization, polymerizable monomer, and oligonucleotide are as described herein, including in aspects (e.g., above), embodiments (e.g., above), examples, figures, tables, schemes, and claims.

Figure 2:
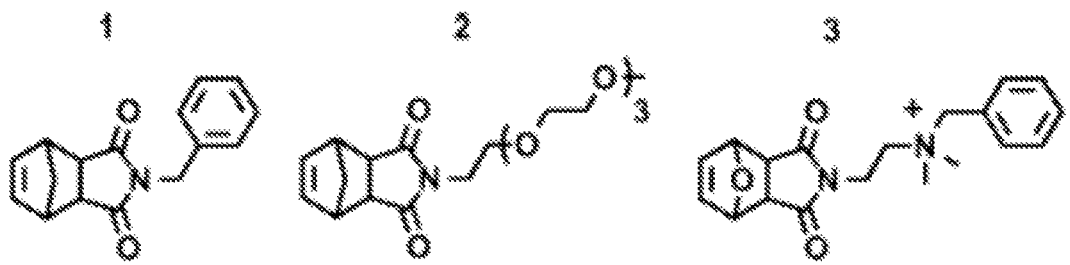
FIG. 2 shows structures of monomers used for block copolymer preparation.
Figure 3C:
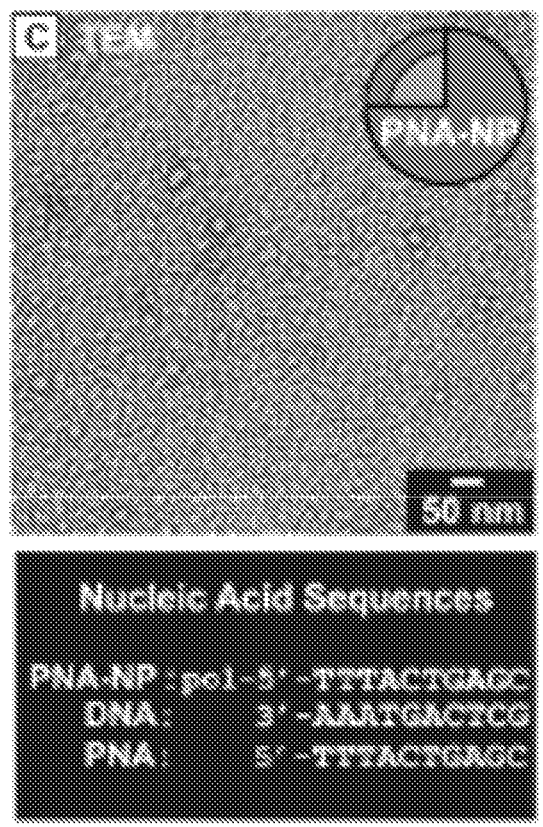
Figure 3D:
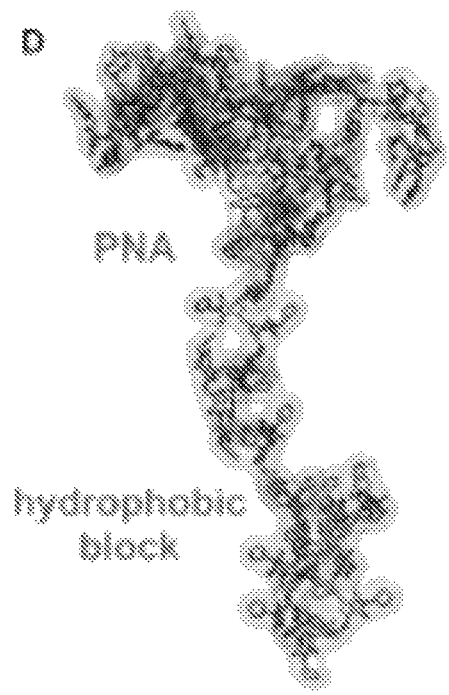
Figure 3E:
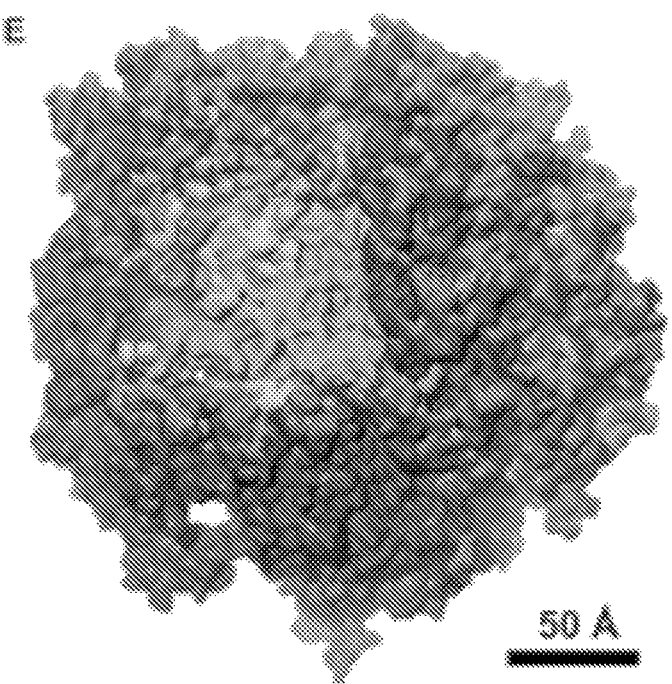

In embodiments, the hydrophobic moiety is sufficiently hydrophobic and of sufficient size such that the amphiphilic block graft polymer is capable of forming a micelle in an aqueous-based solvent. In embodiments, the hydrophobic moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the hydrophobic moiety is an unsubstituted benzyl. In embodiments, the hydrophobic moiety is a hydrophobic moiety as shown in FIG. 2.

In embodiments, the amphiphilic block graft copolymer has the formula: $R^1$-[M(O)]$_n$-[M(P)]$_m$—$R^2$ or $R^1$-[M(P)]$_m$-[M(O)]$_n$—$R^2$ wherein, n is an integer from 2 to 1000; m is an integer from 2 to 1000; M is the polymerized product of the polymerizable monomer; O is the oligonucleotide; P is the hydrophobic moiety; and $R^1$ and $R^2$ are terminal polymer moieties.

$R^1$, M, O, n, and $R^2$ are as described herein, including in aspects (e.g., above), embodiments (e.g., above), examples, figures, tables, schemes, and claims.

In embodiments, M(P) is

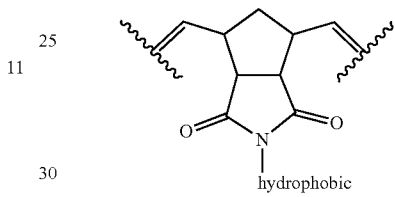

moiety (P). In embodiments, M(P) is

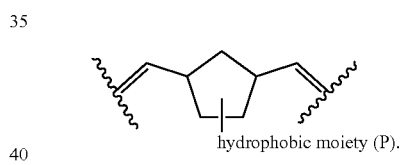

In embodiments, M(P) is

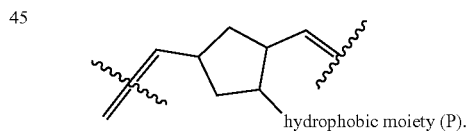

In embodiments, M(P) is

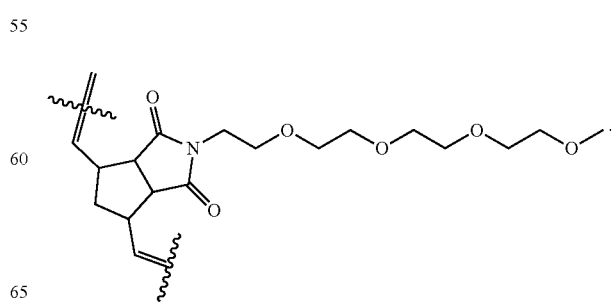

In embodiments, M(P) is

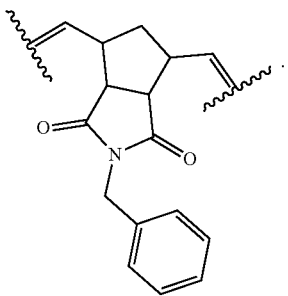 [SMILES: *=CC1CC(C=*)C2C(=O)N(Cc3ccccc3)C(=O)C12]

In embodiments, M(P) is

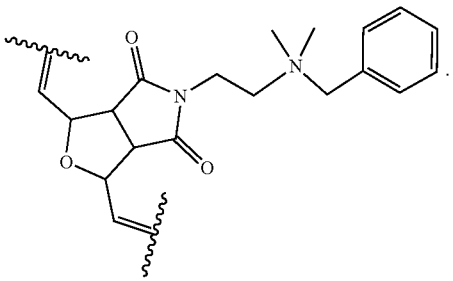

In embodiments, M(P) is

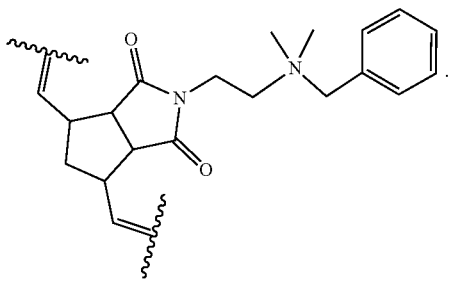

In embodiments, each hydrophobic moiety in the graft copolymer is optionally different. In embodiments, each hydrophobic moiety in the graft copolymer is identical. In embodiments, the graft copolymer includes blocks of hydrophobic moieties wherein the hydrophobic moieties in each block are identical and the hydrophobic moieties in different blocks are optionally different. In embodiments, the graft copolymer includes blocks of hydrophobic moieties wherein the hydrophobic moieties in each block are identical and the hydrophobic moieties in different blocks are different.

In embodiments, m is an integer from 2 to 900. In embodiments, m is an integer from 2 to 800. In embodiments, m is an integer from 2 to 700. In embodiments, m is an integer from 2 to 600. In embodiments, m is an integer from 2 to 500. In embodiments, m is an integer from 2 to 400. In embodiments, m is an integer from 2 to 300. In embodiments, m is an integer from 2 to 200. In embodiments, m is an integer from 2 to 100. In embodiments, m is an integer from 2 to 50. In embodiments, m is an integer from 2 to 49. In embodiments, m is an integer from 2 to 48. In embodiments, m is an integer from 2 to 47. In embodiments, m is an integer from 2 to 46. In embodiments, m is an integer from 2 to 45. In embodiments, m is an integer from 2 to 44. In embodiments, m is an intej*er from 2 to 43. In embodiments, m is an intej*er from 2 to 42. In embodiments, m is an intej*er from 2 to 41. In embodiments, m is an intej*er from 2 to 40. In embodiments, m is an intej*er from 2 to 39. In embodiments, m is an intej*er from 2 to 38. In embodiments, m is an intej*er from 2 to 37. In embodiments, m is an intej*er from 2 to 36. In embodiments, m is an intej*er from 2 to 35. In embodiments, m is an intej*er from 2 to 34. In embodiments, m is an intej*er from 2 to 33. In embodiments, m is an intej*er from 2 to 32. In embodiments, m is an intej*er from 2 to 31. In embodiments, m is an intej*er from 2 to 30. In embodiments, m is an intej*er from 2 to 29. In embodiments, m is an intej*er from 2 to 28. In embodiments, m is an intej*er from 2 to 27. In embodiments, m is an intej*er from 2 to 26. In embodiments, m is an intej*er from 2 to 25. In embodiments, m is an intej*er from 2 to 24. In embodiments, m is an intej*er from 2 to 23. In embodiments, m is an intej*er from 2 to 22. In embodiments, m is an intej*er from 2 to 21. In embodiments, m is an intej*er from 2 to 20. In embodiments, m is an intej*er from 2 to 19. In embodiments, m is an intej*er from 2 to 18. In embodiments, m is an intej*er from 2 to 17. In embodiments, m is an intej*er from 2 to 16. In embodiments, m is an intej*er from 2 to 15. In embodiments, m is an intej*er from 2 to 14. In embodiments, m is an intej*er from 2 to 13. In embodiments, m is an intej*er from 2 to 12. In embodiments, m is an intej*er from 2 to 11. In embodiments, m is an intej*er from 2 to 10. In embodiments, m is an intej*er from 2 to 9. In embodiments, m is an integer from 2 to 8. In embodiments, m is an intej*er from 2 to 7. In embodiments, m is an integer from 2 to 6. In embodiments, m is an intej*er from 2 to 5. In embodiments, m is an integer from 2 to 4. In embodiments, m is an intej*er from 2 to 3. In embodiments, m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000.

In an aspect is provided a micelle including an amphiphilic block graft copolymer described herein, including in an aspect, embodiment, example, figures, table, scheme, or claim.

In embodiments, the micelle has a diameter of between about 1 and about 1000 nm. In embodiments, the micelle has a diameter of between about 5 and about 100 nm. In embodiments, the micelle has a diameter of between about 10 and about 50 nm. In embodiments, the micelle has a diameter of between 1 and 1000 nm. In embodiments, the micelle has a diameter of between 5 and 100 nm. In embodiments, the micelle has a diameter of between 10 and 50 nm.

In embodiments, the micelle has a diameter of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm. In embodiments, the micelle has a diameter of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm.

In embodiments, the micelle diameter is a hydrodynamic diameter. In embodiments, the diameter is an average diameter of a sample.

In an aspect is provided a nanoparticle including an amphiphilic block graft copolymer described herein, including in an aspect, embodiment, example, figure, table, scheme, or claim.

In embodiments, the nanoparticle is a spherical nanoparticle.

In embodiments, the nanoparticle has a diameter of between about 1 and about 1000 nm. In embodiments, the nanoparticle has a diameter of between about 5 and about 100 nm. In embodiments, the nanoparticle has a diameter of between about 10 and about 50 nm. In embodiments, the nanoparticle has a diameter of between 1 and 1000 nm. In embodiments, the nanoparticle has a diameter of between 5 and 100 nm. In embodiments, the nanoparticle has a diameter of between 10 and 50 nm.

In embodiments, the nanoparticle has a diameter of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm.

In embodiments, the nanoparticle has a diameter of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm.

In embodiments, the nanoparticle diameter is a hydrodynamic diameter. In embodiments, the diameter is an average diameter of a sample.

In embodiments, the graft polymer is capable of programmed self-assembly. In embodiments, the programmed self-assembly results in a nanoparticle (e.g., as described herein).

In embodiments, the graft polymer is a probe for DNA recognition. In embodiments, the graft polymer is a probe for nucleic acid recognition. In embodiments, the graft polymer is capable of intracellular gene manipulation (e.g., knockdown, inhibition, reduction). In embodiments, the graft polymer is a capable of RNA manipulation (e.g., knockdown, inhibition, reduction). In embodiments, the graft polymer is a capable of cellular internalization of nucleic acids. In embodiments, the graft polymer is a capable of gene interference. In embodiments, the graft polymer is a capable of theranostics. In embodiments, the graft polymer is a capable of cellular internalization.

Detailed descriptions of exemplary embodiments of the nucleic acid polymer are provided in the examples section below and throughout the present application.

In embodiments, the graft polymer, micelle, amphiphilic block graft copolymer, or nanoparticle is as described herein, including in an aspect, embodiment, example, figure, table, scheme, and claim.

III. Methods of Making Polymers

In an aspect is provided a method of making a graft polymer, the method including: (i) reacting a plurality of oligonucleotide monomers with a polymerization catalyst or initiator, wherein each of the plurality of oligonucleotide monomers includes a polymerizable monomer covalently bound to an oligonucleotide; and (ii) terminating the reacting with a chain terminator or transfer agent.

In embodiments, the graft polymer is a graft polymer described herein (including in an aspect, embodiment, example, figure, table, claim, or scheme). In embodiments, the graft polymer is a brush polymer.

In embodiments, the graft polymer includes a linear backbone covalently bound to a plurality of oligonucleotide branches.

In embodiments, the polymerization catalyst or initiator is a ROMP catalyst. In embodiments, the polymerization catalyst or initiator is a ruthenium catalyst. In embodiments, the ROMP uses a Grubbs' catalyst. In embodiments, the ROMP uses a Mo catalyst. In embodiments, the polymerization catalyst or initiator is a [Mo(=CHBut)(Nar)(OR)2]. In embodiments, the polymerization catalyst or initiator is a transition metal catalyst. In embodiments, the polymerization catalyst or initiator is a transition metal carbine complex catalyst In embodiments, the polymerization catalyst or initiator is a Benzylidene-bis(tricyclohexylphosphine)-dichlororuthenium. In embodiments, the polymerization catalyst or initiator is a [1,3-bis-(2,4,6-trimethylphenyl)-2-imidazolidinylidene]dichloro(phenylmethylene) (tricyclohexylphosphine)ruthenium. In embodiments, the polymerization catalyst or initiator is a Dichloro(o-isopropoxyphenylmethylene)(tricyclohexylphosphine)ruthenium(II). In embodiments, the polymerization catalyst or initiator is a [1,3-Bis-(2,4,6-trimethylphenyl)-2-imidazolidinylidene]dichloro(o-isopropoxyphenylmethylene)ruthenium. In embodiments, the polymerization catalyst or initiator is a third generation Grubbs' catalyst. In embodiments, the polymerization catalyst or initiator is a (IMesH$_2$)(C$_5$H$_5$N)$_2$(Cl)$_2$Ru=CHPh. In embodiments, the polymerization catalyst or initiator is a radical generating compound. In embodiments, the polymerization catalyst or initiator is a free radical compound.

In embodiments, the chain terminator or transfer agent includes a solid support. In embodiments, the chain terminator or transfer agent includes a nanoparticle. In embodiments, the chain terminator or transfer agent includes a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the chain terminator or transfer agent includes a functional moiety. In embodiments, the chain terminator or transfer agent includes a detectable moiety. In embodiments, the chain terminator or transfer agent includes a $^{32}$P, fluorescent dye, electron-dense reagent, enzyme (e.g., as commonly used in an ELISA), biotin, digoxigenin, paramagnetic molecule, paramagnetic nanoparticle, ultrasmall superparamagnetic iron oxide ("USPIO") nanoparticles, USPIO nanoparticle aggregate, superparamagnetic iron oxide ("SPIO") nanoparticle, SPIO nanoparticle aggregate, monochrystalline SPIO, monochrystalline SPIO aggregate, monochrystalline iron oxide nanoparticle, monochrystalline iron oxide, other nanoparticle contrast agent, liposome or other delivery vehicle containing Gadolinium chelate ("Gd-chelate") molecule, Gadolinium, radioisotope, radionuclide (e.g. carbon-1$_1$, nitrogen-13, oxygen-15, fluorine-18, rubidium-82), fluorodeoxyglucose (e.g. fluorine-18 labeled), any gamma ray emitting radionuclids, positron-emitting radionuclide, radiolabeled glucose, radiolabeled water, radiolabeled ammonia, biocolloids, microbubble (e.g. including microbubble shell including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agent (e.g. iohexol, iodixanol, ioversol, iopamidol, ioxilan, iopromide, diatrizoate, metrizoate, ioxaglate), barium sulfate, thorium dioxide, gold, gold nanoparticle, gold nanoparticle aggregate, fluorophore, two-photon fluorophore, or a hapten. In embodiments, the chain terminator or transfer agent includes an ethyl vinyl ether. In embodiments, the chain terminator or transfer agent includes an alkene containing substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the chain terminator or transfer agent includes an alkene bonded to a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the chain terminator or transfer agent includes an alkene containing compound (e.g., also including a function group, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or detectable moiety). In embodiments, the chain terminator or transfer agent includes a moiety selected from:
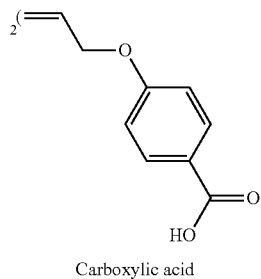
Carboxylic acid
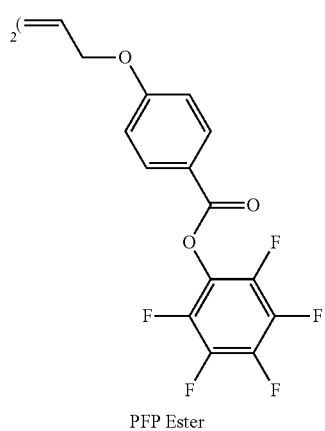
PFP Ester
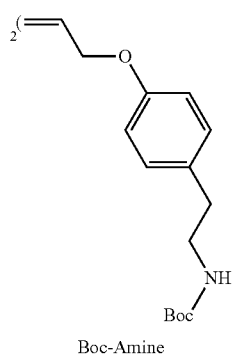
Boc-Amine
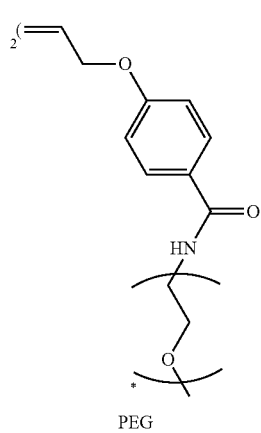
PEG
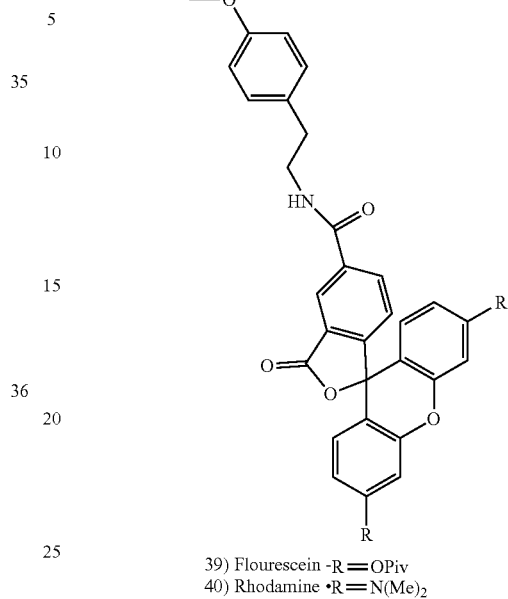
39) Flourescein -R═OPiv
40) Rhodamine •R═N(Me)₂
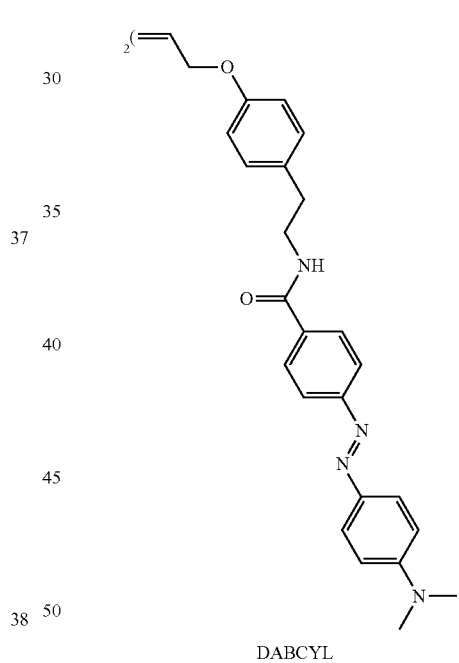
DABCYL
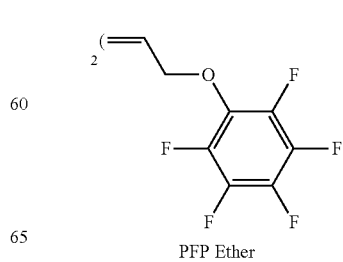
PFP Ether -continued

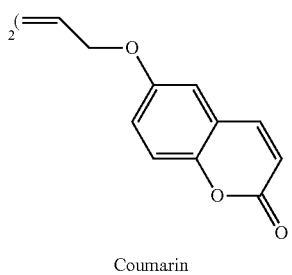

Coumarin

In embodiments, the chain terminator or transfer agent is a solid support. In embodiments, the chain terminator or transfer agent is a nanoparticle. In embodiments, the chain terminator or transfer agent is a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the chain terminator or transfer agent is a functional moiety. In embodiments, the chain terminator or transfer agent is a detectable moiety. In embodiments, the chain terminator or transfer agent includes a $^{32}P$, fluorescent dye, electron-dense reagent, enzyme (e.g., as commonly used in an ELISA), biotin, digoxigenin, paramagnetic molecule, paramagnetic nanoparticle, ultrasmall superparamagnetic iron oxide ("US-PIO") nanoparticles, USPIO nanoparticle aggregate, superparamagnetic iron oxide ("SPIO") nanoparticle, SPIO nanoparticle aggregate, monochrystalline SPIO, monochrystalline SPIO aggregate, monochrystalline iron oxide nanoparticle, monochrystalline iron oxide, other nanoparticle contrast agent, liposome or other delivery vehicle containing Gadolinium chelate ("Gd-chelate") molecule, Gadolinium, radioisotope, radionuclide (e.g. carbon-11, nitrogen-13, oxygen-15, fluorine-18, rubidium-82), fluorodeoxyglucose (e.g. fluorine-18 labeled), any gamma ray emitting radionuclids, positron-emitting radionuclide, radiolabeled glucose, radiolabeled water, radiolabeled ammonia, biocolloids, microbubble (e.g. including microbubble shell including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agent (e.g. iohexol, iodixanol, ioversol, iopamidol, ioxilan, iopromide, diatrizoate, metrizoate, ioxaglate), barium sulfate, thorium dioxide, gold, gold nanoparticle, gold nanoparticle aggregate, fluorophore, two-photon fluorophore, or a hapten. In embodiments, the chain terminator or transfer agent is an ethyl vinyl ether. In embodiments, the chain terminator or transfer agent is an alkene containing substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the chain terminator or transfer agent is an alkene bonded to a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the chain terminator or transfer agent is an alkene containing compound (e.g., also including a function group, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or detectable moiety).

In embodiments, the method includes radical polymerization, controlled radical polymerization, reversible addition-fragmentation chain transfer (RAFT) polymerization, atom transfer radical polymerization (ATRP), ring-opening metathesis polymerization (ROMP), anionic and cationic polymerizations, free radical living polymerization, acyclic diene metathesis polymerization, radiation-induced polymerization, ring-opening olefin metathesis polymerization, polycondensation reactions, or iniferter-induced polymerization. In embodiments, the method employs radical polymerization, controlled radical polymerization, reversible addition-fragmentation chain transfer (RAFT) polymerization, atom transfer radical polymerization (ATRP), ring-opening metathesis polymerization (ROMP), anionic and cationic polymerizations, free radical living polymerization, acyclic diene metathesis polymerization, radiation-induced polymerization, ring-opening olefin metathesis polymerization, polycondensation reactions, or iniferter-induced polymerization.

In embodiments, the method includes ring-opening metathesis polymerization. In embodiments, the method employs ring-opening metathesis polymerization.

In an aspect is provided a method of making an amphiphilic block graft copolymer, the method including: (i) reacting a plurality of oligonucleotide monomers with a polymerization catalyst thereby forming a hydrophilic block portion, wherein each of the plurality of oligonucleotide monomers includes a polymerizable monomer covalently bound to an oligonucleotide; (ii) reacting the hydrophilic block portion with a plurality of hydrophobic monomers and the polymerization catalyst thereby forming the amphiphilic block graft copolymer, wherein each of the plurality of hydrophobic monomers includes the polymerizable monomer covalently bound to a hydrophobic moiety.

In embodiments, the amphiphilic block graft copolymer, oligonucleotide monomers, polymerization catalyst, polymerizable monomer, oligonucleotide, of hydrophobic monomers, and hydrophobic moiety, are as described herein, including in aspects, embodiments, examples, figures, tables, schemes, and claims.

In an aspect is provided a method of making an amphiphilic block graft copolymer, the method including: (i) reacting a plurality of hydrophobic monomers with a polymerization catalyst thereby forming a hydrophobic block portion, wherein each of the plurality of hydrophobic monomers includes a polymerizable monomer covalently bound to a hydrophobic moiety; (ii) reacting the hydrophobic block portion with a plurality of oligonucleotide monomers and the polymerization catalyst thereby forming the amphiphilic block graft copolymer, wherein each of the plurality of oligonucleotide monomers includes the polymerizable monomer covalently bound to an oligonucleotide.

In embodiments, the amphiphilic block graft copolymer, oligonucleotide monomers, polymerization catalyst, polymerizable monomer, oligonucleotide, of hydrophobic monomers, and hydrophobic moiety, are as described herein, including in aspects, embodiments, examples, figures, tables, schemes, and claims.

In embodiments, the method includes radical polymerization, controlled radical polymerization, reversible addition-fragmentation chain transfer (RAFT) polymerization, atom transfer radical polymerization (ATRP), ring-opening metathesis polymerization (ROMP), anionic and cationic polymerizations, free radical living polymerization, acyclic diene metathesis polymerization, radiation-induced polymerization, ring-opening olefin metathesis polymerization, polycondensation reactions, or iniferter-induced polymerization. In embodiments, the method employs radical polymerization, controlled radical polymerization, reversible addition-fragmentation chain transfer (RAFT) polymerization, atom transfer radical polymerization (ATRP), ring-opening metathesis polymerization (ROMP), anionic and cationic polymerizations, free radical living polymerization, acyclic diene metathesis polymerization, radiation-induced polymerization, ring-opening olefin metathesis polymerization, polycondensation reactions, or iniferter-induced polymerization.

In embodiments, the method includes ring-opening metathesis polymerization. In embodiments, the method employs ring-opening metathesis polymerization.

In embodiments, the method is a method described herein, including in an aspect, embodiment, example, figure, table, scheme, and claim.

IV. Methods of Using Polymers

In an aspect is provided a method of internalize nucleic acids (e.g., nucleic acids included in the graft polymer) into a cell including contacting the cell with a graft polymer. In embodiments, the graft polymer is described herein, including in an aspect, embodiment, example, figure, table, scheme, or claim. In embodiments, the nucleic acid is an oligonucleotide as described herein.

In an aspect is provided a method of regulating an mRNA level in a cell including contacting the cell with a graft polymer (e.g., wherein the graft polymer includes nucleic acids capable of regulating an mRNA level). In embodiments, the graft polymer is described herein, including in an aspect, embodiment, example, figure, table, scheme, or claim. In embodiments, regulating is reducing. In embodiments, the method includes contacting the cell with the graft polymer. In embodiments, the nucleic acid included in the graft polymer is complementary to a sequence of the mRNA. In embodiments, the nucleic acid included in the graft polymer hybridizes to the mRNA. In embodiments, the nucleic acid included in the graft polymer selectively hybridizes to the mRNA. In embodiments, the method includes gene interference (e.g., by the nucleic acid). In embodiments, the nucleic acid is an oligonucleotide as described herein.

In an aspect is provided a method of detecting a first nucleic acid in a cell including contacting the cell with a graft polymer (e.g., wherein the graft polymer includes a second nucleic acid capable of hybridizing to the first nucleic acid (e.g., selectively hybridizing)). In embodiments, the graft polymer is described herein, including in an aspect, embodiment, example, figure, table, scheme, or claim. In embodiments, the second nucleic acid included in the graft polymer is complementary to a sequence of the first nucleic acid (e.g., DNA or RNA).

In embodiments, the second nucleic acid is an oligonucleotide as described herein. In embodiments, the graft polymer includes a detectable moiety.

In an aspect is provided a method of detecting a DNA sequence in a cell including contacting the cell with a graft polymer (e.g., wherein the graft polymer includes a nucleic acid capable of hybridizing to the DNA sequence (e.g., selectively hybridizing)). In embodiments, the graft polymer is described herein, including in an aspect, embodiment, example, figure, table, scheme, or claim. In embodiments, the nucleic acid included in the graft polymer is complementary to a portion of the DNA sequence. In embodiments, the nucleic acid is an oligonucleotide as described herein. In embodiments, the graft polymer includes a detectable moiety.

In an aspect is provided a method of detecting a RNA sequence in a cell including contacting the cell with a graft polymer (e.g., wherein the graft polymer includes a nucleic acid capable of hybridizing to the RNA sequence (e.g., selectively hybridizing)). In embodiments, the graft polymer is described herein, including in an aspect, embodiment, example, figure, table, scheme, or claim. In embodiments, the nucleic acid included in the graft polymer is complementary to a portion of the RNA sequence. In embodiments, the nucleic acid is an oligonucleotide as described herein. In embodiments, the graft polymer includes a detectable moiety.

In an aspect is provided a method of purifying a first nucleic acid including contacting the first nucleic acid with a graft polymer (e.g., wherein the graft polymer includes a second nucleic acid capable of hybridizing to the first nucleic acid (e.g., selectively hybridizing)). In embodiments, the graft polymer is described herein, including in an aspect, embodiment, example, figure, table, scheme, or claim. In embodiments, the second nucleic acid included in the graft polymer is complementary to a sequence of the first nucleic acid (e.g., DNA or RNA).

In embodiments, the second nucleic acid is an oligonucleotide as described herein. In embodiments, the graft polymer includes a detectable moiety.

In an aspect is provided a method of administering a nucleic acid to a cell including contacting the cell with a graft polymer, wherein the graft polymer includes the nucleic acid. In embodiments, the graft polymer is described herein, including in an aspect, embodiment, example, figure, table, scheme, or claim. In embodiments, the nucleic acid is an oligonucleotide as described herein.

In an aspect is provided a method of administering a first nucleic acid to a cell including contacting the cell with a graft polymer (e.g., wherein the graft polymer includes a second nucleic acid hybridized to the first nucleic acid (e.g., selectively hybridizing)). In embodiments, the graft polymer is described herein, including in an aspect, embodiment, example, figure, table, scheme, or claim. In embodiments, the second nucleic acid included in the graft polymer is complementary to a sequence of the first nucleic acid (e.g., DNA or RNA). In embodiments, the second nucleic acid is an oligonucleotide as described herein.

In embodiments, the graft polymer is a graft polymer described herein (including in an aspect, embodiment, example, figure, table, claim, or scheme). In embodiments, the graft polymer is a brush polymer. In embodiments, the graft polymer is a block graft copolymer. In embodiments, the graft polymer is a block graft copolymer described herein, including in an aspect, embodiment, example, figure, table, scheme, or claim.

V. Additional Embodiments

1. A graft polymer comprising a linear backbone covalently bound to a plurality of oligonucleotide branches, wherein said graft polymer is assembled by graft-through polymerization of a plurality of oligonucleotide monomers comprising a polymerizable monomer covalently bound to an oligonucleotide, said oligonucleotide thereby forming each of said plurality of oligonucleotide branches.

2. The graft polymer of embodiment 1, wherein said oligonucleotide comprises at least 3 nucleobases and at least 2 different nucleobases.
3. The graft polymer of embodiment 1, wherein said oligonucleotide comprises at least 5 nucleobases and at least 3 different nucleobases.
4. The graft polymer of embodiment 1, wherein said oligonucleotide comprises at least 10 nucleobases and at least 4 different nucleobases.
5. The graft polymer of embodiment 1 comprising at least 3 oligonucleotide branches.
6. The graft polymer of embodiment 1 comprising at least 5 oligonucleotide branches.
7. The graft polymer of embodiment 1 comprising at least 10 oligonucleotide branches.
8. The graft polymer of embodiment 1 having the formula: $R^1$-[M(O)]$_n$—$R^2$ wherein, n is an integer from 2 to 1000; M is the polymerized product of the polymerizable monomer; O is the oligonucleotide; and $R^1$ and $R^2$ are terminal polymer moieties.
9. The graft polymer of embodiment 1, wherein the graft-through polymerization employs ring-opening metathesis polymerization (ROMP).
10. The graft polymer of embodiment 1, wherein the linear backbone is a polynorbornyl chain.
11. A method of making a graft polymer, the method comprising:
(i) reacting a plurality of oligonucleotide monomers with a polymerization catalyst or initiator, wherein each of said plurality of oligonucleotide monomers comprises a polymerizable monomer covalently bound to an oligonucleotide; and
(ii) terminating said reacting with a chain terminator or transfer agent.
12. The method of embodiment 11, wherein the graft polymer comprising a linear backbone covalently bound to a plurality of oligonucleotide branches.
13. The method of embodiment 11, wherein the oligonucleotide comprises at least 3 nucleobases and at least 2 different nucleobases.
14. The method of embodiment 11, wherein the oligonucleotide comprises at least 5 nucleobases and at least 3 different nucleobases.
15. The method of embodiment 11, wherein the oligonucleotide comprises at least 10 nucleobases and at least 4 different nucleobases.
16. The method of embodiment 11, wherein the polymer comprises at least 3 oligonucleotide branches.
17. The method of embodiment 11, wherein the polymer comprises at least 5 oligonucleotide branches.
18. The method of embodiment 11, wherein the polymer comprises at least 10 oligonucleotide branches.
19. The method of embodiment 11, wherein the polymer comprises a linear backbone comprising a polynorbornyl chain.
20. The method of embodiment 11, wherein the polymer has the formula: $R^1$-[M(O)]$_n$—$R^2$ wherein, n is an integer from 2 to 1000; M is the polymerized product of the polymerizable monomer; O is the oligonucleotide; and $R^1$ and $R^2$ are terminal polymer moieties.
21. The method of one of embodiments 11 to 20, comprising radical polymerization, controlled radical polymerization, reversible addition-fragmentation chain transfer (RAFT) polymerization, atom transfer radical polymerization (ATRP), ring-opening metathesis polymerization (ROMP), anionic and cationic polymerizations, free radical living polymerization, acyclic diene metathesis polymerization, radiation-induced polymerization, ring-opening olefin metathesis polymerization, polycondensation reactions, or iniferter-induced polymerization.
22. The method of one of embodiments 11 to 20, comprising ring-opening metathesis polymerization.
23. An amphiphilic block graft copolymer comprising a linear backbone covalently bound to a plurality of oligonucleotide branches and a plurality of hydrophobic side chains, wherein: said plurality of oligonucleotide branches form a hydrophilic block portion of said amphiphilic graft copolymer and said hydrophobic side chains form a hydrophobic block portion of said amphiphilic graft copolymer; said graft copolymer is assembled by graft-through polymerization of a plurality of oligonucleotide monomers and a plurality of hydrophobic monomers, wherein each of said plurality of oligonucleotide monomers comprises a polymerizable monomer covalently bound to an oligonucleotide, said oligonucleotide thereby forming each of said plurality of oligonucleotide branches; and each of said plurality of hydrophobic monomers comprises said polymerizable monomer covalently bound to a hydrophobic moiety, said hydrophobic moiety thereby forming each of said plurality of hydrophobic side chains.
24. The amphiphilic block graft copolymer of embodiment 23, wherein said oligonucleotide comprises at least 3 nucleobases and at least 2 different nucleobases.
25. The amphiphilic block graft copolymer of embodiment 23, wherein said oligonucleotide comprises at least 5 nucleobases and at least 3 different nucleobases.
26. The amphiphilic block graft copolymer of embodiment 23, wherein said oligonucleotide comprises at least 10 nucleobases and at least 4 different nucleobases.
27. The amphiphilic block graft copolymer of embodiment 23 comprising at least 3 oligonucleotide branches.
28. The amphiphilic block graft copolymer of embodiment 23 comprising at least 5 oligonucleotide branches.
29. The amphiphilic block graft copolymer of embodiment 23 comprising at least 10 oligonucleotide branches.
30. The amphiphilic block graft copolymer of one of embodiments 23 to 29, wherein said hydrophobic moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.
31. The amphiphilic block graft copolymer of one of embodiments 23 to 29, wherein said hydrophobic moiety is an unsubstituted benzyl.
32. The amphiphilic block graft copolymer of embodiment 23 having the formula: $R^1$-[M(O)]$_n$-[M(P)]$_m$—$R^2$ or $R^1$-[M(P)]$_m$-[M(O)]$_n$—$R^2$ wherein, n is an integer from 2 to 1000; m is an integer from 2 to 1000; M is the polymerized product of the polymerizable monomer; O is the oligonucleotide; P is the hydrophobic moiety; and $R^1$ and $R^2$ are terminal polymer moieties.
33. A micelle comprising the amphiphilic block graft copolymer of one of embodiments 23 to 32.
34. The micelle of embodiment 33, having a diameter of between about 1 and about 1000 nm.
35. The micelle of embodiment 33, having a diameter of between about 5 and about 100 nm.
36. The micelle of embodiment 33, having a diameter of between about 10 and about 50 nm.

37. A nanoparticle comprising the amphiphilic block graft copolymer of one of embodiments 23 to 32.

38. The nanoparticle of embodiment 37, wherein said nanoparticle is a spherical nanoparticle.

39. The nanoparticle of one of embodiments 37 to 38, having a diameter of between about 1 and about 1000 nm.

40. The nanoparticle of one of embodiments 37 to 38, having a diameter of between about 5 and about 100 nm.

41. The nanoparticle of one of embodiments 37 to 38, having a diameter of between about 10 and about 50 nm.

42. A method of making an amphiphilic block graft copolymer, the method comprising:
(i) reacting a plurality of oligonucleotide monomers with a polymerization catalyst thereby forming a hydrophilic block portion, wherein each of said plurality of oligonucleotide monomers comprises a polymerizable monomer covalently bound to an oligonucleotide;
(ii) reacting said hydrophilic block portion with a plurality of hydrophobic monomers and said polymerization catalyst thereby forming said amphiphilic block graft copolymer, wherein each of said plurality of hydrophobic monomers comprises said polymerizable monomer covalently bound to a hydrophobic moiety.

43. The method of embodiment 42, wherein the oligonucleotide comprises at least 3 nucleobases and at least 2 different nucleobases.

44. The method of embodiment 42, wherein the oligonucleotide comprises at least 5 nucleobases and at least 3 different nucleobases.

45. The method of embodiment 42, wherein the oligonucleotide comprises at least 10 nucleobases and at least 4 different nucleobases.

46. The method of embodiment 42, wherein the amphiphilic block graft copolymer comprises at least 3 oligonucleotide branches.

47. The method of embodiment 42, wherein the amphiphilic block graft copolymer comprises at least 5 oligonucleotide branches.

48. The method of embodiment 42, wherein the amphiphilic block graft copolymer comprises at least 10 oligonucleotide branches.

49. The method of embodiment 42, wherein the amphiphilic block graft copolymer comprises a linear backbone comprising a polynorbornyl chain.

50. The method of embodiment 42, wherein the amphiphilic block graft copolymer of embodiment 23 has the formula: $R^1$-[M(O)]$_n$-[M(P)]$_m$—$R^2$ wherein, n is an integer from 2 to 1000; m is an integer from 2 to 1000; M is the polymerized product of the polymerizable monomer; O is the oligonucleotide; P is the hydrophobic moiety; and $R^1$ and $R^2$ are terminal polymer moieties.

51. The method of one of embodiments 42 to 50, comprising atom transfer radical polymerization (ATRP), ring-opening metathesis polymerization (ROMP), anionic and cationic polymerizations, free radical living polymerization, radiation-induced polymerization, ring-opening olefin metathesis polymerization, polycondensation reactions, or iniferter-induced polymerization.

52. The method of one of embodiments 42 to 50, comprising ring-opening metathesis polymerization.

53. A method of making an amphiphilic block graft copolymer, the method comprising:
(i) reacting a plurality of hydrophobic monomers with a polymerization catalyst thereby forming a hydrophobic block portion, wherein each of said plurality of hydrophobic monomers comprises a polymerizable monomer covalently bound to a hydrophobic moiety;
(ii) reacting said hydrophobic block portion with a plurality of oligonucleotide monomers and said polymerization catalyst thereby forming said amphiphilic block graft copolymer, wherein each of said plurality of oligonucleotide monomers comprises said polymerizable monomer covalently bound to an oligonucleotide.

54. The method of embodiment 53, wherein the oligonucleotide comprises at least 3 nucleobases and at least 2 different nucleobases.

55. The method of embodiment 53, wherein the oligonucleotide comprises at least 5 nucleobases and at least 3 different nucleobases.

56. The method of embodiment 53, wherein the oligonucleotide comprises at least 10 nucleobases and at least 4 different nucleobases.

57. The method of embodiment 53, wherein the amphiphilic block graft copolymer comprises at least 3 oligonucleotide branches.

58. The method of embodiment 53, wherein the amphiphilic block graft copolymer comprises at least 5 oligonucleotide branches.

59. The method of embodiment 53, wherein the amphiphilic block graft copolymer comprises at least 10 oligonucleotide branches.

60. The method of embodiment 53, wherein the amphiphilic block graft copolymer comprises a linear backbone comprising a polynorbornyl chain.

61. The method of embodiment 53, wherein the amphiphilic block graft copolymer of embodiment 23 has the formula: $R^1$-[M(P)]$_m$-[M(O)]$_n$—$R^2$ wherein, n is an integer from 2 to 1000; m is an integer from 2 to 1000; M is the polymerized product of the polymerizable monomer; O is the oligonucleotide; P is the hydrophobic moiety; and $R^1$ and $R^2$ are terminal polymer moieties.

62. The method of one of embodiments 53 to 61, comprising atom transfer radical polymerization (ATRP), ring-opening metathesis polymerization (ROMP), anionic and cationic polymerizations, free radical living polymerization, radiation-induced polymerization, ring-opening olefin metathesis polymerization, polycondensation reactions, or iniferter-induced polymerization.

63. The method of one of embodiments 53 to 61, comprising ring-opening metathesis polymerization.

VI. EXAMPLES

The following examples are offered to illustrate, but not to limit, the claimed invention.

Example 1: Methods of Making Poly(oligonucleotides)

This example describes an efficient synthetic strategy for the incorporation of nucleic acids into particle and polymer-based materials. This work is published in James et ah, "Poly(oligonucleotide)," *J Am Chem Soc*, in press, and Thompson et al., "Labelling Polymers and Micellar Nanoparticles via Initiation, Propagation and Termination with ROMP," *Polym Chem*, 2014 March 21; 5(6): 1954-1964, the contents of which are hereby incorporated in their entirety for all purposes.

Here we report the preparation of poly(oligonucleotide) brush polymers and amphiphilic brush copolymers from nucleic acid monomers via graft-through polymerization.

We describe the polymerization of PNA-norbornyl monomers to yield poly-PNA (polypeptide nucleic acid)) via ing-opening metathesis polymerization (ROMP) with the initiator, (IMesFL)-(C$_5$H$_5$N)$_2$(Cl)$_2$RuCHPh.[1] In addition, we present the preparation of poly-PNA nanoparticles from amphiphilic block copolymers and describe their hybridization to a complementary single-stranded DNA (ssDNA) oligonucleotide.

Figure 1B:
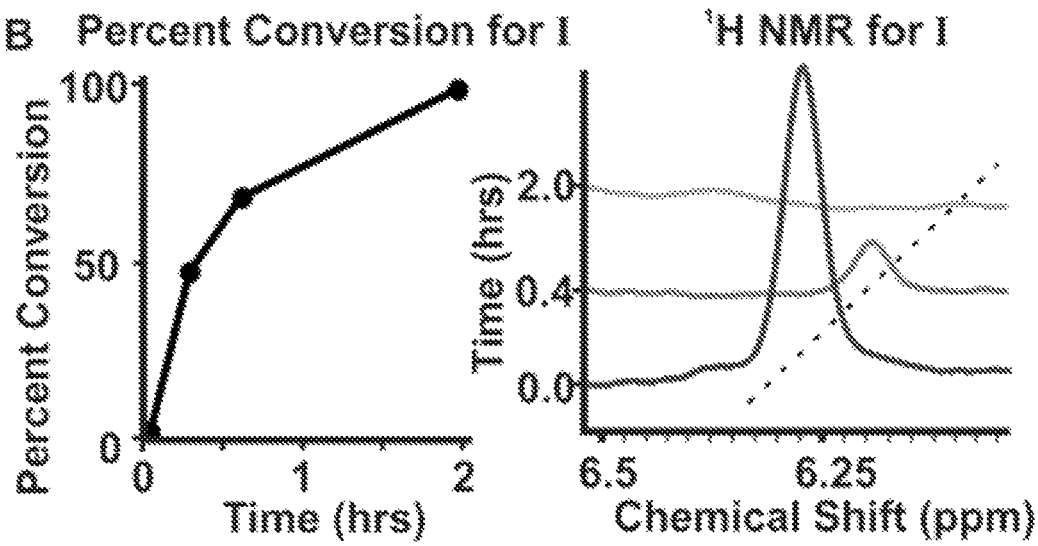
Figure 1C:
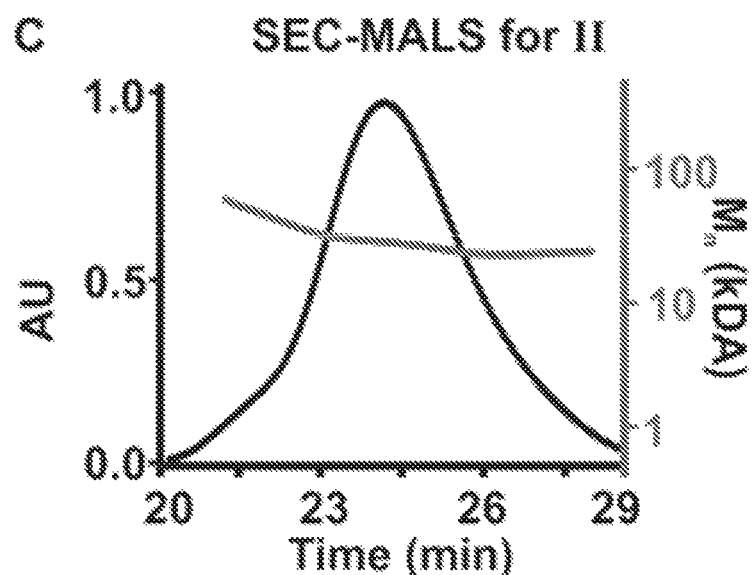

The display of chemical functionality in a multivalent fashion on surfaces and particles and as brushes on polymer backbones is a common theme in nature as well as for synthetic systems.[2-4] Such systems take advantage of the unique properties that arise when monomeric species are incorporated into a densely packed three-dimensional (3D) architecture. Here we describe the preparation of polymeric nucleic acids wherein single-stranded sequences of peptide nucleic acids (PNAs) are incorporated as polymer brushes via graft-through polymerization using the ROMP initiator (IMesH$_2$)—(C$_5$H$_5$N)$_2$(Cl)$_2$RuCHPh (FIGS. 1A-1C). Nucleic acids, both natural and synthetic, standout as the quintessential carriers of chemical information stored as specific sequences of bases positioned along a backbone.[4-7] As such, synthetic oligonucleotides and nucleic acid bioconjugates are powerful tools in a range of fields including in biotechnology (e.g., PCR)[8,9] and in materials science as programmable structural synthons[10-16] and as aptamers selected by in vitro evolution.[17-21] In each application the nucleic acid functions to enrich a chemical system with information, facilitating predictable interactions with complementary sequences, or with other molecules including enzymes, proteins, and small molecules.[1Ω23-25] We reasoned that an approach allowing the graft-through polymerization of an oligonucleotide sequence would provide a powerful new tool for the multivalent display of chemical information on a synthetic template.

There have been extensive efforts to prepare nucleic acid inspired synthetic polymers involving the direct polymerization of appropriately modified monomers, generating synthetic polymers with single nucleobases as sidechains.[26-31] Although this approach allows the integration of purine and pyrimidine bases onto a synthetic backbone, it does not allow the incorporation of sequences containing multiple bases and thus does not result in informational polymeric systems. In addition there are an increasing number of examples of oligonucleotide-polymer bioconjugates in the literature, each reliant upon post-polymerization conjugation reactions.[32-34] These approaches, shown in Scheme 1, seek to fix recognition elements natural to DNA and RNA along a synthetic polymer or polymeric nanoparticle template and have found use in an array of arenas including the programmed assembly of nanoparticles,[2,35-37] in delivery vehicles,[5,38-40] and as effective DNA-probes.[34,41,42] Furthermore, the function of these materials is intrinsically governed by the information within the nucleic acid sequence itself as well as the dense and multivalent 3D array induced byte polymer scaffold. Indeed, function dictated by 3D biomolecular display is not unique to nucleic acids, rather this concept extends to all classes of biomolecules, most effectively demonstrated in the past with peptides and proteins.[3,43-47] Strategies for the polymerization of (graft-through) and polymerization from (graft-from) proteins and peptides have been used to build macromolecules through sequential addition of monomers to a growing chain, taking advantage of polymerization catalyst proficiency and avoiding kinetically unfavorable conjugations (graft-to) between multiple large macromolecules.[48-54] However, unlike for other bio-molecules (saccharides,[55,57] peptides,[58] and proteins[59,60]), there are no examples of graft-through polymerization and few examples of graft-from polymerization of nucleic acids.[61,62] Therefore, despite their promise, polymer bioconjugates of true nucleic acid sequences have been mostly limited to those prepared via post-polymerization modification and hence are difficult to reproduce and suffer from incomplete incorporation of the nucleic acid at each position of the polymer (FIGS. 4A-4B).

In order to avoid shortcomings associated with post-polymerization modification reactions, a nucleic acid monomer capable of undergoing direct graft-through polymerization was synthesized. Initial studies attempting direct-polymerization of DNA-based monomers via ROMP were met with limited success. Therefore, a PNA-based monomer was chosen as an ideal target for this study for three key reasons: (1) PNA can be prepared in milligram to gram quantities via standard peptide bond-forming reactions on solid support; (2) PNA is soluble in DMF making it readily compatible with (IMesH$_2$)- (C$_5$H$_5$N)$_2$(Cl)$_2$RuCHPh (FIGS. 1A-1C for structure); and (3) we hypothesized that the neutral N-(2-amino-ethyl)-glycine back-bone would be more compatible with the ruthenium-based catalyst than the polyanionic phosphate backbone of DNA. The 10-base PNA sequence (FIGS. 1A-1C) was designed to discourage self-hybridization, while providing a sufficient number of bases for efficient hybridization with a comple-mentary sequence of DNA at room temperature. Moreover, this 10-base sequence represents a sequence encoded with each of the four letters of the genetic alphabet and enough information to communicate specifically with other nucleic acids and proteins, a function not possible via the polymer Polymerization of a single purine of pyrimidine monomer (as in FIG. 4B). After the complete PNA sequence was prepared, N—(glycine)-cis-5-norbornene-exo-dicarboximide was coupled to the N-terminus while on solid support. The PNA norbornene monomer (PNA-Nb) was then cleaved and deprotected from the solid support using TFA:cresol (80:20), purified by HPLC, and the mass confirmed by ESI-MS. Following HPLC purification, PNA-Nb was lyophilized to afford a white powder.

For polymerization studies, PNA-Nb was resuspended in dry, degassed N,N-dimethylformamide-d7 in a J. Young NMR tube in a glovebox. An appropriate amount of ruthenium initiator was added to the solution, and the disappearance of the norbornene olefin resonance was then monitored by $^1$H NMR. Complete disappearance of the monomelic olefin peak indicated complete polymerization of PNA-Nb into poly-PNA. A series of experiments were carried out to determine reproducibility of polymerization reactions with respect to both the preparation of homopolymers as well as block copolymers (Table 1).

TABLE 1

Polymers and Copolymers of PNA with Monomers Shown in FIG. 2.

| polymer | mon$_1$[a] | mon$_2$[c] | m[d] | n[d] | % con.[e] |
|---|---|---|---|---|---|
| I    | PNA-Nb (10.1)[b] | —            | 10 | —  | 99 |
| II   | 1 (35:1)         | PNA-Nb (5:1) | 35 | 5  | 97 |
| III  | PNA-Nb (5:1)     | —            | 5  | —  | 97 |
| IV   | 1 (30:1)         | PNA-Nb (7.5:1) | 30 | 5  | 65 |
| V    | 1 (30:1)         | PNA Nb (7.5:1) | 30 | 5  | 65 |
| VI   | 1 (30:1)         | PNA-Nb (7.5:1) | 30 | 6  | 79 |
| VII  | 1 (36:1)         | PNA-Nb (9:1) | 35 | 8  | 88 |
| VIII | 1 (36:1)         | PNA-Nb (18:1) | 35 | 16 | 87 |
| IX   | 2 (36:1)         | PNA Nb (9:1) | 33 | 7  | 74 |
| X    | 3 (36:1)         | FNA-Nb (9:1) | 41 | 5  | 56 |

[a]Indicates indentity of monomer polymerized first (degree of polymerization, DP = m).
[b]Ratios shown indicate monomer to initiator rate or intended DP.
[c]Indicates identity of monomer polymerized second (DP = n).
[d]Observed degree of polymerization of mon$_1$ (m) or mon$_2$ (n).
[e]Percent conversion of PNA-Nb determined by $^1$H NMR.

For PNA homopolymers, degrees of polymerization of 5 (polymer I) and 10 (polymer III) were targeted with complete consumption of PNA-Nb confirmed by ¾ NMR for both reactions. In preparation of a PNA-containing block copolymer, a phenyl-functionalized norbornene (1) was polymerized as the first block followed by PNA-Nb incorporated as the second block (as shown in polymer II (FIGS. 1A-1C, Table 1). To achieve this, PNA-Nb was added to the living phenyl polymer chain, and the disappearance of the norbornene olefin of PNA-Nb was monitored by $^1$H NMR. SEC-MALS confirmed molecular weights for the resulting species. Having established that PNA-Nb could be successfully polymerized into block copolymers, we sought to assess the reproducibility of these reactions by attempting to synthesize block copolymers of identical composition. Using a live ruthenium catalyst on a phenyl homopolymer with a degree of polymerization of 30, three separate but identical reactions were set up in which the attempted degree of polymerization of the PNA monomer was 7.5 (Table 1, polymers IV-VI). The degree of polymerization of the PNA block ranged from 5 to 6 (60-80% completion), indicating a good degree of reproducibility and predictability for these reactions. In addition, higher degrees of polymerization could be achieved for this type of block copolymer as illustrated by the preparation of polymers VII and VIII (Table 1). To examine the compatibility of PNA-Nb polymerization with other block copolymer systems, an oligoethylene glycol functionalized norbornene (2) and a quaternary amine-functionalized norbornene (3) were synthe-sized as monomers for incorporation into block copolymer scaffolds as the initial block. The resulting block polymers (IX and X in Table 1) showed percent conversions of PNA-Nb comparable to the phenyl-based block copolymers, with the amine-functionalized system demonstrating the lowest percent conversion. Given the slight variation in PNA-Nb percent conversion between these three different block copolymer systems (VII, IX and X in Table 1), the identity of the non-PNA block may dictate PNA conversion efficiency and should be taken into consideration for future studies. To assess the DNA-binding capability of these systems, block copolymer II was chosen. The assembly of II to generate spherical nanoparticles was achieved by dissolving in DMSO and then dialyzing into aqueous solution.[63] The resulting nanoparticle (PNA-NP) was characterized by DLS and TEM (FIGS. 3A-3E). DLS data support the formation of an aggregated species in solution. TEM reveals nanoparticles on the order of 20 nm in diameter. The melting temperature ($T_m$) of PNA-NP hybridized with its complementary DNA sequence was determined to be 58. 1° C., an ~8° C. increase over an identical, nonparticulate, PNA sequence. These melting data suggest cooperative binding and accessible PNA forming the shell of the nanoparticles. In support of this model, we conducted a molecular dynamics simulation of PNA-NP[64-66] assembled from 60 amphiphiles giving a structure that equilibrated into a spherical particle ~21 nm in diameter. Polynorbornyl chains packed well to form a compact hydrophobic core largely protected from contact with water. The simulations show the hydrophilic PNA chains solvated in water forming the shell of the micelles.

In summary, we have shown that one can prepare nucleic acid brush polymers and amphiphilic brush copolymers by direct polymerization via graft-through polymerization of a nucleic acid. To our knowledge, this is the first example of a polymer-nucleic acid bioconjugate generated via direct polymerization of an oligonucleotide monomer. In addition, these materials show cooperative hybridization to complementary DNA oligonucleotides. We believe this type of approach provides an efficient synthetic strategy for the incorporation of nucleic acids into particle and polymer-based materials. The interest in doing so is driven by potential applications including the facile preparation of materials for affinity purification of DNA,[67,68] gene and nucleic acid deliveryto cells,[5,38-40,69-72] and in the development of materialscapable of programmed self-assembly.[12-16,73-77]

1. General Methods

All reagents were purchased from commercial sources and used without further purification unless otherwise indicated. N-phenyl-cis-5-norbornene-exo-dicarboximide [Ku, T. H.; Chien, M. P.; Thompson, M. P.; Sinkovits, R. S.; Olson, N. PL; Baker, T. S.; Gianneschi, N. C. *J. Am. Chem. Soc.*, 2011, 133, 8392], 2-(2,5,8,1 1-tetraoxatridecan-13-yl)-3a,4,7,7a-tetrahydro-1 H-4,7-methanoisoindole-1,3(2 H)-dione [Thompson, M. P.; Randolph, L. M.; James, C. R.; Davalos, A. N.; Hahn, M. E.; Gianneschi, N. C. *Polym. Chem.*, 2014, 5, 1954], N-benzyl-2-(1,3-dioxo-1,3,3a,4,7, 7a-hexahydro-2 H-4,7-epoxyisoindol-2-yl)-N,N-dimethylethan-1-aminium [Rankin, D. A.; P'Pool, S. J.; Schanz, H.-J.; Lowe, A. B. *J. Polym. Set A Polym. Chem.*, 2007, 45, 2113], (peg)N-(glycine)-c«-5-norbornene-exo-dicarboximide [Conrad, R. M.; Grubbs, R. H. *Angew. Chem. Int. Edit.*, 2009, 48, 8328] were prepared as described. All PNA sequences were made using NovaPEG Rink Amide resin, purchased from EMD Millipore, with a loading of 0.49 mmol/g and a swelling volume of 8.8 mL/g in $CH^2C$ 1$^2$. The synthesis of all PNA oligomers used Fmoc/Bhoc protected monomers (Fmoc-A(Bhoc)-aeg-OH, Fmoc-C(Bhoc)-aeg-OH, Fmoc-G(Bhoc)-aeg-OH, and Fmoc-T-aeg-OH) purchased from Panagene. PNA sequences were manually synthesized in house using standard solid-phase peptide synthesis conditions. RP-HPLC analysis of PNAs was performed on a Hitachi-Elite LaChrom L-2130 pump with a step-wise gradient. Detection was at 260 nm using an in-line UV-Vis detector (Hitachi-Elite LaChrom L-2420). For analysis, an analytical scale Phenomenex Jupiter 4μη Proteo 90A column (150×4.60 mm) was utilized. For purification, a semi-preparative Phenomenex Jupiter 4μη Proteo 90A column (250×10.0 mm) was utilized. Mass spectra were obtained at the UCSD Chemistry and Biochemistry Molecular Mass Spectrometry Facility. Low-resolution mass spectra were obtained using a Thermo LCQdeca mass spectrometer. Concentrations of oligonucleotides and peptide nucleic acids were determined using a Thermo Scientific NanoDrop 2000c spectrophotometer. Modified $2^{nd}$ Generation Grubbs' Ruthenium initiator (IMesH$_2$)(C$_5$H$_5$N)$_2$(Cl)$_2$Ru=CHPh was prepared as described by Sanford et. al. [Sanford, M. S.; Love, J. A.; Grubbs, R. H. *Organometallics*, 2001, 20, 5314] Sealed ampules of (CD$_3$)$_2$NCOD (DMF-d$_7$) used in polymerization reactions was purchased from Cambridge Isotope Laboratories Inc. and was distilled and degassed with 3 freeze-pump-thaw cycles prior to use. $^1$H (400 MHz) NMR spectra were recorded on a Varian Mercury Plus spectrometer. Chemical shifts ($^1$H) are reported in δ (ppm) relative to the DMF-d$_7$ residual proton peaks (8.03, 2.92, and 2.75 ppm). Polymer molecular weight and dispersity were determined via size-exclusion chromatography (Phenomenex Phenogel 5μη10, 1K-75K, 300×7.80 mm in series with a Phenomex Phenogel 5n1j 10, 10K-1000K, 300×7.80 mm (mobile phase: 0.05 M LiBr in DMF)) using a Hitachi-Elite LaChrom L-2130 pump equipped with a DAWN HELEOS multi-angle light scattering (MALS) detector (Wyatt Technology) and a refractive index detector (Hitachi L-2490) normalized to a 30,000 g/mol polystyrene standard. The dn/dc values used were 0.179.

Hydrodynamic diameter (Dh) of nanoparticles was measured via DLS using a DynaPro NanoStar (Wyatt Technology). TEM samples were deposited on carbon/formvar-coated copper grids (Ted Pella Inc.), stained with 1% w/w uranyl acetate, and imaged using a Technai G2 Sphera operating at an accelerating voltage of 200 kV. Complementary and non-complementary DNA sequences were purchased from Integrated DNA Technologies (purified by HPLC, confirmed by ESI-MS). DNA melting temperature analysis was conducted using a Cary Series 100 UV-Vis spectrophotometer equipped with a Cary temperature controller.

2. PNA Monomer Synthesis raphy Column, purchased from Bio-Rad Laboratories. Unless otherwise stated the following standard protocol was used:

1) Swelling of the NovaPEG Rink Amide resin in CH$_2$Cl$_2$ for 2 hours. Deprotection of the resin is not required as it is sold without protecting groups.
2) Resin is washed with a steady flow of DMF (30 seconds) followed by a steady flow of with CH$_2$Cl$_2$ (30 seconds).
3) Activation of PNA monomer (5 equivalents with respect to total active sites on the resin) occurred by addition of 4.5 equivalents N,N,N,N-Tetramethyl-O-(7-azabenzotriazol-1-yl)uronium hexafluorophosphate (HATU) (slightly less equivalents were used to ensure total activation of monomer with HATU and to prevent occurrence of unreacted HATU from reacting with resin amine or unprotected amines in the growing PNA sequence. Unprotected amines can form a guanidine moiety with HATU that blocks further elongation) and 10 equiv. of diisopropylethylamine (DIPEA) in DMF. The final concentration of the monomer was 0.2M in DMF. Monomer activation was allowed to proceed for 10 minutes before being added to the resin.
4) A steady stream of N$_2$(g) was bubbled through the peptide synthesis vessel while coupling occurred. Coupling time was 60 minutes.
5) Upon completion of coupling, the activating solution was vacuumed off the resin, and the resin was washed with a steady stream of DMF for 30 seconds (3 times), followed by CH$_2$Cl$_2$ for 30 seconds (3 times). No capping steps were necessary for the PNA sequences chosen.
6) Deprotection of the Fmoc was done using a solution of 20% piperidine in DMF for 5 minutes.

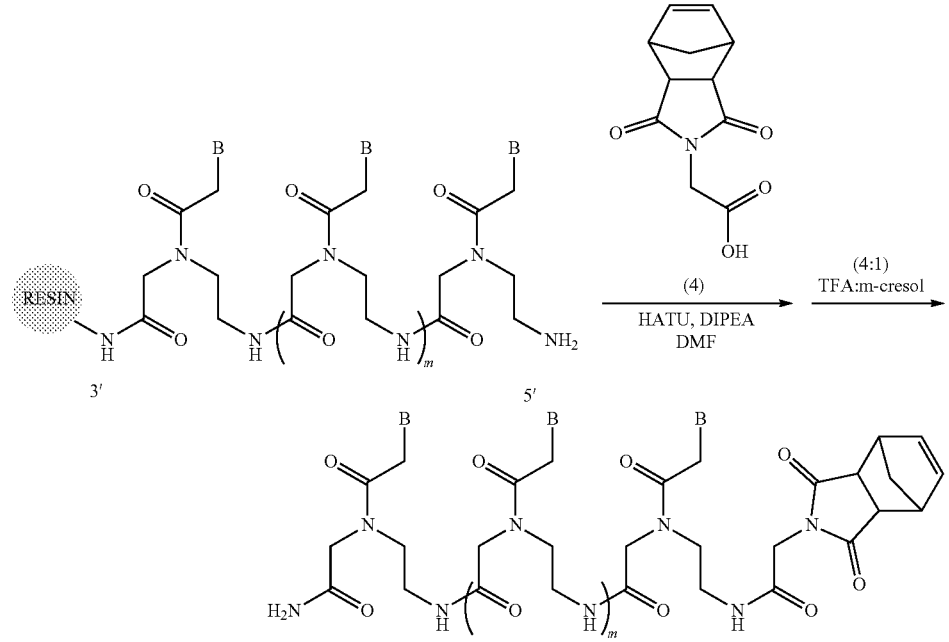

All PNA sequences were manually synthesized. All reactions and washes of the resin were performed in a fritted glass peptide synthesis vessel, with the exception of the cleavage and deprotection of the oligomer from the resin, which was done in a polypropylene Poly-Prep Chromatog- 7) Steps 2-6 were repeated until chain length was complete.
8) Following the removal of the final Fmoc group, and subsequent washings of the resin with DMF and CH2Cl2, the HATU-activated carboxylic acid-substituted norbornene (4) was added and a steady stream of N$_2$(g) bubbled through the vessel for 60 minutes (the carboxylic acid-substituted norbornene was activated using the same protocol used for the PNA monomers in step 3).

9) Upon completion of coupling, the activating solution was vacuumed off the resin, and the resin was washed with a steady stream of DMF for 30 seconds (3 times), followed by CH2Cl2 for 30 seconds (3 times).

10) Step 8 was repeated (carboxylic acid-substituted norbornene (1) coupling to the resin).

11) Upon completion of coupling, the activating solution was vacuumed off the resin, and the resin was washed with a steady stream of DMF for 30 seconds (3 times), followed by CH2Cl2 for 30 seconds (3 times).

12) The resin was dried under vacuum for several hours.

13) The removal the Bhoc protecting groups and cleavage from the resin was accomplished by treatment with a solution of TFA:m-cresol (80:20) for 90 minutes. The cleavage was performed in a polypropylene Poly-Prep Chromatography Column. After cleavage, the TFA: cresol solution was separated from the resin by centrifugation. The TFA:cresol solution was then evaporated until near dryness by applying a stream of air to the solution for several hours.

14) The crude PNA-norbornene oligomer crashed out of the TFA:cresol solution upon addition of 5 equivalents of diethyl ether with respect to the TFA:m-cresol solution, yielding an off-white powdery solid.

15) Reverse-phase preparatory HPLC was used to purify all sequences, and masses were confirmed by Matrix Assisted Laser Desorption-Time of Flight (MALDI-TOF)

3. HPLC Purification of PNA Sequences

RP-HPLC analysis of PNA was performed using 0.1% TFA/H$_2$O as solvent A, and 0.1% TFA/CH$_3$CN as solvent B. Gradient: 0% solvent B in 2 min, 0% to 5% solvent B in 3 min, 5% to 20% solvent B in 10 min, and 20% to 100% solvent B in 20 min.

4. Homopolymer Synthesis via Ring-Opening Metathesis Polymerization (ROMP)

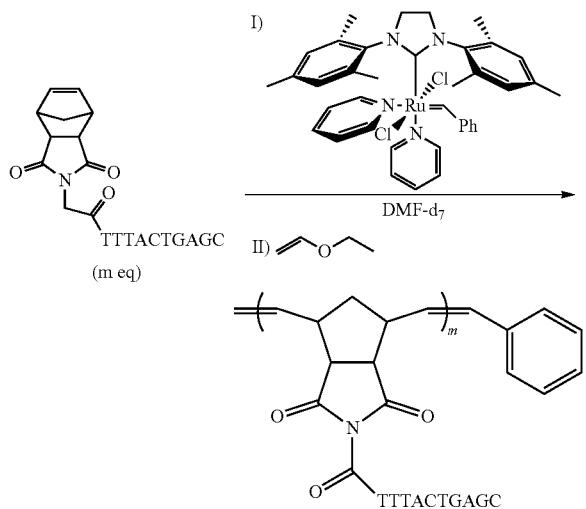

PNA-Nb monomer (CGAGTCATTT-Nb) was polymerized via ROMP using Grubbs' modified 2$^{nd}$ generation catalyst (IMesH$_2$)(C$_5$HSN)$_2$(Cl)$_2$Ru=CHPh in a glove box. The PNA-Nb monomer (3 mg, 1μηol) in a J-Young NMR tube was dissolved in 250 pL of anhydrous and degassed DMF-d$_7$. The tube was removed from the glove box and a ¾ NMR spectrum (t=0) was taken. The tube was returned to the glove box and the catalyst (0.2μηol or 0.1μηol) was added to the reaction solution. $^1$H NMR spectra were recorded at the indicated time points until consumption of the olefin. It was observed that as the PNA monomer olefin disappeared, the corresponding DMF-d$_7$ solutions became cloudy, and that the polyolefin peaks typically seen at ~5.5 ppm were absent, indicating that the resultant polymer had limited to no solubility in DMF. In addition, the homopolymers were insoluble in H$_2$O, MeOH, and DCM solutions and had limited solubility in a solution of 0.05 M LiBr in DMF. Upon consumption of the olefin, the tube was returned to the glove box and termination agent ethyl vinyl ether (100 μL, excess) was added to the reaction mixture, and the mixture was allowed to sit at room temperature for 20 minutes. The crude polymer was precipitated from cold methanol and analyzed by SEC-MALS.

Figure 5:
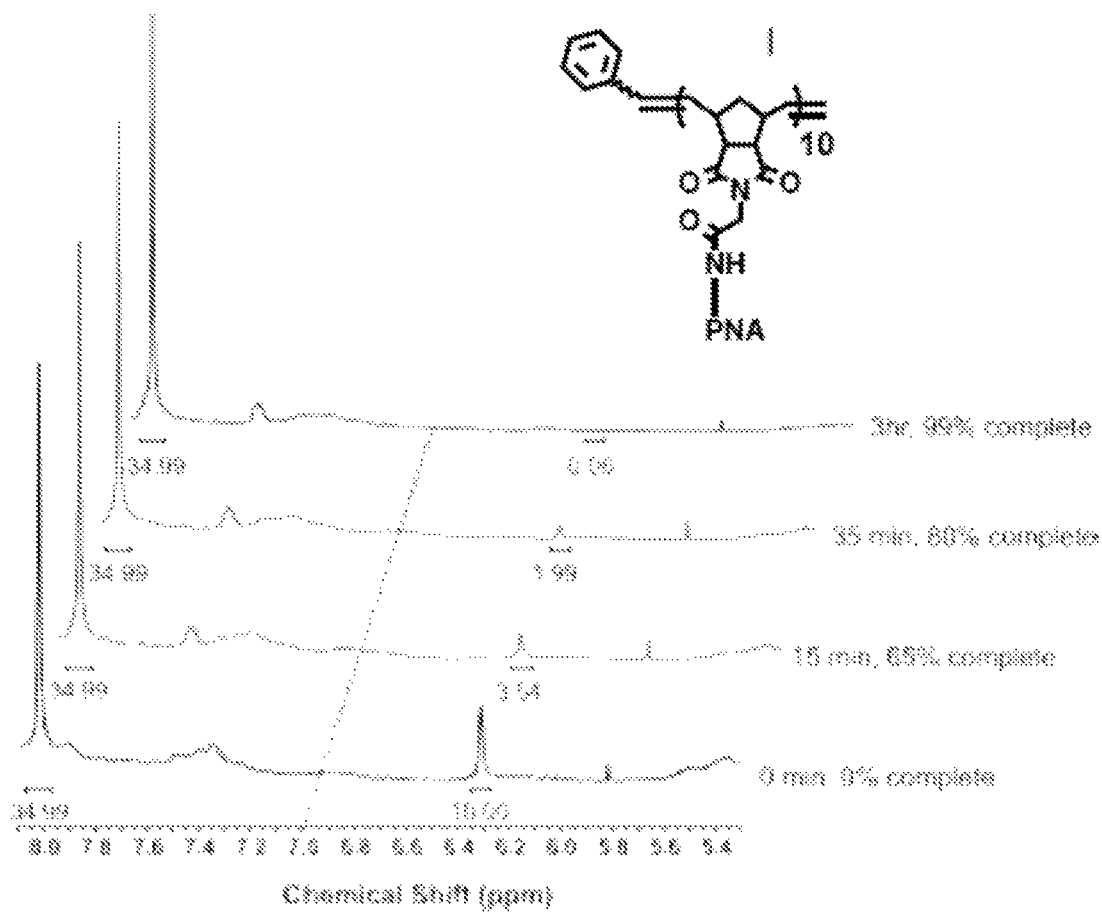
FIG. 5. 1H NMR spectra for I.

5. ROMP timescale[1]!I NMR for homopolyPNAs:

FIG. 5. Integrations based on 10 eq of PNA olefin at t=0. DMF residual proton is then integrated accordingly for the ensuing time points.

Figure 6:
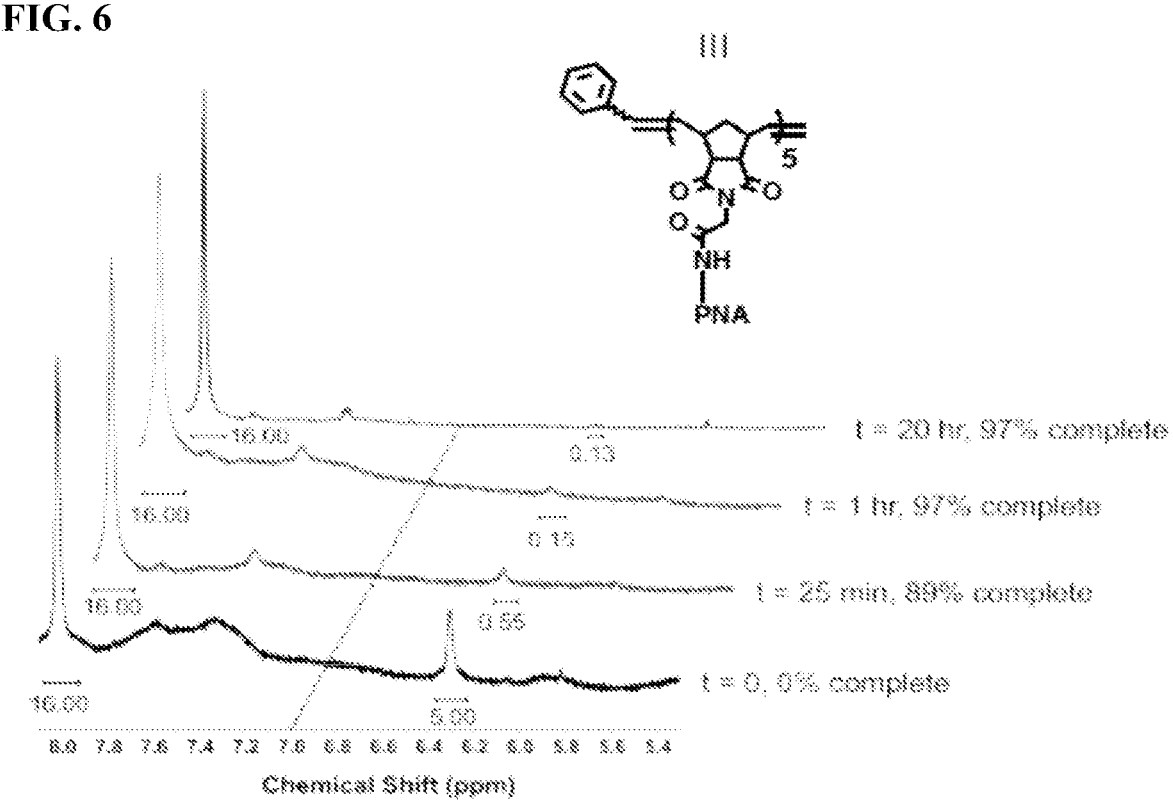
FIG. 6. 1H NMR spectra for III.

FIG. 6. Integrations based on 5 eq of PNA olefin at t=0. DMF residual proton is then integrated accordingly for the ensuing time points.

Figure 7:
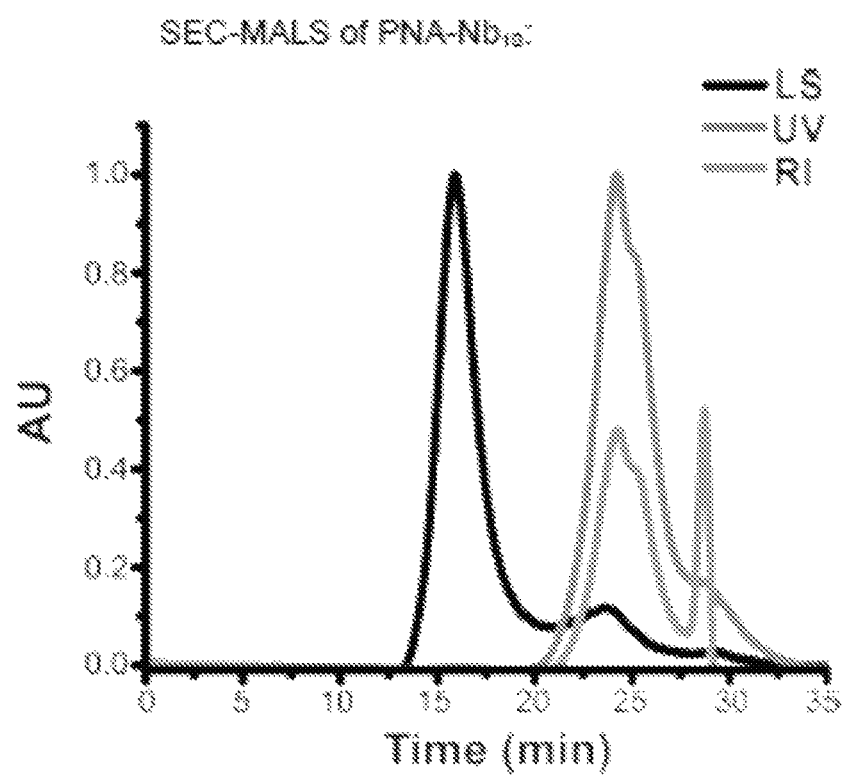
FIG. 7. SEC-MALS for I.

FIG. 7. SEC-MALS for I. The M$_n$ was determined to be 13,790 with a PDI of 1.388, giving a degree of polymerization of 5 by LS, as opposed to 10 by $^1$H NMR. This discrepancy can be attributed to error in the assignment of the dn/dc. The dn/dc used to calculate the M$_n$ was 0.179, the known dn/dc for polystyrene in DMF. In addition, a large LS peak can be seen at 16 minutes. This peak corresponded to a M$_n$ of 7.3×10$^6$ and indicated polymer aggregation in DMF. SEC-MALS for III could not be obtained due to polymer insolubility in DMF.

6. Block Copolymer Synthesis via Ring-Opening Metathesis Polymerization (ROMP)

Figure 8:
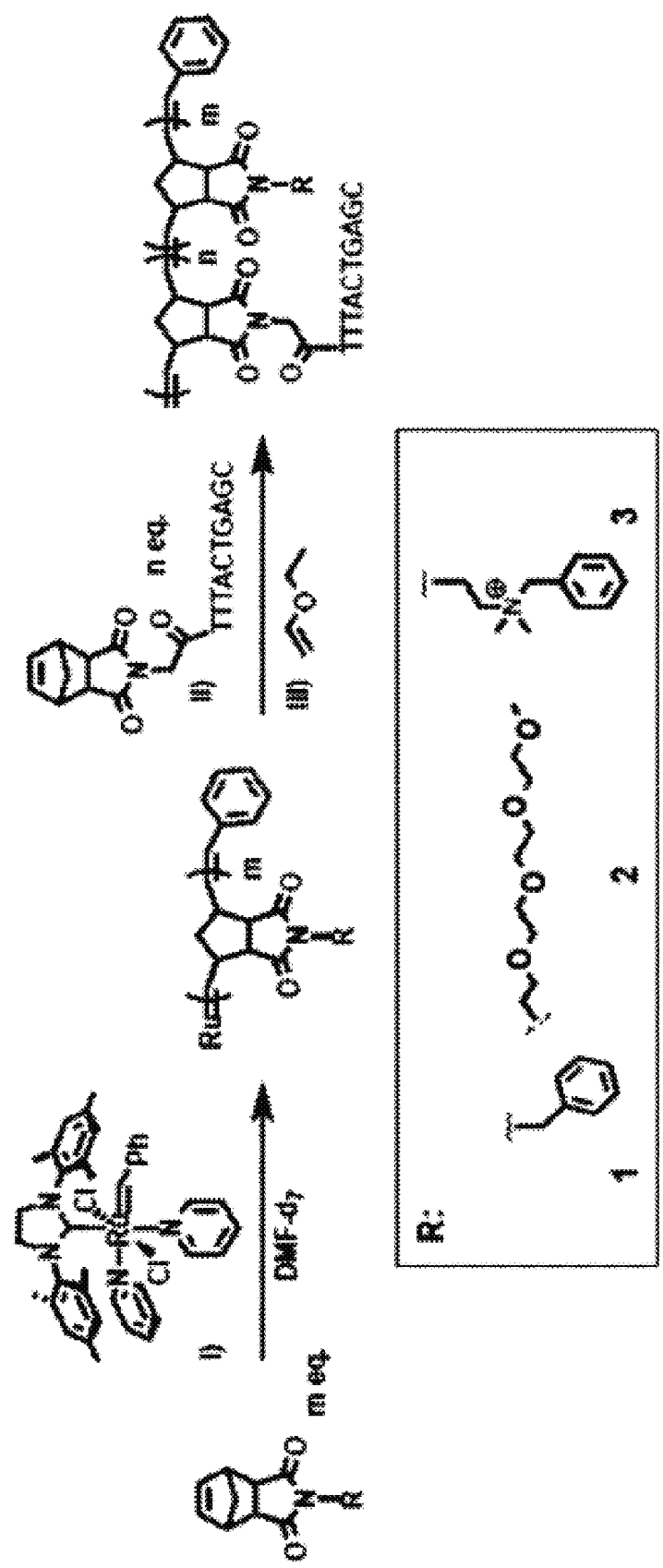
FIG. 8. Synthesis of PNA block copolymers using Grubb's 2nd generation modified catalyst in ROMP.

FIG. 8. General scheme of ROMP synthesis of block copolyPNA using Grubb's 2$^{nd}$ generation modified catalyst. A small aliquot of block 1 was terminated using III (ethyl vinyl ether) for SEC-MALS analysis before adding PNA. This provided an accurate M$_n$ and degree of polymerization for the first block. After polymerization of the PNA block, the complete block copolymer was again analyzed using SEC-MALS.

7. Timescale $^1$H NMR of ROMP of PNA Block Copolymers

Figure 9:
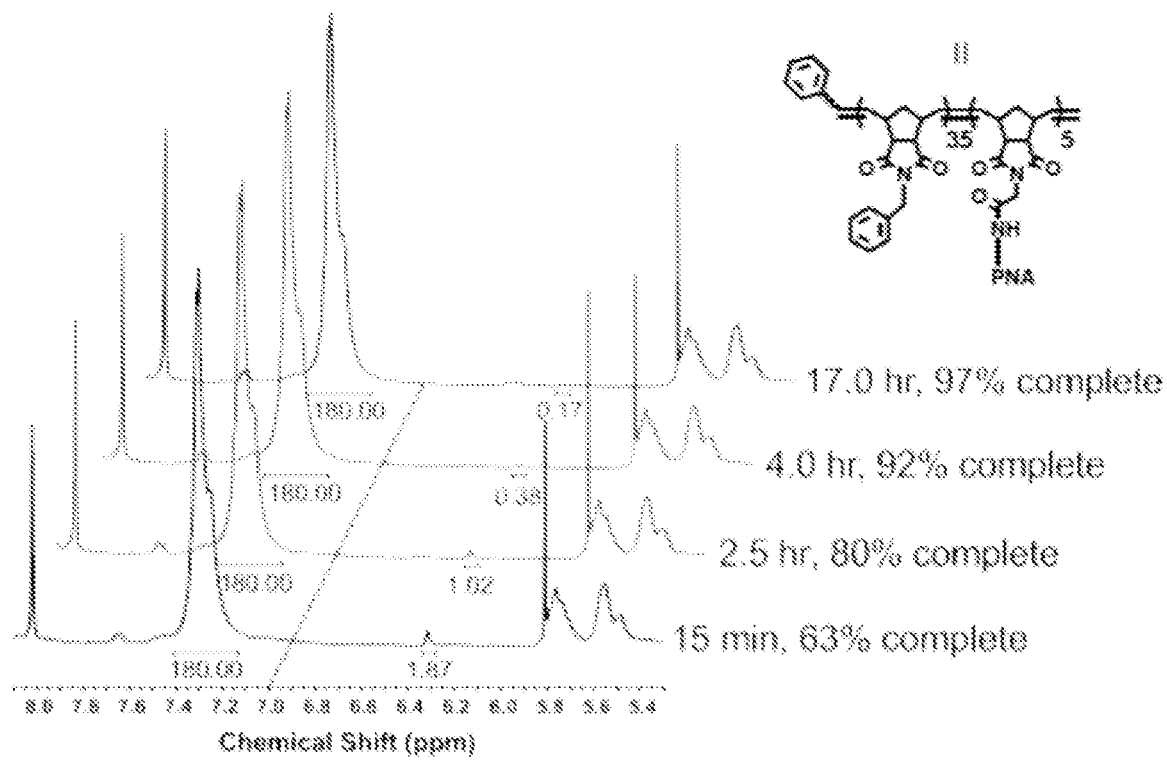
FIG. 9. ¾ NMR timescale for ROMP of II.

FIG. 9. $^1$H NMR timescale for 11. To a live catalyst on the end of a polyphenyl was added PNA (5 eq w.r.t. catalyst). The timescale shown is after 17 hours of reaction, at which point the polymer was terminated. The integrals shown are based on the amount of added phenyl-functionalized norbornene (35 eq. w.r.t catalyst, 5 protons/phenyl plus 5 protons of phenyl alkylidene for a total of 180 protons) and the amount of added PNA-Nb (5 eq w.r.t. catalyst).

Synthetic Procedure Details for ROMP of II

N-phenyl-cis-5-norbornene-exo-dicarboximide[1](1) in a J-Young NMR tube (5 mg, 0.02 mmol) was dissolved in 250 pL anhydrous and degassed DMF-d$_7$ in a glove box. Catalyst (IMesH$_2$)(C$_5$H$_5$N)$_2$(Cl)$_2$Ru=CHPh (0.4 11 mg, 0.56μηol) was added and the tube was removed from the glove box and ¾ NMR spectra were recorded until compete consumption of olefin. After olefin consumption, the tube was returned to the glove box and PNA-Nb (8.2 mg, 2.8μηol, 5 equivalents w.r.t. catalyst) was added in 100 μL anhydrous and degassed DMF-d$_7$. The tube was removed from the glove box and $^1$H NMR spectra were recorded at the indicated time points. Upon consumption of the olefin, the tube was returned to the glove box and termination agent ethyl vinyl ether (100 μL, excess) was added to the reaction mixture, and the mixture was allowed to sit at room temperature for 20 minutes. The crude polymer was precipitated from cold methanol and analyzed by SEC-MALS.

Figure 10:
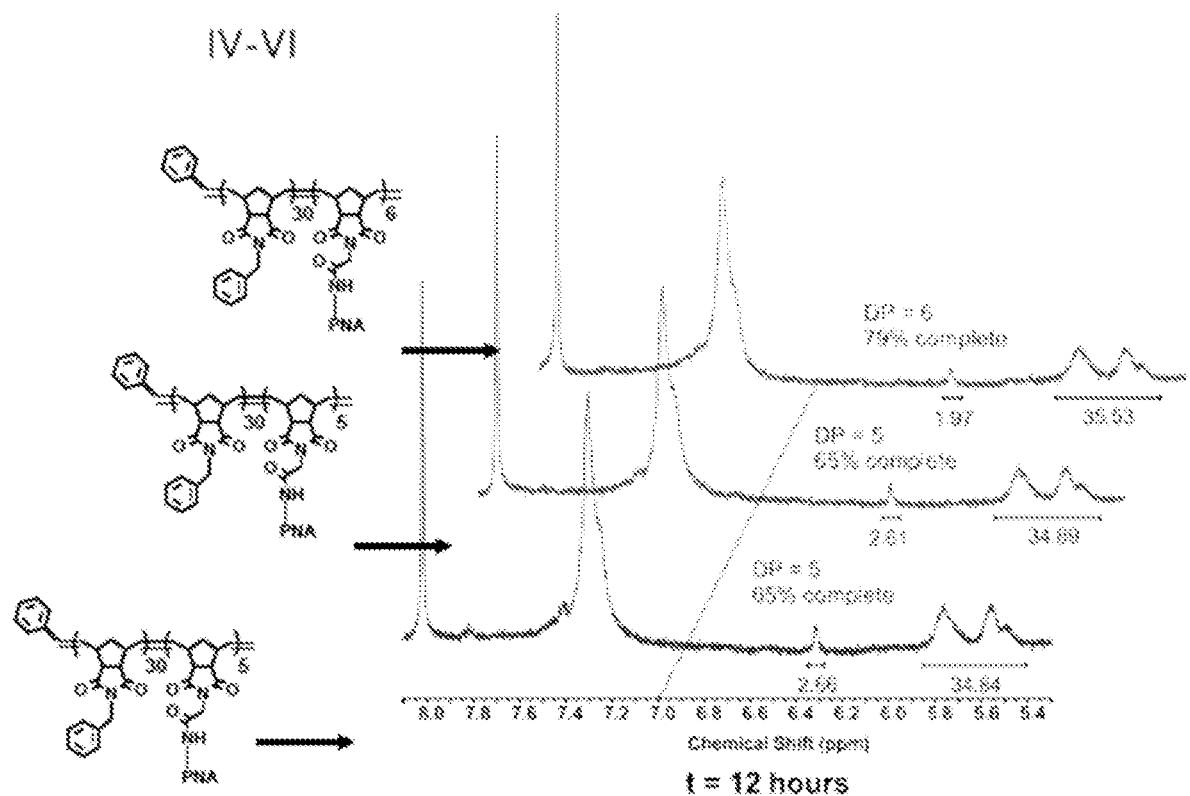
FIG. 10. ¾ NMR timescale for ROMP of 3 identical block copolymer ratios IV-VI.

FIG. 10. $^1$H NMR timescale for ROMP of 3 identical block copolymers IV-VI. One lot of polyphenyl was distributed evenly for the synthesis of the 3 block copolymers. The amount of PNA-Nb added was identical (7.5 eq w.r.t. catalyst). The timepoint shown is after 12 hours of reaction, at which point all three polymers were terminated. The integrals shown are based on the SLS value determined for the polyphenyl block ($M_n$ was 7,546 g/mol, giving a degree of polymerization of 30) and the amount of added PNA-Nb. Based on this value, the total degree of polymerization should be 37.5.

Synthetic procedure details for ROMP of IV-VI

N-phenyl-cis-5-norbornene-exo-dicarboximide $^1$(1) was polymerized by dissolving 13.57 mg (0.05 mmol) in 200 μL DMF-$d_7$ and mixing with 1.3 mg (0.0017 mmol) of catalyst dissolved in 50 μL DMF. After complete polymerization (10 min), 6.4 μl of this reaction (0.044μηιol w.r.t. catalyst) was taken on and added to 1 mg (0.34μηιol) of PNA norbornyl monomer (this reaction described below). The remaining phenyl homopolymerization reaction mixture was quenched with excess ethyl vinyl ether, precipitated and analyzed by SEC-MALS (DP=30).

For incorporation of PNA norbonyl monomer as the second block in a phenyl-PNA block copolymer, 3.5 mg (1.2μηιol) PNA monomer was dissolved with heating in 15 μL DMSO-$d_6$ and diluted to 65 μL with 50 μL of DMF-$d_7$ to yield a stock solution of PNA monomer at a concentration of 18.5 mM. 18.6 μL of this PNA stock solution (1 mg, 0.34 giol) was added to 6.4 μl of phenyl homopolymer solution with live ruthenium catalyst (as described above) for a total reaction volume of 25 μL. This exact protocol was followed for 3 identical 25 L reactions. Each of the three reactions was heated in a glass HPLC insert at 40° C. on a heat block with sand used to facilitate efficient heat transfer between the heating block and the glass HPLC vial insert. After 1 hour of heating, all three reactions were removed from heat and subsequently diluted to 80 μL total volume with DMF-$d_7$ and added to a 3 mm O.D. NMR tube via a heat-pulled glass pipette in order to provide enough volume for NMR analysis while keeping the concentration at a maximum. After 12 hours, an NMR spectrum was acquired for each of the three samples. Following this, the tube was returned to the glove box and termination agent ethyl vinyl ether (100 μL, excess) was added to the reaction mixture, and the mixture was allowed to sit at room temperature for 20 minutes. The crude polymer was precipitated from cold methanol and analyzed by SEC-MALS.

Figure 11:
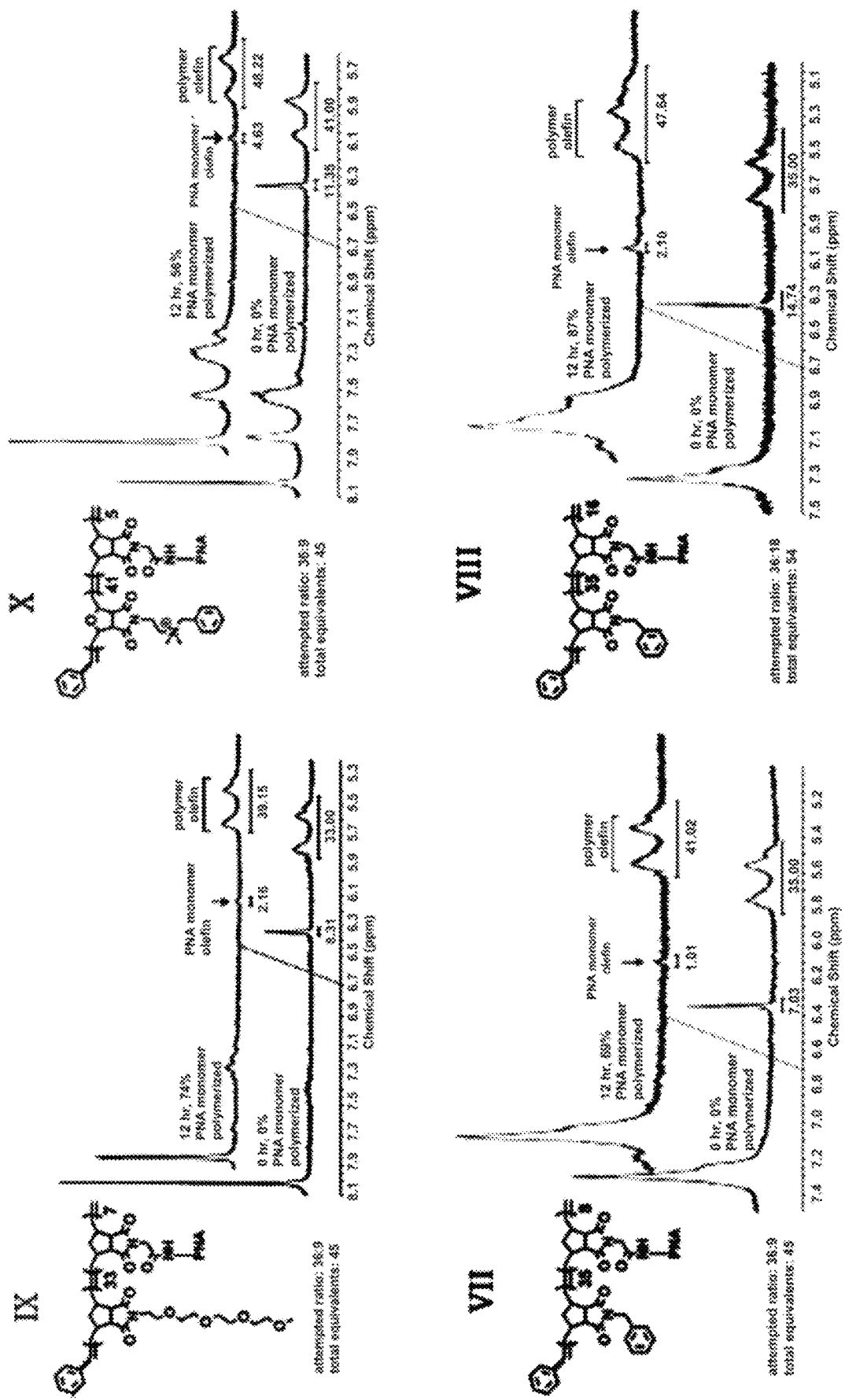
FIG. 11. ¾ NMR timescale for ROMP of VII-X.

FIG. 11. $^1$H NMR timescale for VI I-X.

The timescale shown is after 12 hours of reaction, at which point all polymers were terminated. The integrals shown are based on the SLS value determined for the first block ($M_n$ was 11,900 g/mol, giving a degree of polymerization of 33 for peg, $M_n$ was 13,430 g/mol, giving a degree of polymerization of 41 for NR4, and the $M_n$ was 8,827 g/mol, giving a degree of polymerization of 35 for ph) and the amount of added PNA-Nb. Based on this value, the total degree of polymerization should be 45 for each block copolymer.

ROMP Conditions for VII-X

N-phenyl-cis-5-norbornene-exo-dicarboximide (1) (3.47 mg, 13.7μηιole), 2-(2,5,8,11-tetraoxatridecan-13-yl)-3a,4,7,7a-tetrahydro-1H-4,7-methanoisoindole-1,3(2 H)-dione (2) (4.8 mg, 13.7μηιol), and N-benzyl-2-(1,3-dioxo-1,3,3a, 4,7,7a-hexahydro-2 H-4,7-epoxyisoindol-2-yl)-N,N -dimethyl-ethan-1-aminium (3) (4.47 mg, 13.7μηιol) in 85.5 μL DMF-$d_7$ were polymerized by mixing with 0.274 mg (0.38μηιol) of catalyst (14.5 μL of a 0.026 M soln. in DMF-$d_7$) for a total volume of 100 μL DMF-$d_7$. After complete polymerization, 10 μl of this reaction (0.038μηιol w.r.t. catalyst) was taken out and added to 1 mg (0.34μηιol) of PNA norbornyl monomer (this reaction described below). The remaining polymerized first block reaction mixture was quenched with excess ethyl vinyl ether, precipitated and analyzed by SEC-MALS.

For incorporation of PNA norbonyl monomer as the second block in a phenyl-PNA block copolymer, 4.2 mg (1.4μηιol) PNA monomer was dissolved with heating in 25 μL DMSO-d6 to yield a stock solution of PNA monomer at a concentration of 57.5 mM. 5.95 μL of this PNA stock solution (1 mg, 0.34μηιol) was added to 10 μl of phenyl homopolymer solution with live ruthenium catalyst (as described above) for a total reaction volume of 15.95 μL. After 12 hours at r.t., all four reactions were diluted to 90 uL total volume with DMF-$d_7$ and added to a 3 mm O.D. NMR tube via a heat-pulled glass pipette in order to provide enough volume for NMR analysis while keeping the concentration at a maximum.

Figure 12A:
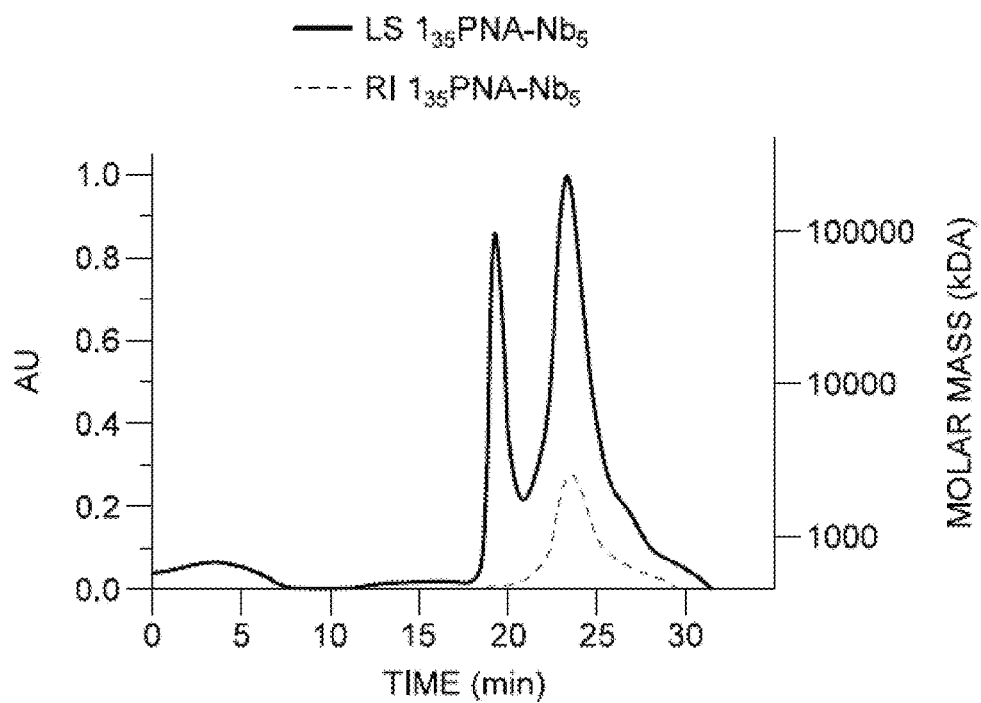
FIGS. 12A-12B. (12A) SEC-MALS of II and (12B) Chemical shift.
Figure 12B:
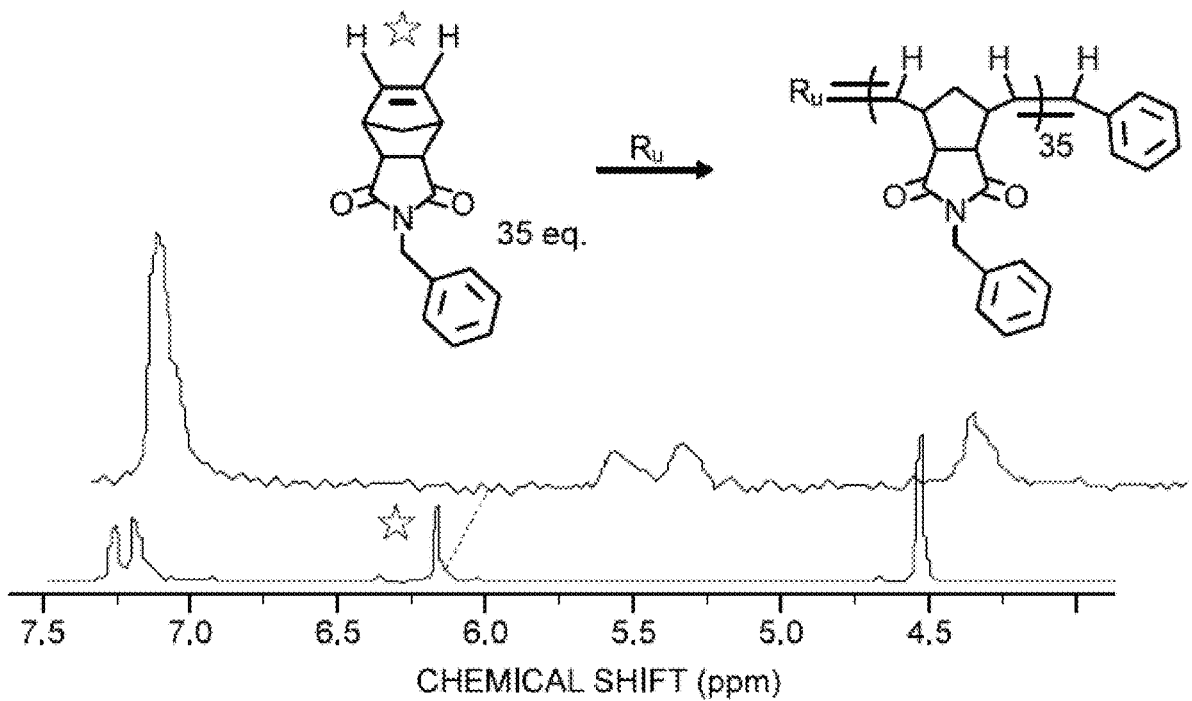

FIGS. 12A-12B. FIG. 12A) SEC-MALS of II. SEC-MALS of the polyphenyl block was not observed due to an insufficient aliquot removal of the polyphenyl block. However, complete consumption of the phenyl-norbornene backbone was observed by $^1$H NMR. After complete polymerization of the block copolymer, the $M_n$ of the total polymer (28,270) and the PDI (1.035) were determined by SEC-MALS. $M_n$ gives a degree of polymerization of 6 for PNA (mass fraction of this RI peak is 97.9%). The phenyl-norbornene monomer (1) was added in 35 equivalents w.r.t. to PNA. A large LS peak, but small RI (corresponding to a mass fraction of 2.1%) peak can be seen at 20 minutes. This peak corresponded to a $M_n$ of 3.3×10$^5$ and indicated block copolymer aggregation in DMF. FIG. 12B)$^1$H NMR for the polymerization of the phenyl-norbornene block of PI1$_{35}$PNA$_5$. The red star indicates the olefin peak at 6.32 ppm that is observed to disappear upon polymerization. The peak corresponds to the 2 protons also indicated by a star in the chemical structure.

Figure 13A:
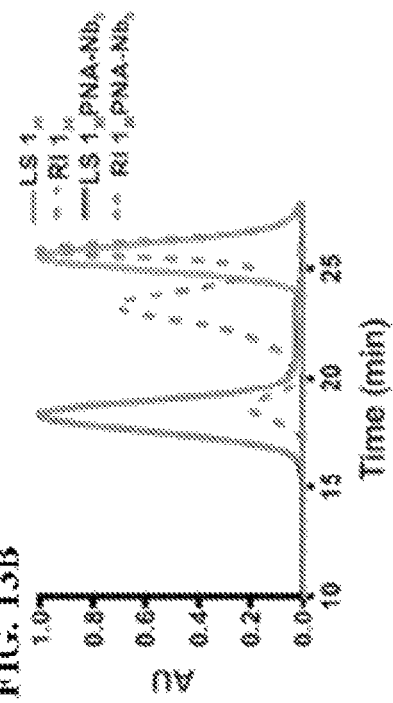
FIGS. 13A-13D. SEC-MALS of IV-VI (FIGS. 13A-13D).
Figure 13B:
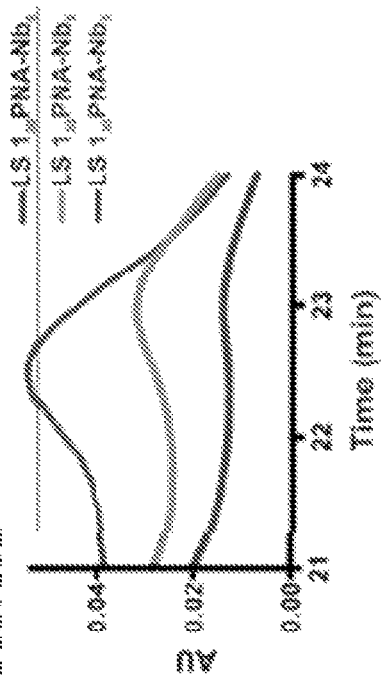

FIGS. 13A-13D. SEC-MALS of polyphenyl block of as well as SEC-MALS of 3 identical block copolymers of PNA (TV-VI). After complete polymerization of phenyl-norbornene monomer (1), a predetermined volume was removed from the solution and terminated with ethyl vinyl ether to obtain the $M_n$ of the polyphenyl block, which was determined to be 7,546, giving a degree of polymerization of 30 for the phenyl block, with a PDI of 1.03. After termination of the complete block copolymer, the $M_n$ was determined for all 3 identical polymers and for all peaks that could be analyzed. FIG. 13A) $M_n$ was 7.7×10$^6$, PDI 2.06, and mass fraction was 26% for peak between 15.4-20.5 min by RI. $M_n$ was 14,810, PDI 1.54, and mass fraction was 48% for peak between 20.6-24.8 min by RI. This peak was used to determine degree of polymerization for the PNA, as it most likely corresponds to the disaggregated block copolymer. $M_n$ was 1,860, PDI 1.41, and mass fraction was 26% for peak between 25-26.5 min by R$^1$, corresponding to unpolymerized PNA-Nb (2922 g/mol). FIG. 13B) $M_n$ was 1.5×

Figure 13C:
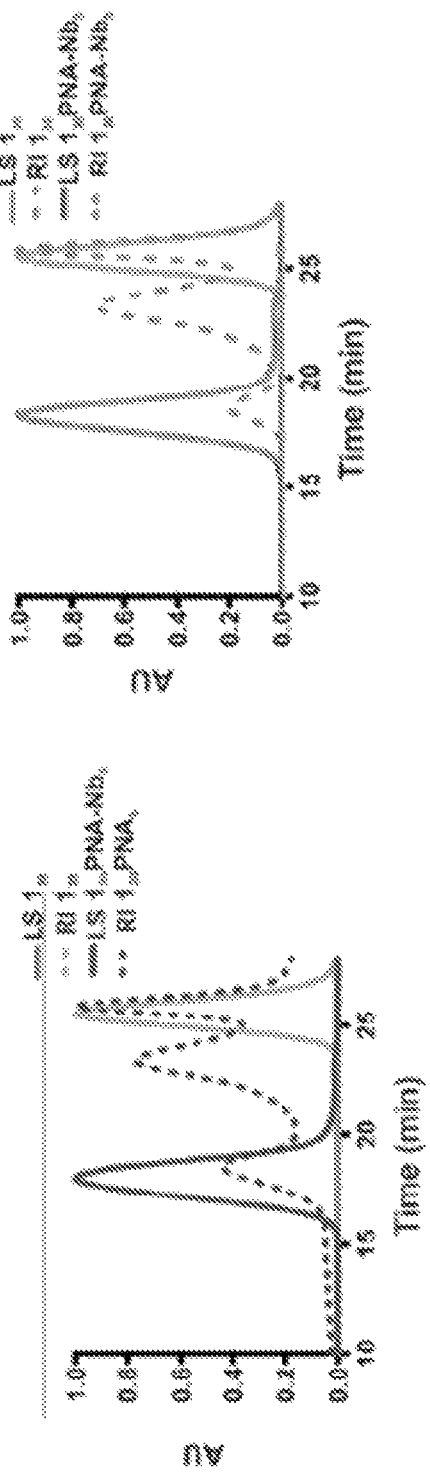
Figure 13D:
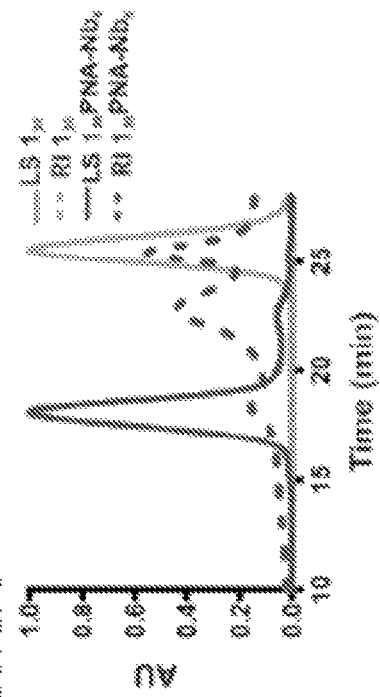

$10^6$, PDI 1.45, and mass fraction was 10% for peak between 16-20.6 min by RI. $M_n$ was 18,700, PDI 1.34, and mass fraction was 54% for peak between 20.9-24.9 min by RI. This peak was used to determine degree of polymerization for the PNA, as it most likely corresponds to the disaggregated block copolymer. $M_n$ was 3,850, PDI 1.11, and mass fraction was 36% for peak between 25.1-27.3 min by RI, corresponding to unpolymerized PNA-Nb (2922 g/mol). FIG. 13C) $M_n$ was $1.6 \times 10^5$, PDI 2.36, and mass fraction was 16% for peak between 16.9-19.5 min by RI. $M_n$ was 11,210, PDI 1.25, and mass fraction was 52% for peak between 19.9-24.2 min by RI. This peak was used to determine degree of polymerization for the PNA, as it most likely corresponds to the disaggregated block copolymer. $M_n$ was 1,661, PDI 1.23, and mass fraction was 32% for peak between 25-26.5 min by $R^1$, corresponding to unpolymerized PNA-Nb (2922 g/mol). FIG. 13D) Expanded view of LS peaks for all 3 block copolymers.

Figure 14A:
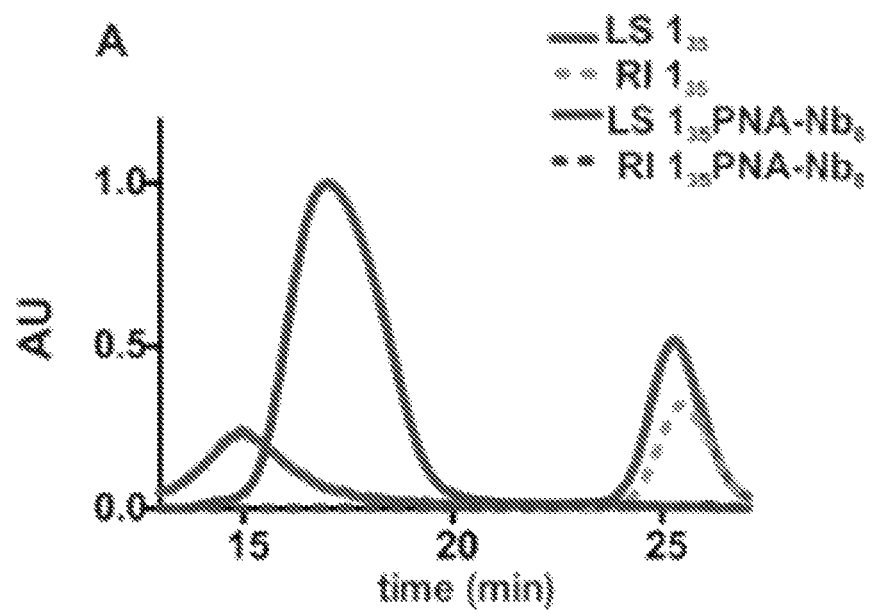
FIGS. 14A-14B. SEC-MALS of (FIG. 14A) homophenyl block as well as (FIG. 14B) SEC-MALS of VII.
Figure 14B:
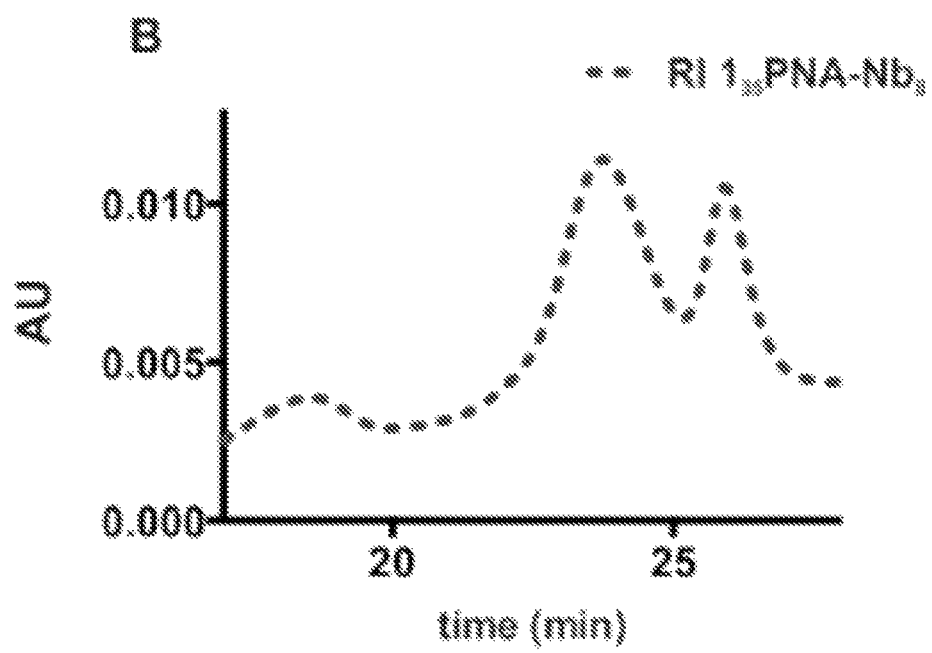

FIGS. 14A-14B SEC-MALS of polyphenyl block as well as SEC-MALS of VII. FIG. 14A) After complete polymerization of phenyl norbornene monomer (1), a predetermined volume was removed from the solution and terminated with ethyl vinyl ether to obtain the $M_n$, which was determined to be 8,827, giving a degree of polymerization of 35, with a PDI of 1.02. After termination of the complete block copolymer, the $M_n$ was determined for all peaks that could be analyzed. $M_n$ was $6.2 \times 10^5$, PDI 2.66, and mass fraction was 25% for peak between 14.6-20.2 by RI. $M_n$ was 16,840, PDI 1.33, and mass fraction was 51% for peak between 20.7-25.1 min by RI. This peak was used to determine degree of polymerization for the PNA, as it most likely corresponds to the disaggregated block copolymer. The $M_n$ for peak between 25.6-27.3 min by RI could not be determined due to inadequate LS. The mass fraction for this peak was 24%. FIG. 14B) Expanded view of RI peak showing 3 populations.

Figure 15A:
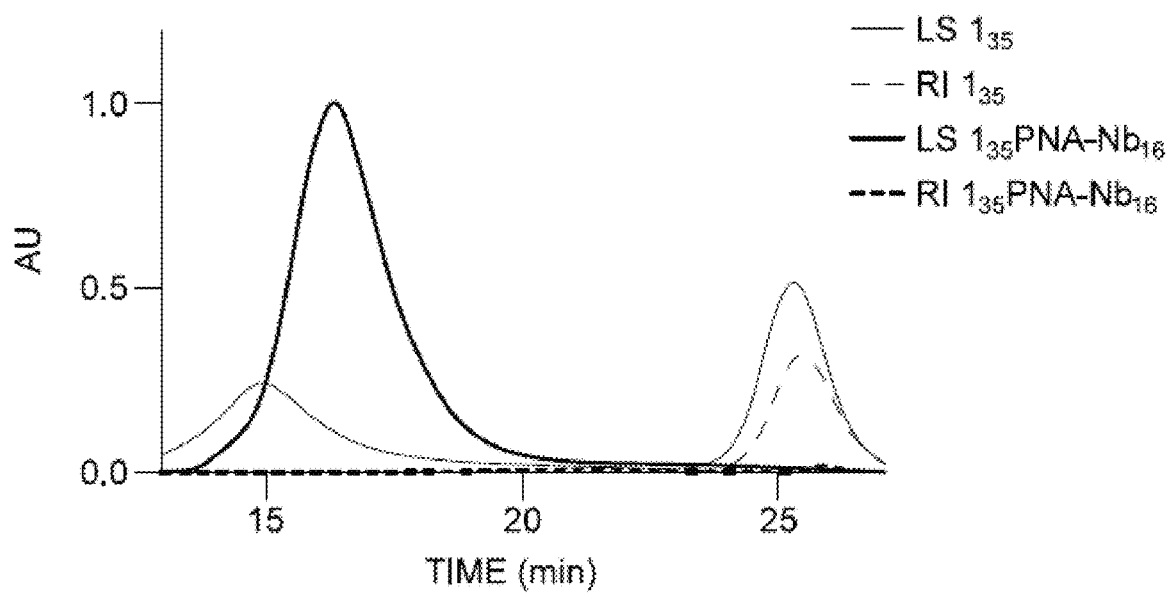
Figure 15B:
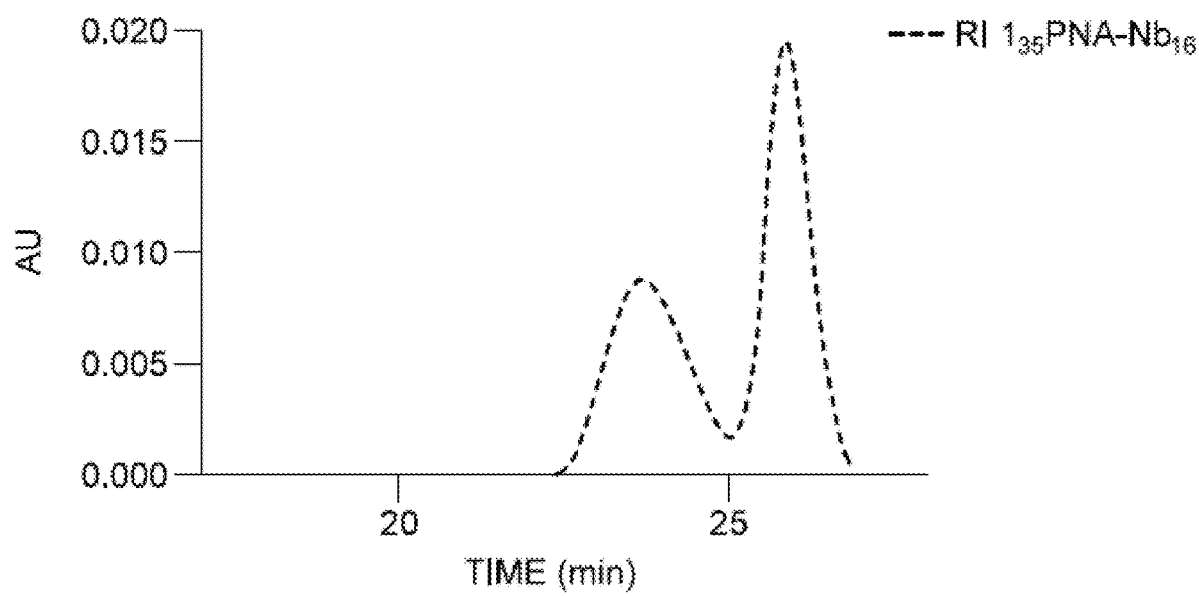

FIGS. 15A-15B SEC-MALS of polyphenyl block as well as SEC-MALS of VIII. FIG. 15A) After complete polymerization of phenyl norbornene monomer (1), a predetermined volume was removed from the solution and terminated with ethyl vinyl ether to obtain the $M_n$, which was determined to be 8,827, giving a degree of polymerization of 35, with a PDI of 1.02. After termination of the complete block copolymer, the $M_n$ was determined for all peaks that could be analyzed. $M_n$ could not be determined for the LS peak between 13.9-19.3 min due to a lack of RI. $M_n$ for the peak between 22-25 min by RI could not be determined due to inadequate LS. This peak had a mass fraction of 45%. The $M_n$ for peak between 25.2-27.3 min by $R^1$ could not be determined due to inadequate LS. The mass fraction for this peak was 55%. FIG. 15B) Expanded view of RI peak showing 2 populations.

Figure 16A:
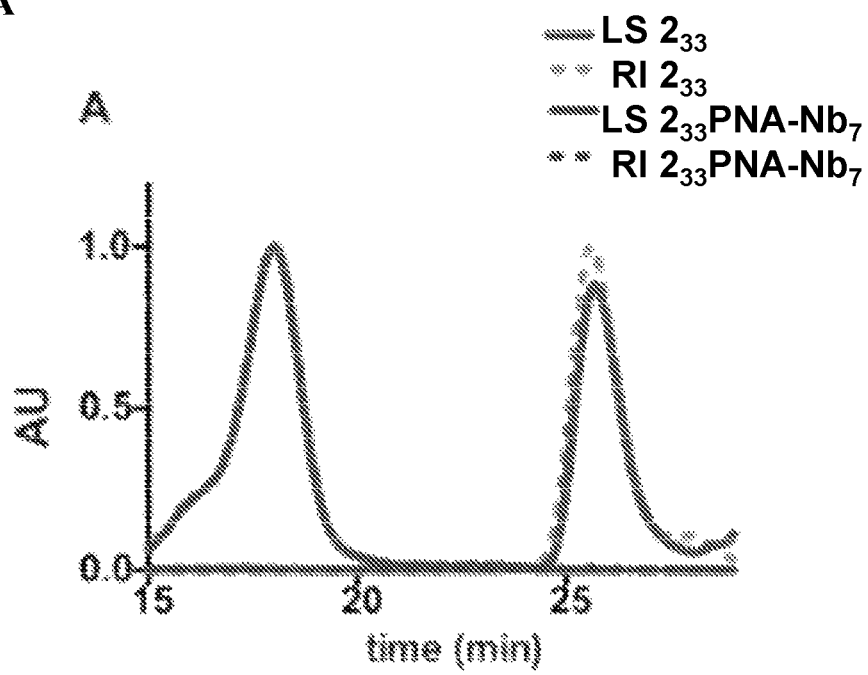
FIGS. 16A-16B. SEC-MALS of (FIG. 16A) homopeg block as well as (FIG. 16B) SEC-MALS of IX.
Figure 16B:
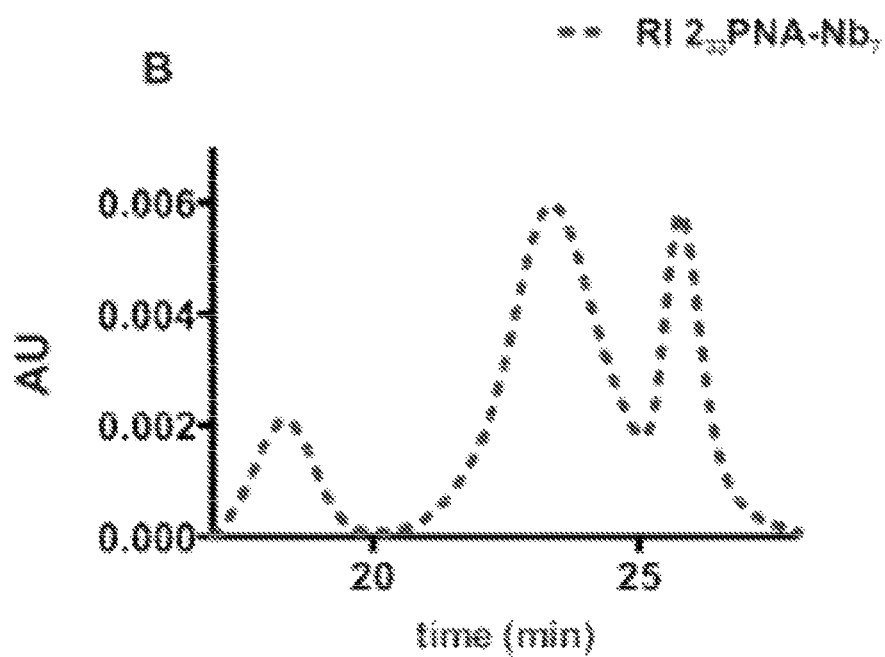

FIGS. 16A-16B SEC-MALS of first block as well as SEC-MALS of IX. FIG. 16A) After complete polymerization of peg-norbornene monomer (2), a predetermined volume was removed from the solution and terminated with ethyl vinyl ether to obtain the $M_n$ of the polypeg block, which was determined to be 11,900, giving a degree of polymerization of 33 for the peg block, with a PDI of 1.03. After termination of the complete block copolymer, the $M_n$ was determined for all peaks that could be analyzed. $M_n$ was $2.5 \times 10^6$, PDI 1.29, and mass fraction was 12% for peak between 15-20 by RI. Despite showing multiple peaks by RI, the $M_n$ could not be determined for any other peaks due to lack of an LS peak. The mass fraction for RI peak between 20.5-25 min was 61%, and 27% for the peak between 25.15-27.7 min. FIG. 16B) Expanded view of $R^1$ peaks showing 3 populations.

Figure 17A:
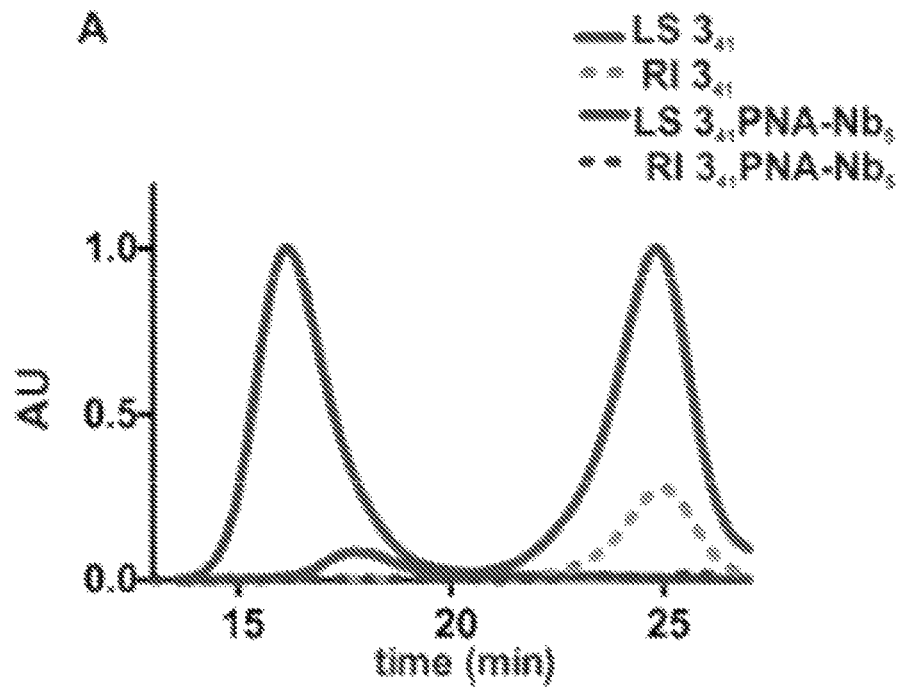
FIGS. 17A-17B. SEC-MALS of (FIG. 17A) homo quaternary amine block as well as (FIG. 17B) SEC-MALS of X.
Figure 17B:
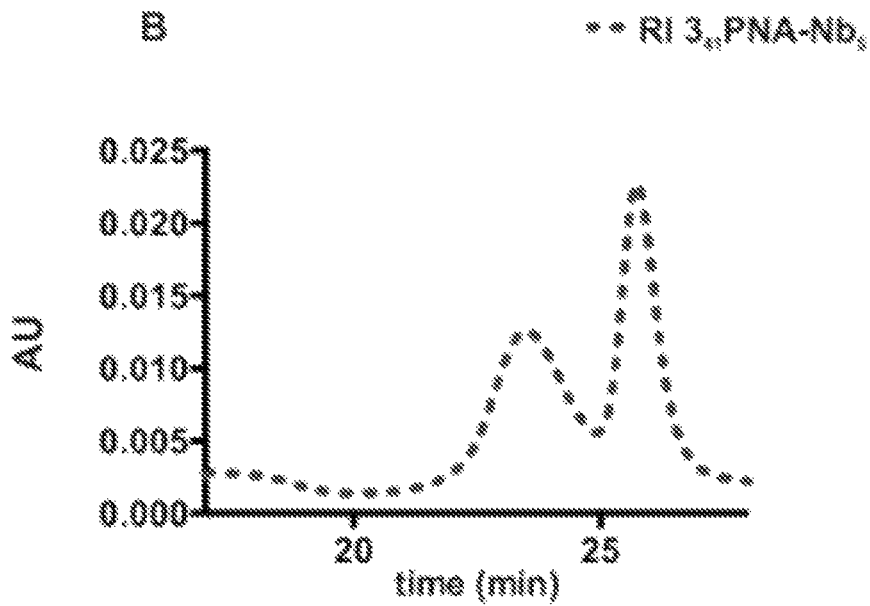

FIGS. 17A-17B SEC-MALS of quaternary amine block as well as SEC-MALS of X. FIG. 17A) After complete polymerization of quaternary amine-norbornene monomer (3), a predetermined volume was removed from the solution and terminated with ethyl vinyl ether to obtain the $M_n$, which was determined to be 13,430, giving a degree of polymerization of 41, with a PDI of 1.1. After termination of the complete block copolymer, the $M_n$ was determined for all peaks that could be analyzed. $M_n$ was $4.6 \times 10^6$, PDI 1.05, and mass fraction was 18% for peak between 13.9-19.8 by RI. Despite showing multiple peaks by RI, the $M_n$ could not be determined for any other peaks due to lack of an LS peak. The mass fraction for RI peak between 20.6-24.8 min was 43%, and 39% for the peak between 25-27.1 min. FIG. 17B) Expanded view of RI peaks showing 3 populations.

8. PNA-Polymer Micelle Formation

Synthesis 6 mg of 11 was dissolved into DMSO at a concentration of 2 mg/ml. This solution was transferred to 3,500 MWCO snakeskin dialysis tubing (Thermo Scientific) and 3 ml $H_2O$ was added. The resulting solution was dialyzed against 1.0 L of Nanopure $H_2O$ for 3 days, with the $H_2O$ being changed daily. UV confirmed the concentration of the final solution and a speedvac was used to concentrate solutions to ~0.1 mg/ml. Nucleic acid concentrations were determined by UV absorbance at 260 nm using a Thermo Scientific NanoDrop 2000c spectrophotometer. An extinction coefficient of 99,200 $L/mol^{-1} cm^{-1}$ was used. This coefficient was calculated as the extinction coefficient of the entire sequence.

9. TEM

Copper grids (formvar/carbon-coated, 400 mesh copper, Ted Pella #01754) were prepared by glow discharging the surface at 20 mA for 1.5 minutes followed by treatment with 3.5 µL 250 mM $MgCl_2$ in order to prepare the surface for PNA nanoparticle adhesion. The $MgCl_2$ solution was wicked away with filter paper and 3.5 µL of PNA nanoparticle (ca 100 µM PNA) solution was deposited on the grid surface. This solution was allowed to sit for 5 minutes before being washed away with 4 drops of glass distilled $H_2O$ and subsequent staining with 3 drops of 1% w/w uranyl acetate. The stain was allowed to sit for 30 seconds before wicking away with filter paper. All grid treatments and sample depositions were on the dark/shiny/glossy formvar-coated face of the grid (this side face up during glow discharge). Samples were then imaged via TEM.

Figure 18A:
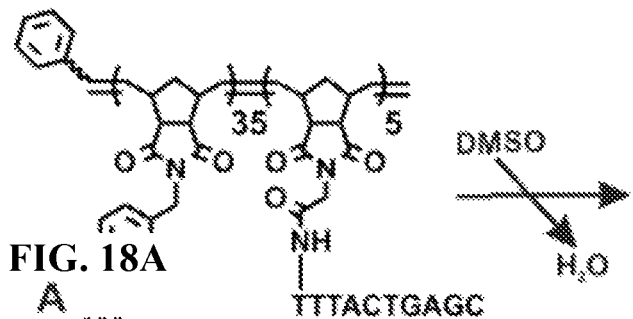
FIGS. 18A-18D. DLS and TEM of PNA-NP made from II.
Figure 18B:
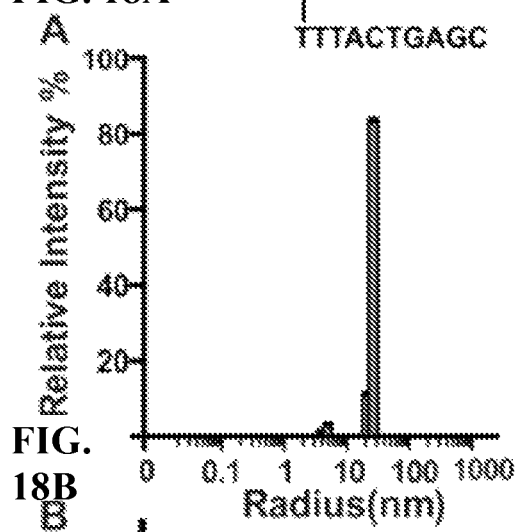
Figure 18C:
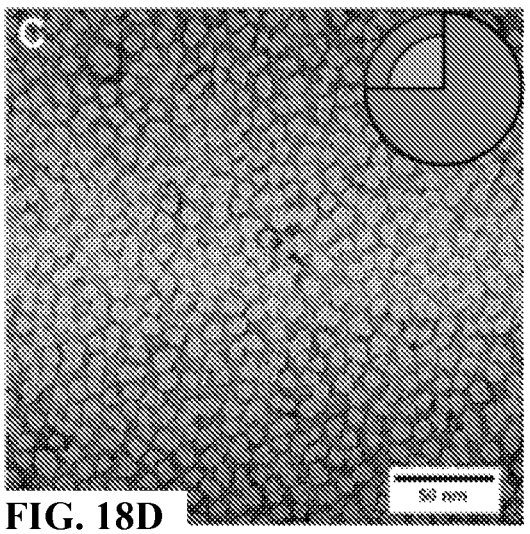
Figure 18D:
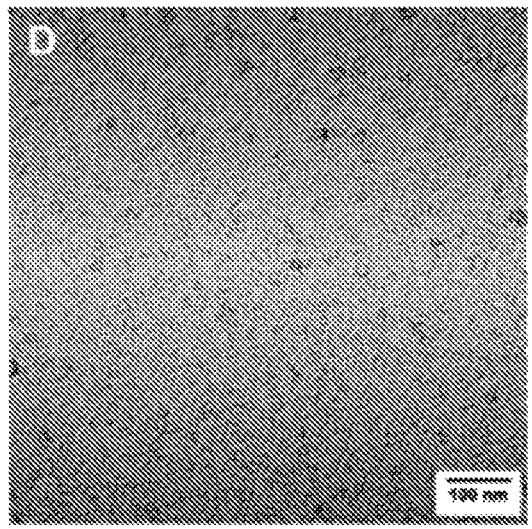

FIGS. 18A-18D. FIG. 18A) After dialysis into $H_2O$ from DMSO, II forms nanoparticles that by DLS are aggregates on the size order of 50 nm in diameter. FIG. 18B) Autocorrelation function for nanoparticles formed from copolyPNA-3. FIG. 18C) Negative-stain TEM showing nanoparticles on the order of 10-30 nm. The majority of the material, once dried, showed no particle aggregation. FIG. 18D) Negative stain TEM showing a zoomed-out section of the grid.

10. DNA Melting Temperature Analysis

Melting temperature analysis were performed by heating each sample from 20° C. (20 minute equilibration time) to 90° C. using a temperature gradient of 1° C./minute. Melting temperatures were calculated as first derivatives of the curve. Nanoparticles formed from II, renamed as PNA-NP, were at a concentration of 1 µM in water. The mixture was made by adding Dulbecclo's IX PBS to the nanoparticles followed by 100 nM-1 µM of the complementary DNA in $H_2O$. Final concentration of $NaH_2PO_4$ is 6.7 mM, NaCl is 113 mM, KCl is 22.2 mM, and $KH_2PO_4$ is 1.46 mM, all in a total volume of 50 µL. Annealing was done at room temperature for 2 hours. The sample was refrigerated at 8° C. for 15 minutes, after annealing, and subsequently analyzed.

Figure 19A:
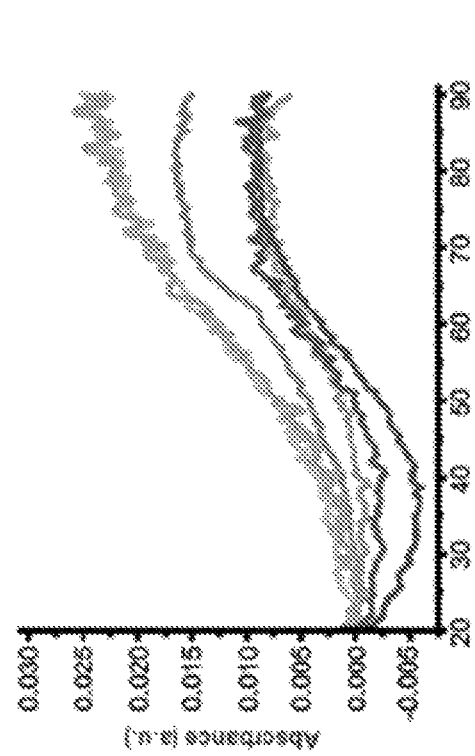
FIGS. 19A-19C. Tm data for PNA-NP and complementary DNA sequence.
Figure 19C:
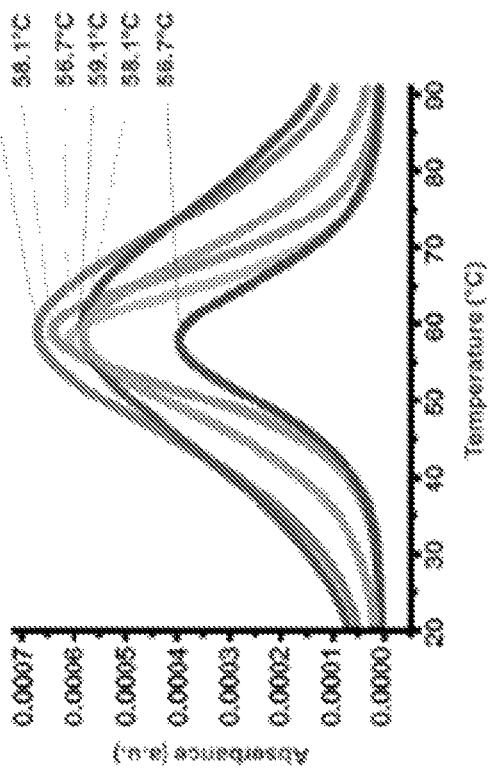
Figure 19B:
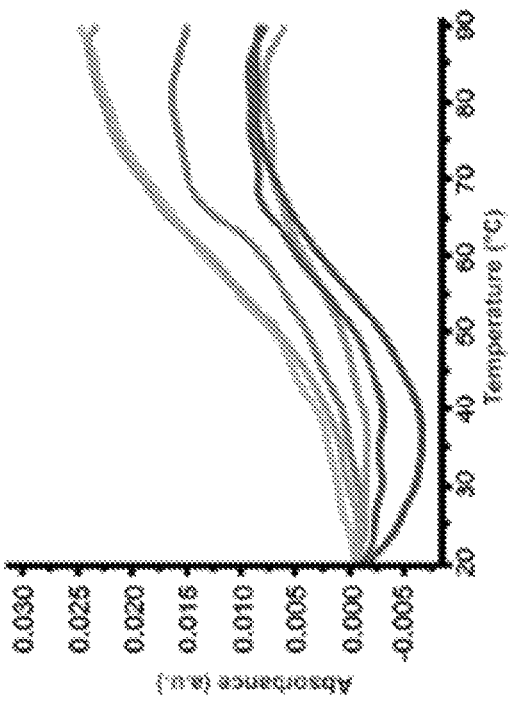

FIGS. 19A-19C. FIG. 19A) Raw $T_m$ data for PNA-PN and complementary DNA sequence. Several buffers were tested to determine ideal conditions for hybridization between PNA-NP and its DNA complement at room temperature. 1 µM PNA-NP with 100 nM complementary DNA in PBS was subsequently chosen. FIG. 19B) A 10-pt FFT filter was applied to the raw data. FIG. 19C) Derivation plots for each $T_m$ curves showing 57.8° C. average for PNA-NP and complementary DNA.

FIGS. 20A-20C. FIG. 20A) Raw $T_m$ data for PNA-NP and complementary DNA, as well as non-complementary DNA sequence. The $T_m$ for the corresponding PNA sequence (identical to PNA that was polymerized) and complementary DNA was also determined. FIG. 20B) A 10-pt FFT filter was applied to the raw data. FIG. 20C) Derivative plots for each of the $T_m$ curves showing a 7.3° C. increase for PNA-NP over its identical PNA sequence. While a derivative can be taken of the $T_m$ curve corresponding to PNA-NP and its non-complementary sequence, the curve itself is more indicative of non-specific binding, as is implied by the broad derivative, and the almost linear $T_m$.

Figure 21A:
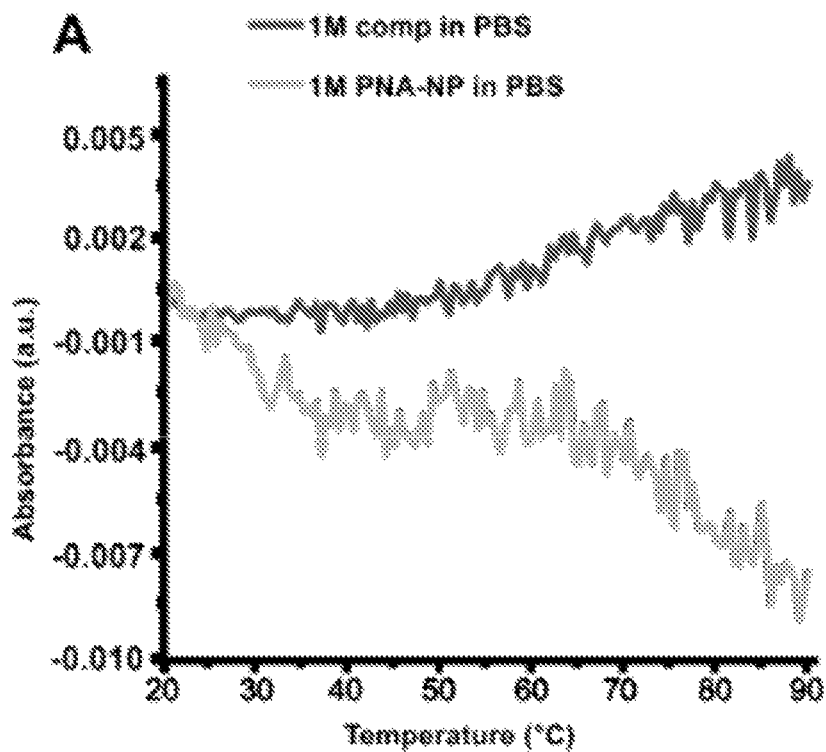
Figure 21B:
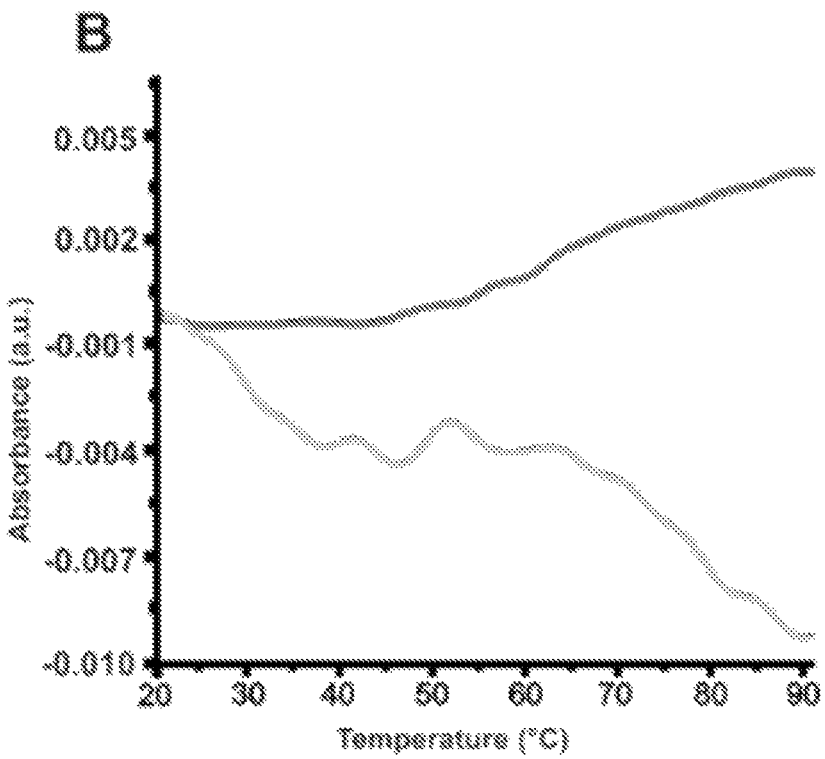
Figure 22:
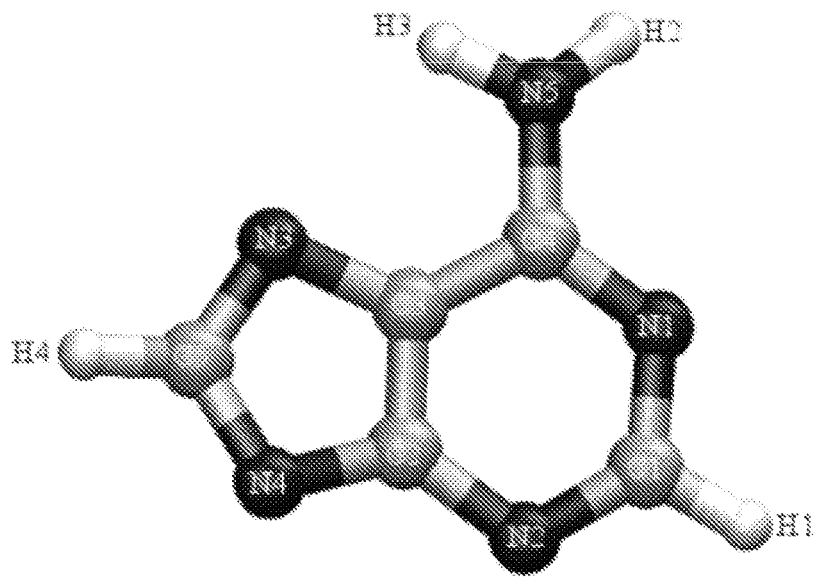
FIG. 22: Partial Charges on Adenine Base in PNA.
Figure 23:
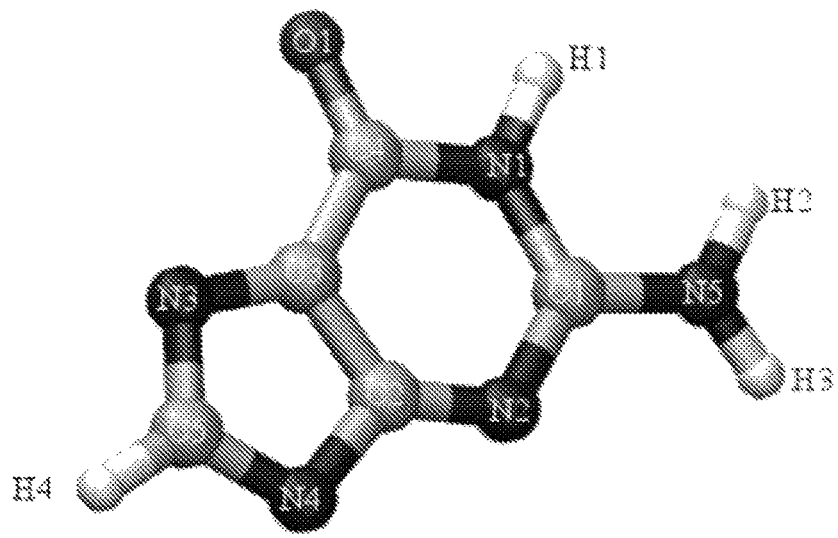
FIG. 23: Partial Charges of Guanine Base in PNA.
Figure 24:
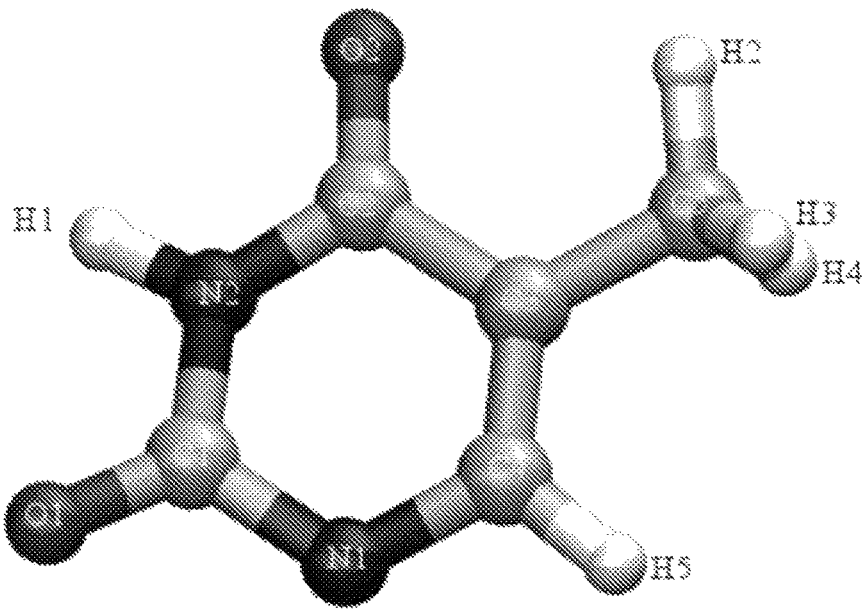
FIG. 24: Partial Charges for Thymine Base in PNA.
Figure 25:
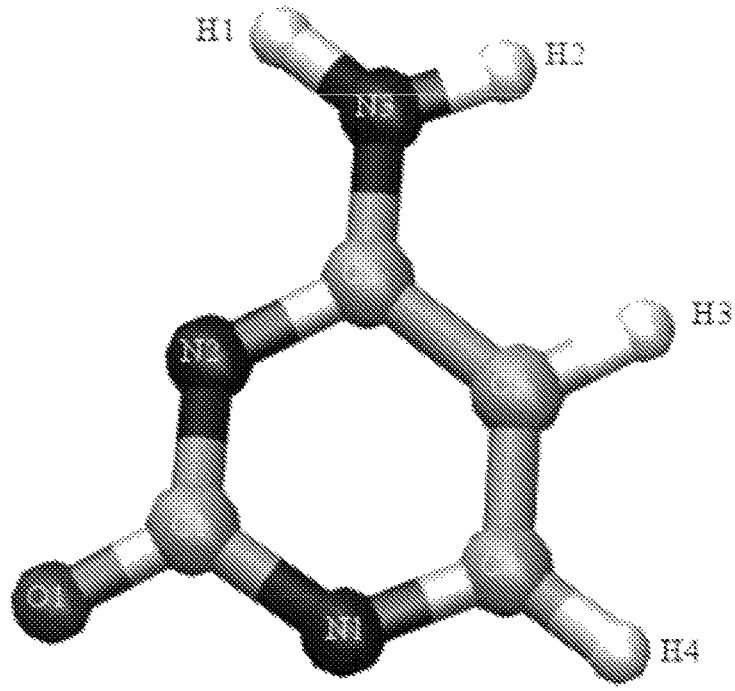
FIG. 25: Partial Charges of Cytosine Base in PNA.
Figure 26:
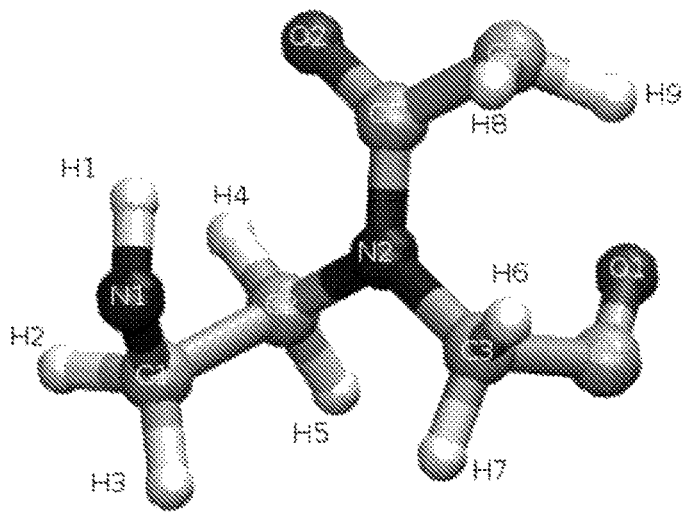
FIG. 26: Partial Charges for a Unit of the Peptide Chain in PNA.
Figure 27:
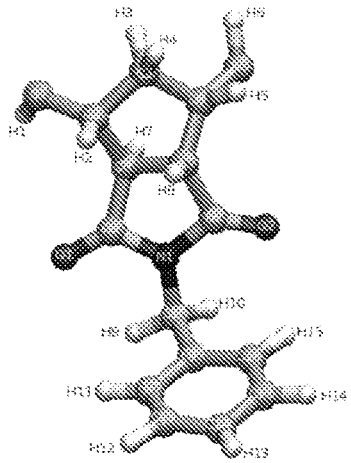
FIG. 27: Partial Charges for a Unit of the Hydrophobic Chain.
Figure 28:
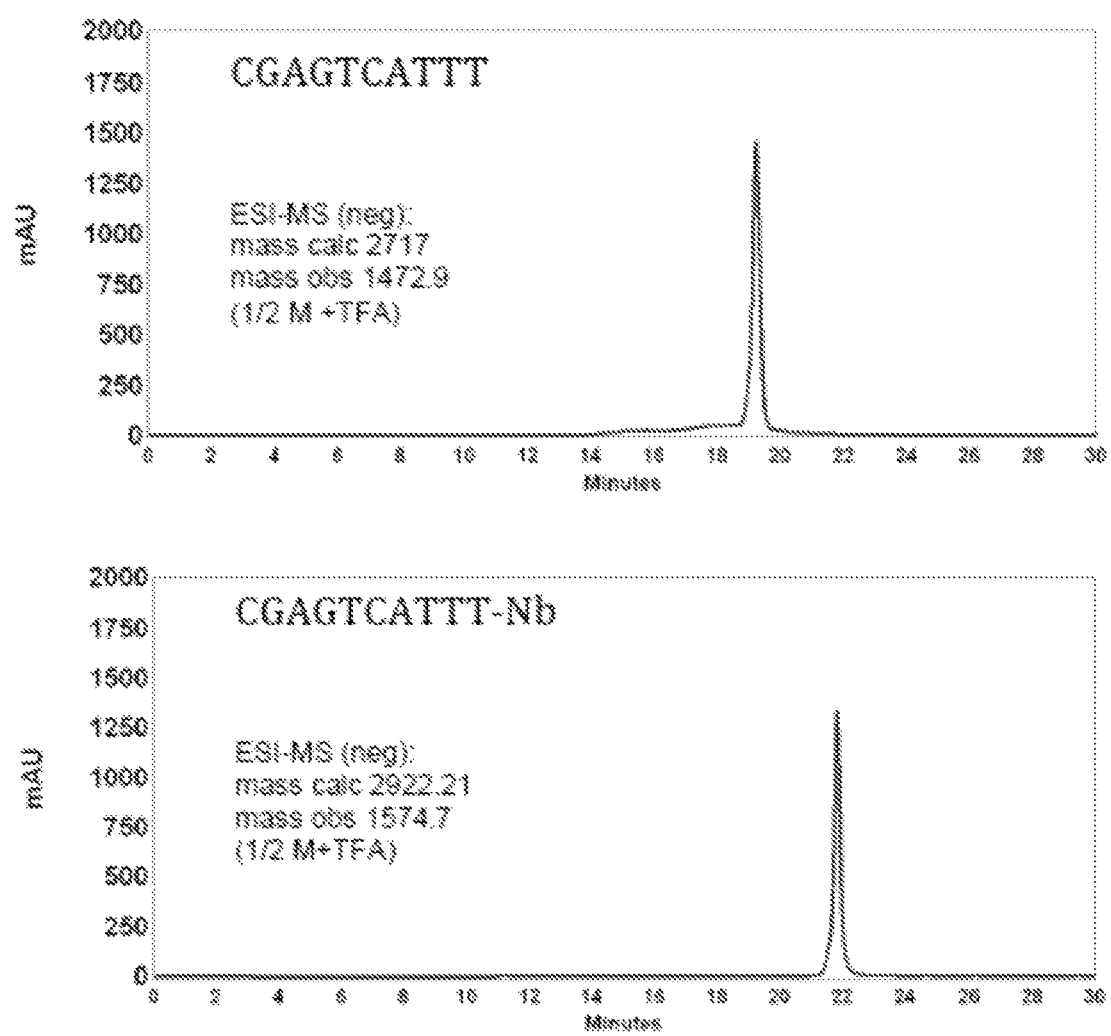
FIG. 28: HPLC Purification of PNA Sequences.

FIGS. 21A-21B. FIG. 21A) Raw $T_m$ data for PNA-NP without complementary DNA and complementary DNA without PNA in PBS showing no melting. FIG. 2IB) A 10-pt FFT filter was applied to the raw data.

11. Molecular Dynamics (MD) Simulations

A single PNA-polynorbornyl unimer was initially built in fully extended conformation with GaussView software [GaussView, Version 5, Dennington, R.; Keith, T.; Millam, J. *Semichem Inc.*, Shawnee Mission KS, 2009]. 60 identical unimers, first relaxed in vacuum for 0.3 ns at the temperature of 300 K, were spherically distributed in space, with PNA ends oriented towards the outside. The resulting PNA-NP of 60 unimers was then immersed in a cubic (TIP3P) water box with solvate plugin in VIVID [Humphrey, W.; Dalke, A.; Schulten, K. "VMD Visual Molecular Dynamics", *J. Molec. Graphics,* 1996, 14, 33-38]; water molecules present within a 65 A radius of PNA-NP center were deleted. The resulting unit cell with solvated 60-monomer PNA-NP contained 2,122,554 atoms.

MD simulations of solvated PNA-NP were performed with NAMD2 software [Phillips, J. C; Braun, R.; Wang, W.; Gumbart, J. C; Tajkhorshid, E.; Villa, E.; Chipot, C; Skeel, R. D.; Kale, L.; Schulten, K. *Journal gf Computational Chemistry,* 2005, 26, 1781-1802], where the molecules were described using the CHARMM force field. The parameters for the unimer units (PNA, norbornyl) were obtained by analogy to molecules already parametrized in the CHARMM forcefield, using the ParamChem Server [Vanommeslaeghe, K.; Hatcher, E.; Acharya, C; Kundu, S.; Zhong, S.; Shim, J.; Darian, E.; Guvench, O.; Lopes, P.; Vorobyov, I.; MacKerell Jr., A. D. *J. Comput. Chem.* 2010, 31, 671-690; Vanommeslaeghe, K.; MacKerell Jr., A. D. *J. Chem. Inf. Model.* 2012, 52, 3 144-3 154; Vanommeslaeghe, K.; Raman, E. P.; MacKerell Jr., A. D. *J. Chem. Inf. Model.* 2012, 52, 3 155-3 168]. All simulations were performed in NpT ensemble using periodic boundary conditions, at a constant temperature T=300 K, a Langevin constant YLang=0.001 $ps^{-1}$ (to ensure fast dynamics), and at a constant pressure p=1.01325 bar. The particle-mesh Ewald (PME) method [Darden, T.; York, D.; Pedersen, L. *J. Chem. Phys.* 1993, 98, 10089] was used for evaluation of long-range Coulombic interactions. The timestep was set to 1.0 fs, and long range interactions were evaluated every 1 (van der Waals) and 2 timesteps (Coulombic).

In the prepared system, water was minimized for 10 ps around the fixed PNA-NP, then for additional 8 ps around the constrained PNA-NP. The whole system was then heated to the temperature of 300 K and equilibrated at this temperature for 16 ns without constraints.

Partial Atomic Charges

CHARMM parameters for all atoms were prepared by analogy to known molecules, using the ParamChem Server [4-6]. The obtained partial charges were slightly modified to ensure that the unimer had no net charge. Below are the partial atomic charges for each PNA base, a unit of the PNA peptide chain, and a unit of the hydrophobic chain.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A copolymer having the formula:

$$R^1\text{-}[M(O)]_n\text{-}[M(P)]_m\text{—}R^2$$

wherein, n and m are each an integer from 2 to 1000, provided that n is greater than m;

M(O) is

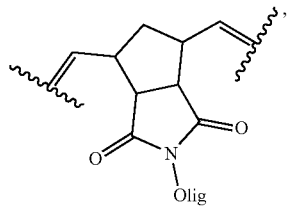

M(P) is

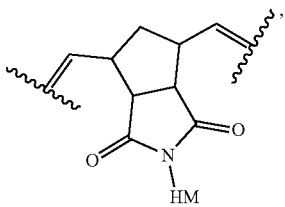

Olig is independently an oligonucleotide covalently attached directly to M or to M through a covalent linker;

HM is independently a hydrophobic moiety covalently attached to M; and $R^1$ and $R^2$ are independently terminal polymer moieties.

2. The copolymer of claim 1, wherein the copolymer is a block copolymer.

3. The copolymer of claim 1, wherein the oligonucleotide comprises at least 3 nucleobases and at least 2 different nucleobases.

4. The copolymer of claim 1, wherein the oligonucleotide comprises at least 5 nucleobases and at least 3 different nucleobases.

5. The copolymer of claim 1, wherein the oligonucleotide comprises at least 10 nucleobases and at least 4 different nucleobases.

6. The copolymer of claim 1, wherein n is an integer from 3 to 1000.

7. The copolymer of claim 1, wherein n is an integer from 5 to 1000.

8. The copolymer of claim 1, wherein n is an integer from 10 to 1000.

9. The copolymer of claim 1, wherein $R^1$ comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

10. The copolymer of claim 4, wherein $R^2$ comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

11. The copolymer of claim 1, wherein the hydrophobic moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

12. The copolymer of claim 1, wherein M(O) is

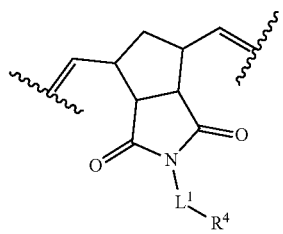

wherein, $L^1$ is independently a bond, —O—, —NH—, —COO—, —S—, —SO$_2$—, —SO$_3$—, —SO$_4$—, —SO$_2$NH—, —NHC(O)—, —C(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^4$ is the oligonucleotide.

13. The copolymer of claim 12, wherein the copolymer is a block copolymer.

14. The copolymer of claim 13, wherein the hydrophobic moiety is a substituted or unsubstituted alkyl, substituted or unsubstituted heteroalkyl, unsubstituted t cycloalkyl, substituted or unsubstituted heterocycloalkyl, substituted or unsubstituted aryl, or substituted or unsubstituted heteroaryl.

15. The copolymer of claim 14, wherein $R^1$ comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

16. The copolymer of claim 15, wherein $R^2$ comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

17. The copolymer of claim 16, wherein the oligonucleotide comprises at least 3 nucleobases and at least 2 different nucleobases.

18. The copolymer of claim 16, wherein the oligonucleotide comprises at least 5 nucleobases and at least 3 different nucleobases.

19. The copolymer of claim 16, wherein the oligonucleotide comprises at least 10 nucleobases and at least 4 different nucleobases.

20. The copolymer of claim 16, wherein n is an integer from 3 to 1000.

21. The copolymer of claim 16, wherein n is an integer from 5 to 1000.

22. The copolymer of claim 16, wherein n is an integer from 10 to 1000.

23. A method of administering an oligonucleotide to the interior of a cell comprising contacting said cell with the copolymer of claim 1.

24. The method of claim 23, wherein the method regulates the mRNA level in the cell.

25. The method of claim 23, wherein the oligonucleotide is a complimentary sequence to a nucleic acid in the cell.

26. The method of claim 25, where in the method detects a DNA sequence in the cell.

27. A method of administering an oligonucleotide to the interior of a cell comprising contacting said cell with the copolymer of claim 12.

28. The method of claim 27, wherein the method regulates the mRNA level in the cell.

29. The method of claim 27, wherein the oligonucleotide is a complimentary sequence to a nucleic acid in the cell.

30. The method of claim 29, where in the method detects a DNA sequence in the cell.

* * * * *

SEQUENCE LISTING

<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 1 gctcagtaaa